US006753136B2

(12) United States Patent
Löhning

(10) Patent No.: US 6,753,136 B2
(45) Date of Patent: Jun. 22, 2004

(54) METHODS FOR DISPLAYING (POLY) PEPTIDES/PROTEINS ON BACTERIOPHAGE PARTICLES VIA DISULFIDE BONDS

(75) Inventor: Corinna Löhning, Stockdorf (DE)

(73) Assignee: Morphosys AG (DE)

( * ) Notice: Subject to any disclaimer, the term of this patent is extended or adjusted under 35 U.S.C. 154(b) by 201 days.

(21) Appl. No.: 09/809,517

(22) Filed: Mar. 15, 2001

(65) Prior Publication Data

US 2002/0034733 A1 Mar. 21, 2002

Related U.S. Application Data

(63) Continuation of application No. PCT/EP00/06968, filed on Jul. 20, 2000.

(30) Foreign Application Priority Data

Jul. 20, 1999 (EP) .......................................... 99114072
Feb. 18, 2000 (EP) .......................................... 00103551

(51) Int. Cl.[7] ........................ G01N 33/53; C12P 21/04; C12Q 1/70

(52) U.S. Cl. ........................... 435/5; 435/7.1; 435/71.2

(58) Field of Search ............................ 435/7.1, 5, 71.2

(56) References Cited

U.S. PATENT DOCUMENTS 5,698,424 A * 12/1997 Mastico et al. .......... 435/172.3

FOREIGN PATENT DOCUMENTS

WO WO 94/00588 * 1/1994
WO WO 97/40141 * 10/1997

OTHER PUBLICATIONS

Ulrich Brinkmann et al., "Phage display of disulfide–stabilized Fv fragments", *Journal of Immunological Methods* 182, 41–50 (1995).

Reto Crameri and Mark Suter, "Display of biologically active proteins on the surface of filamentous phages: a cDNA cloning system for selection of functional gene products linked to the genetic information responsible for their production", *Gene* 137, 69–75 (1993).

* cited by examiner

*Primary Examiner*—Andrew Wang
*Assistant Examiner*—Tom Friend
(74) *Attorney, Agent, or Firm*—Heller Ehrman White and McAuliffe

(57) ABSTRACT

The present invention relates to methods for displaying (poly)peptides/proteins on the surface of bacteriophage particles by attaching the (poly)peptide/proteins via disulfide bonds.

19 Claims, 26 Drawing Sheets

FIG. 1b

Complete vector sequence of pMorphX7-hag2-LH tctagagcatgcgtaggagaaaataaaatgaaacaaagcactattgcactggcactcttaccgttgctcttcacccctgttaccaaagccgactacaaagatgaagtgcaattggtggaaagcggcggcggc
ctggtgcaaccgggcggcagcctgcgtctgagctgcgcggcctccggatttacctttagcagctatgcgatgagctgggtgcgccaagcccctgggaagggtctcgagtgggtgagcgcgattagcggtag
cggcggcagcacctattatgcggatagcgtgaaaggccgttttaccatttcacgtgataattcgaaaaacaccctgtatctgcaaatgaacagcctgcgtgcggaagatacggccgtgtattattgcgcgcgt
cgttctggtgcttatgattattggggccaaggcaccctggtgacggttagctcagcgggtggcggttctggcggcggtgggagcggtggcggtggttctggcggtggtggttccgatatcgtgatgacccag
agcccggatagcctggcggtgagcctgggcgaacgtgcgaccattaactgcagaagcagccagagcgtgctgtatagcagcaacaacaaaaactatctggcgtggtaccagcagaaaccaggtcagccg
ccgaaactattaatttattgggcatccacccgtgaaagcggggtcccggatcgttttagcggctctggatccggcactgatttaccctgaccatttcgtccctgcaagctgaagacgtggcggtgtattattgcc
agcagtattcttcttttcctcttacctttggccagggtacgaaagttgaaattaaacgtacggaattcccaggggggagcggaggcgcgccgcaccatcatcaccatcactgataagcttgacctgtgaagtga
aaaatggcgcagattgtgcgacatttttttgtctgccgtttaattaaaggggggggggggccggcctgggggggggtgtacatgaaattgtaaacgttaatattttgttaaaattcgcgttaaatttttgttaaa
tcagctcattttttaaccaataggccgaaatcggcaaaatcccttataaatcaaaagaatagaccgagatagggttgagtgttgttccagtttggaacaagagtccactattaaagaacgtggactccaacgtc
aaagggcgaaaaaccgtctatcagggcgatggcccactacgagaaccatcaccctaatcaagttttttggggtcgaggtgccgtaaagcactaaatcggaaccctaaagggagcccccgatttagagcttg
acggggaaagccggcgaacgtggcgagaaaggaagggaagaaagcgaaaggagcgggcgctagggcgctggcaagtgtagcggtcacgctgcgcgtaaccaccacacccgccgcgcttaatgcgc
cgctacagggcgcgtgctagactagtgtttaaaccggaccggggggggggcttaagtgggctgcaaaacaaaacggcctcctgtcaggaagccgcttttatcgggtagcctcactgcccgctttccagtcggg
aaacctgtcgtgccagctgcatcagtgaatcggccaacgcgcggggagaggcggtttgcgtattgggagccagggtggtttttcttttcaccagtgagacgggcaacagctgattgcccttcaccgcctggcc
ctgagagagttgcagcaagcggtccacgctggtttgccccagcaggcgaaaatcctgtttgatggtggtcagcggcgggatataacatgagctgtcctcggtatcgtcgtatcccactaccgagatgtccgca
ccaacgcgcagcccggactcggtaatggcacgcattgcgcccagcgccatctgatcgttggcaaccagcatcgcagtgggaacgatgccctcattcagcatttgcatggtttgttgaaaaccggacatggca
ctccagtcgccttcccgttccgctatcggctgaatttgattgcgagtgagatatttatgccagccagccagacgcagacgcgccgagacagaacttaatgggccagctaacagcgcgatttgctggtggccca
atgcgaccagatgctccacgcccagtcgcgtaccgtcctcatgggagaaaataatactgttgatgggtgtctggtcagagacatcaagaaataacgccggaacattagtgcaggcagcttccacagcaata
gcatcctggtcatccagcggatagttaataatcagcccactgacacgttgcgcgagaagattgtgcaccgccgctttacaggcttcgacgccgcttcgttctaccatcgacacgaccacgctggcacccagttg
atcggcgcgagatttaatcgccgcgacaatttgcgacggcgcgtgcagggccagactggaggtggcaacgccaatcagcaacgactgtttgcccgccagttgttgtgccacgcggttaggaatgtaattca
gctccgccatcgccgcttccactttttcccgcgttttcgcagaaacgtggctggcctggttcaccacgcgggaaacggtctgataagagacaccggcatactctgcgacatcgtataacgttactggtttcacatt
caccaccctgaattgactctcttccgggcgctatcatgccataccgcgaaaggttttgcgccattcgatgctagccatgtgagcaaaaggccagcaaaaggccaggaaccgtaaaaaggccgcgttgctggc
gtttttccataggctccgcccccctgacgagcatcacaaaaatcgacgctcaagtcagaggtggcgaaacccgacaggactataaagataccaggcgtttccccctggaagctccctcgtgcgctctcctgttc
cgaccctgccgcttaccggatacctgtccgcctttctcccttcgggaagcgtggcgctttctcatagctcacgctgtaggtatctcagttcggtgtaggtcgttcgctccaagctgggctgtgtgcacgaaccccc
gttcagcccgaccgctgcgccttatccggtaactatcgtcttgagtccaacccggtaagacacgacttatcgccactggcagcagccactggtaacaggattagcagagcgaggtatgtaggcggtgctaca
gagttcttgaagtggtggcctaactacggctacactagaagaacagtatttggtatctgcgctctgctgtagccagttaccttcggaaaaagagttggtagctcttgatccggcaaacaaaccaccgctggtag
cggtggtttttttgtttgcaagcagcagattacgcgcagaaaaaaaggatctcaagaagatcctttgatcttttctacggggtctgacgctcagtggaacgaaaactcacgttaagggattttggtcagatctag
caccaggcgtttaagggcaccaataactgccttaaaaaaattacgccccgccctgccactcatcgcagtactgttgtaattcattaagcattctgccgacatggaagccatcacaaacggcatgatgaacctga
atcgccagcggcatcagcaccttgtcgccttgcgtataatatttgcccatagtgaaaacgggggcgaagaagttgtccatattggctacgtttaaatcaaaactggtgaaactcacccagggattggctgaga
cgaaaaacatattctcaataaaccctttagggaaataggccaggttttcaccgtaacacgccacatcttgcgaatatatgtgtagaaactgccggaaatcgtcgtggtattcactccagagcgatgaaaacgtt
tcagtttgctcatggaaaacggtgtaacaagggtgaacactatcccatatcaccagctcaccgtctttcattgccatacggaactccgggtgagcattcatcaggcgggcaagaatgtgaataaaggccggat
aaaacttgtgcttatttttctttacggtctttaaaaaggccgtaatatccagctgaacggtctggttataggtacattgagcaactgactgaaatgcctcaaaatgttctttacgatgccattgggatatatcaacgg
tggtatatccagtgatttttttctccattttagcttccttagctcctgaaaatctcgataactcaaaaaatacgcccggtagtgatcttatttcattatggtgaaagttggaacctcacccgacgtctaatgtgagttag
ctcactcattaggcaccccaggctttacactttatgcttccggctcgtatgttgtgtggaattgtgagcggataacaatttcacacaggaaacagctatgaccatgattacgaatt

FIG. 2

Complete vector sequence of pTFT74-N1-hag-HIPM acccgacaccatcgaaattaatacgactcactatagggagaccacaacggtttcccgaattgtgagcggataacaatagaaataattttgtttaactttaagaaggagatatatccatggctgaa
actgttgaaagttgtttagcaaaatcccatacagaaaattcatttactaacgtctggaaagacgacaaaactttagatcgttacgctaactatgagggctgtctgtggaatgctacaggcgttgtag
tttgtactggtgacgaaactcagtgttacggtacatgggttcctattgggcttgctatccctgaaaatgagggtggtggctctgagggtggcggttctccgtacgacgttccagactacgcttccctg
cgttcccatcaccatcaccatcactaagcttcagtcccgggcagtggatccggctgctaacaaagcccgaaaggaagctgagttggctgctgccaccgctgagcaataactagcataaccccttg
gggcctctaaacgggtcttgaggggttttttgctgaaaggaggaactatatccggatcgagatccccacgcgccctgtagcggcgcattaagcgcggcgggtgtggtggttacgcgcagcgtga
ccgctacacttgccagcgccctagcgcccgctcctttcgctttcttcccttcctttctcgccacgttcgccggctttccccgtcaagctctaaatcggggcatccctttagggttccgatttagtgctttac
ggcacctcgaccccaaaaaacttgattagggtgatggttcacgtagtgggccatcgccctgatagacggtttttcgccctttgacgttggagtccacgttctttaatagtggactcttgttccaaact
ggaacaacactcaaccctatctcggtctattcttttgatttataagggattttgccgatttcggcctattggttaaaaaatgagctgatttaacaaaaatttaacgcgaattttaacaaaatattaacgt
ttacaatttcaggtggcacttttcggggaaatgtgcgcggaacccctatttgtttatttttctaaatacattcaaatatgtatccgctcatgagacaataaccctgataaatgcttcaataatattgaaa
aaggaagagtatgagtattcaacatttccgtgtcgcccttattcccttttttgcggcattttgccttcctgtttttgctcacccagaaacgctggtgaaagtaaaagatgctgaagatcagttgggtgc
acgagtgggttacatcgaactggatctcaacagcggtaagatccttgagagttttcgccccgaagaacgttttccaatgatgagcacttttaaagttctgctatgtggcgcggtattatcccgtattg
acgccgggcaagagcaactcggtcgccgcatacactattctcagaatgacttggttgagtactcaccagtcacagaaaagcatcttacggatggcatgacagtaagagaattatgcagtgctgc
cataaccatgagtgataacactgcggccaacttacttctgacaacgatcggaggaccgaaggagctaaccgcttttttgcacaacatgggggatcatgtaactcgccttgatcgttgggaaccgg
agctgaatgaagccataccaaacgacgagcgtgacaccacgatgcctgtagcaatggcaacaacgttgcgcaaactattaactggcgaactacttactctagcttcccggcaacaattaataga
ctggatggaggcggataaagttgcaggaccacttctgcgctcggcccttccggctggctggtttattgctgataaatctggagccggtgagcgtgggtctcgcggtatcattgcagcactggggc
cagatggtaagccctcccgtatcgtagttatctacacgacggggagtcaggcaactatggatgaacgaaatagacagatcgctgagataggtgcctcactgattaagcattggtaactgtcaga
ccaagtttactcatatatactttagattgatttaaaacttcatttttaatttaaaaggatctaggtgaagatcctttttgataatctcatgaccaaaatcccttaacgtgagttttcgttccactgagcgtc
agaccccgtagaaaagatcaaaggatcttcttgagatcctttttttctgcgcgtaatctgctgcttgcaaacaaaaaaaccaccgctaccagcggtggtttgtttgccggatcaagagctaccaact
ctttttccgaaggtaactggcttcagcagagcgcagataccaaatactgtccttctagtgtagccgtagttaggccaccacttcaagaactctgtagcaccgcctacatacctcgctctgctaatcct
gttaccagtggctgctgccagtggcgataagtcgtgtcttaccgggttggactcaagacgatagttaccggataaggcgcagcggtcgggctgaacggggggttcgtgcacacagcccagctt
ggagcgaacgacctacaccgaactgagatacctacagcgtgagctatgagaaagcgccacgcttcccgaagggagaaaggcggacaggtatccggtaagcggcagggtcggaacaggag
agcgcacgagggagcttccagggggaaacgcctggtatctttatagtcctgtcgggtttcgccacctctgacttgagcgtcgatttttgtgatgctcgtcaggggggcggagcctatggaaaaac
gccagcaacgcggcctttttacggttcctggccttttgctggccttttgctcacatg

FIG. 3

Complete vector sequence of pQE60-MacI agcttaattagctgagcttggactcctgttgatagatccagtaatgacctcagaactccatctggatttgttcagaacgctcggttgccgccgggcgttttttattggtgagaatccaagctagctt
ggcgagattttcaggagctaaggaagctaaaatggagaaaaaaatcactggatataccaccgttgatatatcccaatggcatcgtaaagaacattttgaggcatttcagtcagttgctcaatgt
acctataaccagaccgttcagctggatattacggcctttttaaagaccgtaaagaaaaataagcacaagttttatccggcctttattcacattcttgcccgcctgatgaatgctcatccggaatttc
gtatggcaatgaaagacggtgagctggtgatatgggatagtgttcacccttgttacaccgttttccatgagcaaactgaaacgttttcatcgctctggagtgaataccacgacgatttccggcag
tttctacacatatattcgcaagatgtggcgtgttacggtgaaaacctggcctatttccctaaagggtttattgagaatatgtttttcgtctcagccaatccctgggtgagtttcaccagttttgatttaa
acgtggccaatatggacaacttcttcgcccccgttttcaccatgcatgggcaaatattatacgcaaggcgacaaggtgctgatgccgctggcgattcaggttcatcatgccgtctgtgatggctt
ccatgtcggcagaatgcttaatgaattacaacagtactgcgatgagtggcagggcggggcgtaatttttttaaggcagttattggtgcccttaaacgcctggggtaatgactctctagcttgagg
catcaaataaaacgaaaggctcagtcgaaagactgggcctttcgttttatctgttgtttgtcggtgaacgctctcctgagtaggacaaatccgccgctctagagctgcctcgcgcgtttcggtgat
gacggtgaaaacctctgacacatgcagctcccggagacggtcacagcttgtctgtaagcggatgccgggagcagacaagcccgtcagggcgcgtcagcgggtgttggcgggtgtcgggg
cgcagccatgacccagtcacgtagcgatagcggagtgtatactggcttaactatgcggcatcagagcagattgtactgagagtgcaccatatgcggtgtgaaataccgcacagatgcgtaag
gagaaaataccgcatcaggcgctcttccgcttcctcgctcactgactcgctgcgctcggtcgttcggctgcggcgagcggtatcagctcactcaaaggcggtaatacggttatccacagaatca
ggggataacgcaggaaagaacatgtgagcaaaaggccagcaaaaggccaggaaccgtaaaaaggccgcgttgctggcgtttttccataggctccgcccccctgacgagcatcacaaaaa
tcgacgctcaagtcagaggtggcgaaacccgacaggactataaagataccaggcgtttccccctggaagctccctcgtgcgctctcctgttccgaccctgccgcttaccggatacctgtccgcc
tttctcccttcgggaagcgtggcgctttctcaatgctcacgctgtaggtatctcagttcggtgtaggtcgttcgctccaagctgggctgtgtgcacgaaccccccgttcagcccgaccgctgcgcct
tatccggtaactatcgtcttgagtccaacccggtaagacacgacttatcgccactggcagcagccactggtaacaggattagcagagcgaggtatgtaggcggtgctacagagttcttgaagt
ggtggcctaactacggctacactagaaggacagtatttggtatctgcgctctgctgaagccagttaccttcggaaaaagagttggtagctcttgatccggcaaacaaaccaccgctggtagcg
gtggtttttttgtttgcaagcagcagattacgcgcagaaaaaaaggatctcaagaagatcctttgatcttttctacggggtctgacgctcagtggaacgaaaactcacgttaagggattttggtc
atgagattatcaaaaaggatcttcacctagatccttttaaattaaaaatgaagttttaaatcaatctaaagtatatatgagtaaacttggtctgacagttaccaatgcttaatcagtgaggcaccta
tctcagcgatctgtctatttcgttcatccatagctgcctgactccccgtcgtgtagataactacgatacgggagggcttaccatctggccccagtgctgcaatgataccgcgagacccacgctcac
cggctccagatttatcagcaataaaccagccagccggaagggccgagcgcagaagtggtcctgcaactttatccgcctccatccagtctattaattgttgccgggaagctagagtaagtagtt
cgccagttaatagtttgcgcaacgttgttgccattgctacaggcatcgtggtgtcacgctcgtcgtttggtatggcttcattcagctccggttcccaacgatcaaggcgagttacatgatcccccat
gttgtgcaaaaaagcggttagctccttcggtcctccgatcgttgtcagaagtaagttggccgcagtgttatcactcatggttatggcagcactgcataattctcttactgtcatgccatccgtaaga
tgcttttctgtgactggtgagtactcaaccaagtcattctgagaatagtgtatgcggcgaccgagttgctcttgcccggcgtcaatacgggataataccgcgccacatagcagaactttaaaagt
gctcatcattggaaaacgttcttcggggcgaaaactctcaaggatcttaccgctgttgagatccagttcgatgtaacccactcgtgcacccaactgatcttcagcatcttttactttcaccagcgttt
ctgggtgagcaaaaacaggaaggcaaaatgccgcaaaaaagggaataagggcgacacggaaatgttgaatactcatactcttcctttttcaatattattgaagcatttatcagggttattgtct
catgagcggatacatatttgaatgtatttagaaaaataaacaaataggggttccgcgcacatttccccgaaaagtgccacctgacgtctaagaaaccattattatcatgacattaacctataaa
aataggcgtatcacgaggccctttcgtcttcacctcgagaaatcataaaaaatttatttgctttgtgagcggataacaattataatagattcaattgtgagcggataacaatttcacacagaattc
attaaagaggagaaattaaccatgagtgacattgccttcttgattgatggctctggtagcatcatcccacatgactttcggcggatgaaggagtttgtctcaactgtgatggagcaattaaaaaa
gtccaaaaccttgttctctttgatgcagtactctgaagaattccggattcacttaccttcaaagagttccagaacaaccctaacccaagatcactggtgaagccaataacgcagctgcttgggc
ggacacacacggccacgggcatccgcaaagtggtacgagagctgtttaacatcaccaacggagcccgaaagaatgcctttaagatcctagttgtcatcacggatggagaaaagtttggcga
tcccttgggatatgaggatgtcatccctgaggcagacagagagggagtcattcgctacgtcattggggtgggagatgccttccgcagtgagaaatcccgccaagagcttaataccatcgcatc
caagccgcctcgtgatcacgtgttccaggtgaataactttgaggctctgaagaccattcagaaccagcttcgggagaagatctttgcgatcgagggtactcagacaggaagtagcagctcctt
tgagcatgagatgtctcaggaaatcgaaggtagacatcaccatcaccatcactaga

FIG. 6b

Sequence of expression cassette for full length pIII with an N-terminal cysteine residue (C-gIII)

gctagcctgaggccagtttgctcaggctctccccgtggaggtaataattgctcgaccgataaaagcggcttcctgacaggaggccgttttgttttgcagcccacctcaacgcaattaatgtgagtta
gctcactcattaggcaccccaggctttacactttatgcttccggctcgtatgttgtgtggaattgtgagcggataacaatttcacacaggaaacagctatgaccatgattacgaatttctagataacg
agggcaaaaaatgaaaaagacagctatcgcgattgcagtggcactggctggtttcgctaccgtagcgcaggccgactactgcgatatcgaattcgcagaaacagttgaaagttgtttagcaaa
accccatacagaaaattcatttactaacgtctggaaagacgacaaaactttagatcgttacgctaactatgagggctgtctgtggaatgctacaggcgttgtagtttgtactggtgacgaaactca
gtgttacggtacatgggttcctattgggcttgctatccctgaaaatgagggtggtggctctgagggtggcggttctgagggtggcggctctgagggtggcggtactaaacctcctgagtacggtg
atacacctattccgggctatacttatatcaaccctctcgacggcacttatccgcctggtactgagcaaaaccccgctaatcctaatccttctcttgaggagtctcagcctcttaatactttcatgtttcag
aataataggttccgaaataggcagggggcattaactgtttatacgggcactgttactcaaggcactgaccccgttaaaacttattaccagtacactcctgtatcatcaaaagccatgtatgacgctt
actggaacggtaaattcagagactgcgctttccattctggctttaatgaggatccattcgtttgtgaatatcaaggccaatcgtctgacctgcctcaacctcctgtcaatgctggcggcggctctggt
ggtggttctggtggcggctctgagggtggcggctctgagggtggcggttctgagggtggcggctctgagggtggcggttccggtggcggctccggttccggtgattttgattatgaaaaaatgg
caaacgctaataagggggctatgaccgaaaatgccgatgaaaacgcgctacagtctgacgctaaaggcaaacttgattctgtcgctactgattacggtgctgctatcgatggtttcattggtgac
gtttccggccttgctaatggtaatggtgctactggtgattttgctggctctaattcccaaatggctcaagtcggtgacggtgataattcacctttaatgaataatttccgtcaatatttaccttctttgcct
cagtcggttgaatgtcgcccttatgtctttggcgctggtaaaccatatgaattttctattgattgtgacaaaataaacttattccgtggtgtctttgcgtttcttttatatgttgccacctttatgtatgtattt
tcgacgtttgctaacatactgcgtaataaggagtcttaagctt

FIG. 6c

Sequence of expression cassette for truncated pIII with an N-terminal cysteine residue (C-gIIICT)

gctagcctgaggccagtttgctcaggctctccccgtggaggtaataattgctcgaccgataaaagcggcttcctgacaggaggccgttttgttttgcagcccacctcaacgcaattaatgtgagtta
gctcactcattaggcaccccaggctttacactttatgcttccggctcgtatgttgtgtggaattgtgagcggataacaatttcacacaggaaacagctatgaccatgattacgaatttctagataacg-
agggcaaaaaatgaaaaagacagctatcgcgattgcagtggcactggctggtttcgctaccgtagcgcaggccgactactgcgatatcgaattcaatgctggcggcggctctggtggtggttct
ggtggcggctctgagggtggtggctctgagggtggcggttctgagggtggcggctctgagggaggcggttccggtggtggctctggttccggtgattttgattatgaaaagatggcaaacgcta
ataagggggctatgaccgaaaatgccgatgaaaacgcgctacagtctgacgctaaaggcaaacttgattctgtcgctactgattacggtgctgctatcgatggtttcattggtgacgtttccggcc
ttgctaatggtaatggtgctactggtgattttgctggctctaattcccaaatggctcaagtcggtgacggtgataattcacctttaatgaataatttccgtcaatatttaccttccctccctcaatcggttg
aatgtcgcccttttgtctttggcgctggtaaaccatatgaattttctattgattgtgacaaaataaacttattccgtggtgtctttgcgtttcttttatatgttgccacctttatgtatgtattttctacgtttgc
taacatactgcgtaataaggagtcttgataagctt

FIG. 7b

Complete vector sequence of pMorph18-C-gIII-hag2-LHC tctagataacgagggcaaaaaatgaaaaagacagctatcgcgattgcagtggcactggctggtttcgctaccgtagcgcaggccgactactgcgatatcgaattcgcagaaacagttgaaagttgtttagcaaaa
ccccatacagaaaattcatttactaacgtctggaaagacgacaaaacttagatcgttacgctaactatgagggctgtctgtggaatgctacaggcgttgtagtttgtactggtgacgaaactcagtgttacggtaca
tgggttcctattgggcttgctatccctgaaaatgagggtggtggctctgagggtggcggttctgagggtggcggctctgagggtggcggtactaaacctcctgagtacggtgatacacctattccgggctatacttat
atcaaccctctcgacggcacttatccgcctggtactgagcaaaaccccgctaatcctaatccttctcttgaggagtctcagcctcttaatactttcatgtttcagaataataggttccgaaataggcagggggcattaac
tgtttatacgggcactgttactcaaggcactgaccccgttaaaacttattaccagtacactcctgtatcatcaaaagccatgtatgacgcttactggaacggtaaattcagagactgcgctttccattctggctttaatga
ggatccattcgtttgtgaatatcaaggccaatcgtctgacctgcctcaacctcctgtcaatgctggcggcggctctggtggtggttctggtggcggctctgagggtggcggctctgagggtggcggttctgagggtg
gcggctctgagggtggcggttccggtggcggctccggttccggtgattttgattatgaaaaaatggcaaacgctaataagggggctatgaccgaaaatgccgatgaaaacgcgctacagtctgacgctaaaggc
aaacttgattctgtcgctactgattacggtgctgctatcgatggtttcattggtgacgtttccggccttgctaatggtaatggtgctactggtgattttgctggctctaattcccaaatggctcaagtcggtgacggtgata
attcacctttaatgaataatttccgtcaatatttaccttctttgcctcagtcggttgaatgtcgcccttatgtctttggcgctggtaaaccatatgaattttctattgattgtgacaaaataaacttattccgtggtgtctttgcg
tttcttttatatgttgccacctttatgtatgtattttcgacgtttgctaacatactgcgtaataaggagtcttaaggcctgataagcatgcgtaggagaaaataaaatgaaacaaagcactattgcactggcactcttacc
gttgctcttcacccctgttaccaaagccgactacaaagatgaagtgcaattggtggaaagcggcggcggcctggtgcaaccgggcggcagcctgcgtctgagctgcgcggcctccggatttacctttagcagctat
gcgatgagctgggtgcgccaagcccctgggaagggtctcgagtgggtgagcgcgattagcggtagcggcggcagcacctattatgcggatagcgtgaaaggccgttttaccatttcacgtgataattcgaaaaa
caccctgtatctgcaaatgaacagcctgcgtgcggaagatacggccgtgtattattgcgcgcgtcgttctggtgcttatgattattggggccaaggcaccctggtgacggttagctcagcgggtggcggttctggcg
gcggtgggagcggtggcggtggttctggcggtggtggttccgatatcgtgatgacccagagcccggatagcctggcggtgagcctgggcgaacgtgcgaccattaactgcagaagcagccagagcgtgctgta
tagcagcaacaacaaaaactatctggcgtggtaccagcagaaaccaggtcagccgccgaaactattaatttattgggcatccacccgtgaaagcggggtcccggatcgttttagcggctctggatccggcactga
ttttaccctgaccatttcgtccctgcaagctgaagacgtggcggtgtattattgccagcagtattcttcttttcctcttacctttggccagggtacgaaagttgaaattaaacgtacggaattcccagggggggagcggag
gcgcgccgcaccatcatcaccatcactgctgataagcttgacctgtgaagtgaaaaatggcgcagattgtgcgacattttttttgtctgccgtttaatgaaattgtaaacgttaatattttgttaaaattcgcgttaaattt
ttgttaaatcagctcattttttaaccaataggccgaaatcggcaaaatcccttataaatcaaaagaatagaccgagatagggttgagtgttgttccagtttggaacaagagtccactattaaagaacgtggactccaa
cgtcaaagggcgaaaaaccgtctatcagggcgatggcccactacgagaaccatcaccctaatcaagttttttggggtcgaggtgccgtaaagcactaaatcggaaccctaaagggagcccccgatttagagcttg
acggggaaagccggcgaacgtggcgagaaaggaagggaagaaagcgaaaggagcgggcgctagggcgctggcaagtgtagcggtcacgctgcgcgtaaccaccacacccgccgcgcttaatgcgccgct
acagggcgcgtgctagccatgtgagcaaaaggccagcaaaaggccaggaaccgtaaaaaggccgcgttgctggcgtttttccataggctccgcccccctgacgagcatcacaaaaatcgacgctcaagtcaga
ggtggcgaaacccgacaggactataaagataccaggcgtttccccctggaagctccctcgtgcgctctcctgttccgaccctgccgcttaccggatacctgtccgcctttctcccttcgggaagcgtggcgctttctca
tagctcacgctgtaggtatctcagttcggtgtaggtcgttcgctccaagctgggctgtgtgcacgaaccccccgttcagtccgaccgctgcgccttatccggtaactatcgtcttgagtccaacccggtaagacacgac
ttatcgccactggcagcagccactggtaacaggattagcagagcgaggtatgtaggcggtgctacagagttcttgaagtggtggcctaactacggctacactagaagaacagtatttggtatctgcgctctgctgaa
gccagttaccttcggaaaaagagttggtagctcttgatccggcaaacaaaccaccgctggtagcggtggtttttttgtttgcaagcagcagattacgcgcagaaaaaaaggatctcaagaagatcctttgatcttttc
tacggggtctgacgctcagtggaacgaaaactcacgttaagggattttggtcagatctagcaccaggcgtttaagggcaccaataactgccttaaaaaaattacgccccgccctgccactcatcgcagtactgttgt
aattcattaagcattctgccgacatggaagccatcacaaacggcatgatgaacctgaatcgccagcggcatcagcaccttgtcgccttgcgtataatatttgcccatagtgaaaacgggggcgaagaagttgtcca
tattggctacgtttaaatcaaaactggtgaaactcacccagggattggctgagacgaaaaacatattctcaataaaccctttagggaaataggccaggttttcaccgtaacacgccacatcttgcgaatatatgtgta
gaaactgccggaaatcgtcgtggtattcactccagagcgatgaaaacgtttcagtttgctcatggaaaacggtgtaacaagggtgaacactatcccatatcaccagctcaccgtctttcattgccatacggaactcc
gggtgagcattcatcaggcgggcaagaatgtgaataaaggccggataaaacttgtgcttatttttctttacggtctttaaaaaggccgtaatatccagctgaacggtctggttataggtacattgagcaactgactga
aatgcctcaaaatgttctttacgatgccattgggatatatcaacggtggtatatccagtgatttttttctccattttagcttccttagctcctgaaaatctcgataactcaaaaaatacgcccggtagtgatcttatttcatta
tggtgaaagttggaacctcacccgacgtctaatgtgagttagctcactcattaggcaccccaggctttacactttatgcttccggctcgtatgttgtgtggaattgtgagcggataacaatttcacacaggaaacagct
atgaccatgattacgaatt

- scFv-S-S-pIII
- scFv-S-S-scFv / (scFv-SH)$_2$ / (scFv)$_2$
- scFv-S-S-x
- scFv-SH / scFv

- pIII-S-S-pIII
- scFv-S-S-pIII
- SH-pIII / pIII

FIG. 16b

Complete vector sequence of pMorphX10-Fab-MacI5-VL-LHC-VH-FS tctagataacgagggcaaaaaatgaaaaagacagctatcgcgattgcagtggcactggctggtttcgctaccgtagcgcaggccgatatcgtgctgacccagccgccttcagtgagtggcgcaccaggtcagcg
tgtgaccatctcgtgtagcggcagcagcagcaacattggcagcaactatgtgagctggtaccagcagttgcccgggacggcgccgaaactgctgatttatgataacaaccagcgtccctcaggcgtgccggatcg
tttagcggatccaaaagcggcaccagcgcgagccttgcgattacgggcctgcaaagcgaagacgaagcggattattattgccagagctatgaccagaatgctcttgttgaggtgtttggcggcggcacgaagtt
aaccgttcttggccagccgaaagccgcaccgagtgtgacgctgtttccgccgagcagcgaagaattgcaggcgaacaaagcgaccctggtgtgcctgattagcgactttatccgggagccgtgacagtggcctg
gaaggcagatagcagccccgtcaaggcgggagtggagaccaccacaccctccaaacaaagcaacaacaagtacgcggccagcagctatctgagcctgacgcctgagcagtggaagtcccacagaagctaca
gctgccaggtcacgcatgaggggagcaccgtggaaaaaaccgttgcgccgactgaggcctctccaggggggagcggaggcgcgccgcaccatcatcaccatcactgctgataatatgcatgcgtaggagaaa
ataaaatgaaacaaagcactattgcactggcactcttaccgttgctcttcacccctgttaccaaagcccaggtgcaattgaaagaaagcggcccggccctggtgaaaccgacccaaaccctgaccctgacctgtac
cttttccggatttagcctgtccacgtctggcgttggcgtgggctggattcgccagccgcctgggaaagccctcgagtggctggctctgattgattgggatgatgataagtattatagcaccagcctgaaaacgcgtct
gaccattagcaaagatacttcgaaaaatcaggtggtgctgactatgaccaacatggacccggtggatacggccacctattattgcgcgcgttttgatcctttttttgattctttttttgattattggggccaaggcaccct
ggtgacggttagctcagcgtcgaccaaaggtccaagcgtgtttccgctggctccgagcagcaaaagcaccagcggcggcacggctgccctgggctgcctggttaaagattatttccggaaccagtcaccgtgag
ctggaacagcggggcgctgaccagcggcgtgcatacctttccggcggtgctgcaaagcagcggcctgtatagcctgagcagcgttgtgaccgtgccgagcagcagcttaggcactcagacctatatttgcaacgt
gaaccataaaccgagcaacaccaaagtggataaaaaagtggaaccgaaaagcgaattcgactataaagatgacgatgacaaaggcgcgccgtggagccacccgcagtttgaaaaatgataagcttgacctgt
gaagtgaaaaatggcgcagattgtgcgacatttttttgtctgccgtttaattaaaggggggggggggccggcctggggggggtgtacatgaaattgtaaacgttaatattttgttaaaattcgcgttaaatttttgt
taaatcagctcattttttaaccaataggccgaaatcggcaaaatcccttataaatcaaaagaatagaccgagatagggttgagtgttgttccagtttggaacaagagtccactattaaagaacgtggactccaacgt
caaagggcgaaaaaccgtctatcagggcgatggcccactacgagaaccatcaccctaatcaagttttttggggtcgaggtgccgtaaagcactaaatcggaaccctaaagggagcccccgatttagagcttgac
ggggaaagccggcgaacgtggcgagaaaggaagggaagaaagcgaaaggagcgggcgctagggcgctggcaagtgtagcggtcacgctgcgcgtaaccaccacacccgccgcgcttaatgcgccgctac
agggcgcgtgctagactagtgtttaaaccggaccggggggggggcttaagtgggctgcaaaacaaaacggcctcctgtcaggaagccgctttatcgggtagcctcactgcccgctttccagtcgggaaacctgtc
gtgccagctgcatcagtgaatcggccaacgcgcggggagaggcggtttgcgtattgggagccagggtggtttttcttttcaccagtgagacgggcaacagctgattgcccttcaccgcctggccctgagagagttg
cagcaagcggtccacgctggtttgccccagcaggcgaaaatcctgtttgatggtggtcagcggcgggatataacatgagctgtcctcggtatcgtcgtatcccactaccgagatgtccgcaccaacgcgcagcccg
gactcggtaatggcacgcattgcgcccagcgccatctgatcgttggcaaccagcatcgcagtgggaacgatgccctcattcagcatttgcatggtttgttgaaaaccggacatggcactccagtcgccttcccgttcc
gctatcggctgaatttgattgcgagtgagatatttatgccagccagccagacgcagacgcgccgagacagaacttaatgggccagctaacagcgcgatttgctggtggcccaatgcgaccagatgctccacgccc
agtcgcgtaccgtcctcatgggagaaaataatactgttgatgggtgtctggtcagagacatcaagaaataacgccggaacattagtgcaggcagcttccacagcaatagcatcctggtcatccagcggatagtta
ataatcagcccactgacacgttgcgcgagaagattgtgcaccgccgctttacaggcttcgacgccgcttcgttctaccatcgacacgaccacgctggcacccagttgatcggcgcgagatttaatcgccgcgacaat
ttgcgacggcgcgtgcagggccagactggaggtggcaacgccaatcagcaacgactgtttgcccgccagttgttgtgccacgcggttaggaatgtaattcagctccgccatcgccgcttccactttttcccgcgtttt
cgcagaaacgtggctggcctggttcaccacgcgggaaacggtctgataagagacaccggcatactctgcgacatcgtataacgttactggtttcacattcaccaccctgaattgactctcttccgggcgctatcatgc
cataccgcgaaaggttttgcgccattcgatgctagccatgtgagcaaaaggccagcaaaaggccaggaaccgtaaaaaggccgcgttgctggcgtttttccataggctccgcccccctgacgagcatcacaaaa
atcgacgctcaagtcagaggtggcgaaacccgacaggactataaagataccaggcgtttccccctggaagctccctcgtgcgctctcctgttccgaccctgccgcttaccggatacctgtccgcctttctcccttcgg
gaagcgtggcgctttctcatagctcacgctgtaggtatctcagttcggtgtaggtcgttcgctccaagctgggctgtgtgcacgaaccccccgttcagcccgaccgctgcgccttatccggtaactatcgtcttgagtc
caacccggtaagacacgacttatcgccactggcagcagccactggtaacaggattagcagagcgaggtatgtaggcggtgctacagagttcttgaagtggtggcctaactacggctacactagaagaacagtat
ttggtatctgcgctctgctgtagccagttaccttcggaaaaagagttggtagctcttgatccggcaaacaaaccaccgctggtagcggtggtttttttgtttgcaagcagcagattacgcgcagaaaaaaaggatctc
aagaagatcctttgatcttttctacggggtctgacgctcagtggaacgaaaactcacgttaagggattttggtcagatctagcaccaggcgtttaagggcaccaataactgccttaaaaaaattacgccccgccctgc
cactcatcgcagtactgttgtaattcattaagcattctgccgacatggaagccatcacaaacggcatgatgaacctgaatcgccagcggcatcagcaccttgtcgccttgcgtataatatttgcccatagtgaaaacg
ggggcgaagaagttgtccatattggctacgtttaaatcaaaactggtgaaactcacccagggattggctgagacgaaaaacatattctcaataaaccctttagggaaataggccaggttttcaccgtaacacgcca
catcttgcgaatatatgtgtagaaactgccggaaatcgtcgtggtattcactccagagcgatgaaaacgtttcagtttgctcatggaaaacggtgtaacaagggtgaacactatcccatatcaccagctcaccgtctt
tcattgccatacggaactccgggtgagcattcatcaggcgggcaagaatgtgaataaaggccggataaaacttgtgcttatttttctttacggtctttaaaaaggccgtaatatccagctgaacggtctggttataggt
acattgagcaactgactgaaatgcctcaaaatgttctttacgatgccattgggatatatcaacggtggtatatccagtgatttttttctccattttagcttccttagctcctgaaaatctcgataactcaaaaaatacgccc
ggtagtgatcttatttcattatggtgaaagttggaacctcacccgacgtctaatgtgagttagctcactcattaggcaccccaggctttacactttatgcttccggctcgtatgttgtgtggaattgtgagcggataacaa
tttcacacaggaaacagctatgaccatgattacgaatt

METHODS FOR DISPLAYING (POLY) PEPTIDES/PROTEINS ON BACTERIOPHAGE PARTICLES VIA DISULFIDE BONDS

CROSS REFERENCE TO RELATED APPLICATIONS

This application is based upon, and claims priority to, European patent applications EP 99 11 4072.4 and EP 00 103551.8 and PCT application PCT/EP00/06968, filed Jul. 20, 2000, which are incorporated herein by reference in their entirety.

BACKGROUND OF THE INVENTION

The present invention relates to methods for displaying (poly)peptides/proteins on the surface of bacteriophage particles by attaching the (poly)peptide/proteins via disulfide bonds. A number of documents are cited throughout this specification. The disclosure content of these documents is herewith incorporated by reference in their entirety.

Smith first demonstrated in 1985 that filamentous phage tolerate foreign protein fragments inserted in their gene III protein (pIII), and could show that the protein fragments are presented on the phage surface (Smith, 1985). Ladner extended that concept to the screening of repertoires of (poly)peptides and/or proteins displayed on the surface of phage (WO 88/06630; WO 90/02809) and, since then, phage display has experienced a dramatic progress and resulted in substantial achievements.

Various formats have been developed to construct and screen (poly)peptide/protein phage-display libraries, and a large number of review articles and monographs cover and summarise these developments (e.g., Kay et al., 1996; Dunn, 1996; McGregor, 1996).

Most often, filamentous phage-based systems have been used.

Initially proposed as display of single-chain Fv (scFv) fragments (WO 88/06630; see additionally WO 92/01047), the method has rapidly been expanded to the display of bovine pancreatic trypsin inhibitor (BPTI) (WO 90/02809), peptide libraries (WO 91/19818), human growth hormone (WO 92/09690), and of various other proteins including the display of multimeric proteins such as Fab fragments (WO 91/17271; WO 92/01047).

To anchor the peptide or protein to the filamentous bacteriophage surface, mostly genetic fusions to phage coat proteins are employed. Preferred are fusions to gene III protein (Parmley & Smith, 1988) or fragments thereof (Bass et al., 1990), and gene VIII protein (Greenwood et al., 1991). In one case, gene VI has been used (Jespers et al., 1995), and recently, a combination of gene VII and gene IX has been used for the display of Fv fragments (Gao et al., 1999).

Furthermore, phage display has also been achieved on phage lambda. In that case, gene V protein (Maruyama et al., 1994), gene J protein, and gene D protein (Sternberg & Hoess, 1995; Mikawa et al., 1996) have been used.

Besides using genetic fusions, foreign peptides or proteins have been attached to phage surfaces via association domains. In WO 91/17271, it was suggested to use a tag displayed on phage and a tag binding ligand fused to the peptide/protein to be displayed to achieve a non-covalent display.

A similar concept was pursued for the display of cDNA libraries (Crameri & Suter, 1993). There the jun/fos interaction was used to mediate the display of cDNA fragments. In their construct, additional cysteine residues flanking both ends of jun as well as fos further stabilised the interaction by forming two disulfide bonds When screening phage display libraries in biopanning the problem remains how best to recover phage which have bound to the desired target. Normally, this is achieved by elution with appropriate buffers, either by using a pH- or salt gradient, or by specific elution using soluble target. However, the most interesting binders which bind with high affinity to the target might be lost by that approach. Several alternative methods have been devised which try to overcome that problem, either by providing a cleavage signal between the (poly)peptide/protein being displayed and its fusion partner, or between the target of interest and its carrier which anchors the target to a solid surface.

Furthermore, all the approaches referred to hereinabove require to use fusion proteins comprising at least part of a phage coat protein and a foreign (poly)peptide/protein. Especially in the case of using gene III as partner for peptides/proteins to be displayed, this leads to several problems. First, the expression product of gene III is toxic to the host cell, which requires tight regulation of gene III fusion proteins. Second, expression of gene III products can make host cells resistant to infection with helper phage required for the production of progeny phage particles. And finally, recombination events between gene III fusion constructs and wild type copies of gene III lead to undesired artefacts. Furthermore, since at least the C-terminal domain of the gene III protein comprising about 190 amino acids has to be used in order to achieve incorporation of the fusion protein into the phage coat, the size of the vectors comprising the nucleic acid sequences is rather larger, leading to a decrease in transformation efficiency. Transformation efficiency, however, is a crucial factor for the production of very large libraries. Additionally, for the characterisation of (poly) peptide/proteins obtained after selection from a phage display library, the (poly)peptide/protein are usually recloned into expression vectors in order to remove the phage coat protein fusion partner, or in order to create new fusion proteins such as by fusion to enzymes for detection or to multimerisation domains. It would be advantageously to have a system which would allow direct expression without recloning, and direct coupling of the (poly)peptide/protein to other moieties.

Furthermore, most of these approaches (except for the work of Jespers et al. (1995), WO 91/17271, and Crameri & Suter (1993) mentioned hereinabove) are limited to the presentation of (poly)peptides/proteins having a free N-terminus, since the (poly)peptides/proteins have to be fused at the C-terminus with a phage coat protein. Especially in the case of cDNA libraries, or in the case of proteins requiring a free C-terminus to be functional, it would be highly desirable to have a simple method which doesn't require the generation of C-terminal fusions.

SUMMARY OF THE INVENTION

Thus, the technical problem underlying the present invention is to develop a simple, reliable system which enables the presentation of (poly)peptides/proteins on phage particles without the need to use fusion proteins with phage coat proteins. Additionally, there is a need for a method which allows to recover tightly binding (poly)peptides/proteins in a more reliable way.

The solution to this technical problem is achieved by providing the embodiments characterised in the claims. Accordingly, the present invention allows to easily create and screen large libraries of (poly)peptides/proteins displayed on the surface of bacteriophage particles. The technical approach of the present invention, i.e. linking (poly) peptides/proteins by disulfide bonds to the surface of phage particles, is neither provided nor suggested by the prior art.

Thus, the present invention relates to a method for displaying a (poly)peptide/protein on the surface of a bacteriophage particle comprising:

causing or allowing the attachment of said (poly)peptide/protein after expression to a member of the protein coat of said bacteriophage particle, wherein said attachment is caused by the formation of a disulfide bond between a first cysteine residue comprised in said (poly)peptide/protein and a second cysteine residue comprised in said member of the protein coat.

DETAILED DESCRIPTION OF THE INVENTION

In the context of the present invention, the term "bacteriophage" relates to bacterial viruses forming packages consisting of a protein coat containing nucleic acid required for the replication of the phages. The nucleic acid may be DNA or RNA, either double or single stranded, linear or circular. Bacteriophage such as phage lambda or filamentous phage (such as M13, fd, or fl) are well known to the artisan of ordinary skill in the art. In the context of the present invention, the term "bacteriophage particles" refers to the particles according to the present invention, i.e. to particles displaying a (poly)peptide/protein via a disulfide bonds. During the assembly of bacteriophages, the coat proteins may package different nucleic acid sequences, provided that they comprise a packaging signal. In the context of the present invention, the term "nucleic acid sequences" contained in bacteriophages or bacteriophage particles relates to nucleic acid sequences or vectors having the ability to be packaged by bacteriophage coat proteins during assembly of bacteriophages or bacteriophage particles. Preferably said nucleic acid sequences or vectors are derived from naturally occurring genomes of bacteriophage, and comprise for example, in the case of filamentous phage, phage and phagemid vectors. The latter are plasmids containing a packaging signal and a phage origin of replication in addition to plasmid features.

The term "(poly)peptide" relates to molecules consisting of one or more chains of multiple, i.e. two or more, amino acids linked via peptide bonds.

The term "protein" refers to (poly)peptides where at least part of the (poly)peptide has or is able to acquire a defined three-dimensional arrangement by forming secondary, tertiary, or quaternary structures within and/or between its (poly)peptide chain(s). This definition comprises proteins such as naturally occurring or at least partially artificial proteins, as well as fragments or domains of whole proteins, as long as these fragments or domains are able to acquire a defined three-dimensional arrangement as described above. Examples of (poly)peptides/proteins consisting of one chain are single-chain Fv antibody fragments, and examples for (poly)peptides/proteins consisting of more chains are Fab antibody fragments.

When the first cysteine residue is located at the C-terminus of the (poly)peptide/protein, the display format corresponds to the conventional display set-up with the C-terminus being genetically fused to the member of the phage coat protein. However, by using the N-terminus of the (poly)peptide/protein, the display format can be reverted as in the pJuFO system of Crameri & Suter referred to above.

The term "surface of a bacteriophage particle" refers to the part of a bacteriophage particle which is in contact with the medium the particle is contained in and which is accessible. The surface is determined by the proteins being part of the phage coat (the members of the protein coat of the particle) which is assembled during phage production in appropriate host cells.

The term "after expression" refers to the situation that nucleic acid encoding said (poly)peptide/protein is expressed in a host cell prior to attachment of the (poly)peptide/protein to said coat, in contrast to approaches where nucleic acid encoding fusion proteins with bacteriophage coat proteins are being expressed. The expression of nucleic acid encoding said (poly)peptide/protein and the step of causing or allowing the attachment may be performed in separated steps and/or environments. Preferably, however, expression and the step of causing or allowing the attachment are being performed sequentially in an appropriate host cell. The term "wherein said attachment is caused by the formation of a disulfide bond" refers to a situation, wherein the disulfide bond is responsible for the attachment, and wherein no interaction domain for interaction with a second domain present in the (poly)peptide/protein has been recombinantly fused to said member of the protein coat, as for example in the case of the pJuFo system (Crameri & Suter, 1993).

In a preferred embodiment, the bacteriophage particle displaying the (poly)peptide/protein contains a nucleic acid sequence encoding the (poly)peptide/protein.

Methods for construction of nucleic acid molecules encoding a (poly)peptide/protein according to the present invention, for construction of vectors comprising said nucleic acid molecules, for introduction of said vectors into appropriately chosen host cells, for causing or allowing the expression of said (poly)peptides/proteins are well-known in the art (see, e.g., Sambrook et al., 1989; Ausubel et al., 1999; Ge et al, 1995). Further well-known are methods for the introduction of genetic material required for the generation of progeny bacteriophages or bacteriophage particles in appropriate host cells, and for causing or allowing the generation of said progeny bacteriophages or bacteriophage particles (see, e.g., Kay et al., 1996).

In a further preferred embodiment, the present invention relates to a method, wherein said second cysteine residue is present at a corresponding amino acid position in a wild type coat protein of a bacteriophage.

In a yet further preferred embodiment, the present invention relates to a method, wherein said member of the protein coat is a wild type coat protein of a bacteriophage.

The term "wild type coat protein" refers to those proteins forming the phage coat of naturally occurring bacteriophages. In the case of filamentous bacteriophage, said wild type proteins are gene III protein (pIII), gene VI protein (pVI), gene VII protein (pVII), gene VIII protein (pVIII), and gene IX protein (pIX). The sequences, including the differences between the closely related members of the filamentous bacteriophages such as f1, fd, and M13, are well known to one of ordinary skill in the art (see, e.g., Kay et al., 1996).

In a further preferred embodiment, said member of the protein coat is a truncated variant of a wild type coat protein of a bacteriophage, wherein said truncated variant comprises at least that part of said wild type coat protein causing the incorporation of said coat protein into the protein coat of the bacteriophage particle.

The term "truncated variant" refers to proteins derived from the wild type proteins referred to above which are modified by deletion of at least part of the wild type sequences. This comprises variants such as truncated gene III protein variants which have been found in bacteriophage mutants (Crissman & Smith, 1984) or which have been generated in the course of standard phage display methods (e.g. Bass et al., 1990; Krebber, 1996). For example, said truncated variant may consist, or include, the C-terminal domain of the gene III protein. To identify truncated variants according to the present invention, a detection tag may be fused to the variant, and an assay may be set up to determine whether the variant is incorporated into the phage coat of bacteriophage particles formed in the presence of the variant. By way of truncating a wild type protein by deleting a part of the wild type protein, a cysteine residue may become available which in the wild type protein was forming a disulfide bond with a second cysteine comprised in the deleted part.

In a yet further preferred embodiment, said member of the protein coat is a modified variant of a wild type coat protein of a bacteriophage, wherein said modified variant is capable of being incorporated into the protein coat of the bacteriophage particle.

Methods for achieving modification of a wild type protein according to the present invention are well-known to one of ordinary skill in the art, and involve standard cloning and/or mutagenesis techniques. Methods for the construction of nucleic acid molecules encoding a modified variant of a wild type protein used in a method according to the present invention, for construction of vectors comprising said nucleic acid molecules, including the construction of phage and/or phagemid vectors, for introduction of said vectors into appropriately chosen host cells, for causing or allowing the expression of said modified protein are well-known in the art (see, e.g., Sambrook et al., 1989; Ausubel et al., 1999; Kay et al., 1996). To identify modified variants according to the present invention, a detection tag may be fused to the variant, and an assay may be set up to determine whether the variant is capable or being incorporated into the phage coat of bacteriophage particles formed in the presence of the variant.

In a most preferred embodiment, said second cysteine residue is not present at a corresponding amino acid position in a wild type coat protein of a bacteriophage.

In a preferred embodiment, said second cysteine has been artificially introduced into a wild type coat protein of a bacteriophage.

In the context of the present invention, the term "artificially introduced" refers to a situation where a wild type coat protein has been modified by e.g. recombinant means. For example, nucleic acid encoding a wild type coat protein may be manipulated by standard procedures to introduce a cysteine codon creating a nucleic acid sequence encoding a modified coat protein, wherein a cysteine residue is artificially introduced by insertion into, or addition of said cysteine residue to, said at least part of a wild type or modified coat protein, or by substitution of an amino acid residue comprised in said at least part of a wild type or modified protein by said cysteine residue, or by fusion of said at least part of a wild type or modified coat protein with a (poly)peptide/protein comprising said second cysteine residue, or by any combination of said insertions, additions, substitutions or fusions. Upon expression of the nucleic acid comprising such recombinantly introduced cysteine codon, a variant of the wild type protein is formed comprising a cysteine residue.

In a further most preferred embodiment, said second cysteine has been artificially introduced into a truncated variant of a wild type coat protein of a bacteriophage.

In a yet further preferred embodiment, said second cysteine has been artificially introduced into a modified variant of a wild type coat protein of a bacteriophage.

Methods for achieving the artificial introduction according to the present invention are well-known to one of ordinary skill in the art, and involve standard cloning and/or mutagenesis techniques. Methods for the construction of nucleic acid molecules encoding a modified variant of a wild type protein used in a method according to the present invention, for construction of vectors comprising said nucleic acid molecules, for introduction of said vectors into appropriately chosen host cells, for causing or achieving the expression of said fusion proteins are well-known in the art (see, e.g., Sambrook et al., 1989; Ausubel et al., 1999).

In another embodiment, the present invention relates to a method, wherein said second cysteine is present at, or in the vicinity of, the C-or the N-terminus of said member of the phage coat of said bacteriophage particle.

The term "in the vicinity of" refers to a stretch of up to 15, or more preferably, up to 10 amino acids, counted in both cases from either N-or C-terminus of said (poly)peptide/protein, provided that the N-or C-terminus is located at the outside of the bacteriophage.

Yet further preferred is a method, wherein said bacteriophage is a filamentous bacteriophage. Filamentous bacteriophage such as M13, fd, or f1 are well known to the artisan of ordinary skill in the art.

In the case of filamentous bacteriophage, a method is particularly preferred, wherein said member of the protein coat of the bacteriophage particle is or is derived from the wild type coat protein pIII.

Further preferred is a method, wherein said member of the protein coat of the bacteriophage particle is or is derived from the wild type coat protein pIX. In the context of the present invention, the term "is derived" refers to a modification, wherein the modified protein is capable of being incorporated into the protein coat of the bacteriophage particle. Preferably, those parts of the modified protein corresponding to the wild type protein exhibit an amino acid identity exceeding about 70%, preferably about 80%, most preferably about 90% compared to the corresponding wild type sequence.

In a yet further preferred embodiment of the present invention, the method comprises:

(a) providing a host cell harbouring a nucleic acid sequence comprising a nucleic acid sequence encoding said (poly)peptide/protein;

(b) causing or allowing the expression of said nucleic acid sequence; and (c) causing or allowing the production of bacteriophage particles in said host cell.

In the context of the present invention, the term "causing or allowing the expression" describes cultivating host cells under conditions such that nucleic acid sequence is expressed.

Methods for construction of nucleic acid molecules encoding a (poly)peptide/protein according to to the present invention, for construction of vectors comprising said nucleic acid molecules, for introduction of said vectors into appropriately chosen host cells, for causing or allowing the expression of (poly)peptides/proteins are well-known in the art (see, e.g., Sambrook et al., 1989; Ausubel et al., 1999). Further well-known are methods for the introduction of genetic material required for the generation of progeny bacteriophages or bacteriophage particles in appropriate host cells, and for causing or allowing the generation of said progeny bacteriophages or bacteriophage particles (see, e.g., Kay et al., 1996). The step of causing or allowing the production of bacteriophage particles may require the use of appropriate helper phages, e.g. in the case of working with phagemids.

The steps (b) and (c) may be performed sequentially, in either order, or simultaneously.

In a still further embodiment, said (poly)peptide/protein comprises an immunoglobulin or a functional fragment thereof.

In this context, "immunoglobulin" is used as a synonym for "antibody". The term "functional fragment" refers to a fragment of an immunoglobulin which retains the antigen-binding moiety of an immunoglobulin. Functional immunoglobulin fragments according to the present invention may be Fv (Skerra & Plückthun, 1988), scFv (Bird et al., 1988; Huston et al., 1988), disulfide-linked Fv (Glockshuber et al., 1992; Brinkmann et al., 1993), Fab, F(ab')$_2$ fragments or other fragments well-known to the practitioner skilled in the art, which comprise the variable domain of an immunoglobulin or immunoglobulin fragment.

Particularly preferred is an scFv or Fab fragment.

In a preferred embodiment, the present invention relates to a nucleic acid sequence encoding a modified variant of a wild type coat protein of a bacteriophage, wherein said modified variant consists of:

(a) one or more parts of said wild type coat protein of a bacteriophage, wherein one of said parts comprises at least that part which causes or allows the incorporation of said coat protein into the phage coat; and (b) between one and six additional amino acid residues not present at the corresponding amino acid positions in a wild type coat protein of a bacteriophage, wherein one of said additional amino acid residues is a cysteine residue.

In the context of the present invention, a modified variant obtained by substitution of an amino acid residue in a wild type coat protein sequence by a cysteine residue may be regarded as a variant composed of two parts of said wild type protein linked by an additional cysteine residue. Correspondingly, variants of a wild type coat protein comprising several mutations compared to the wild type sequence may be regarded as being composed of several wild type parts, wherein the individual parts are linked by the mutated residues. However, said variant may also result from the addition of up to six residues, including a cysteine residue, to either C-and or N-terminus of the wild type coat protein.

Further preferred is a nucleic acid sequence encoding a modified variant of a wild type coat protein of a bacteriophage, wherein said modified variant consists of:

(a) one or more parts of said wild type coat protein of a bacteriophage, wherein one of said parts comprises at least that part which causes or allows the incorporation of said coat protein into the phage coat;

(b) between one and six additional amino acid residues not present at the corresponding amino acid positions in a wild type coat protein of a bacteriophage, wherein one of said additional amino acid residues is a cysteine residue; and (c) one or more peptide sequences for purification and/or detection purposes.

Particularly preferred are peptides comprising at least five histidine residues (Hochuli et at., 1988), which are able to bind to metal ions, and can therefore be used for the purification of the protein to which they are fused (Lindner et al., 1992). Also provided for by the invention are additional moieties such as the commonly used c-myc and FLAG tags (Hopp et al., 1988; Knappik & Plückthun, 1994), or the Strep-tag (Schmidt & Skerra, 1994; Schmidt et al., 1996).

The modified variant may further comprise amino acid residues required for cloning, for expression, or protein transport. Amino acid residues required for cloning may include residues encoded by nucleic acid sequences comprising recognition sequences for restriction endonucleases which are incorporated in order to enable the cloning of the nucleic acid sequences into appropriate vectors. Amino acid residues required for expression may include residues leading to increased solubility or stability of the (poly)peptide/protein. Amino acid residues required for protein transport may include signalling sequences responsible for the transport of the modified variant to the periplasm of *E. coli*, and/or amino acid residues facilitating the efficient cleavage of said signalling sequences. Further amino acid residues required for cloning, expression, protein transport, purification and/or detection purposes referred to above are numerous moieties well known to the practitioner skilled in the art.

In another embodiment, the present invention relates to a vector comprising a nucleic acid sequence according to the present invention.

In a preferred embodiment, the vector further comprises one or more nucleic acid sequences encoding a (poly)peptide/protein comprising a second cysteine residue.

In a most preferred embodiment, said (poly)peptide/protein comprises an immunoglobulin or a functional fragment thereof.

In the case of single-chain Fv antibody fragments referred to hereinabove, the vector comprises one nucleic acid sequence encoding the VH and VL domains linked by a (poly)peptide linker, and in the case of Fab antibody fragments, the vector comprises two nucleic acid sequences encoding the VH-CH and the VL-CL chains.

In a further embodiment, the present invention relates to a host cell containing a nucleic acid sequence according to the present invention or a vector according to the present invention.

In the context of the present invention the term "host cell" may be any of a number commonly used in the production of heterologous proteins, including but not limited to bacteria, such as *Escherichia coli* (Ge et al., 1995), or *Bacillus subtilis* (Wu et al., 1993), fungi, such as yeasts (Horwitz et al., 1988; Ridder et al., 1995) or filamentous fungus (Nyyssönen et al., 1993), plant cells (Hiatt & Ma, 1993; Whitelam et al., 1994), insect cells (Potter et al., 1993; Ward et al., 1995), or mammalian cells (Trill et al., 1995).

In a yet further preferred embodiment, the present invention relates to a modified variant of a wild type bacteriophage coat protein encoded by a nucleic acid sequence according to the present invention, a vector according to the present invention or produced by a host cell according to the present invention.

In another embodiment, the present invention relates to a bacteriophage particle displaying a (poly)peptide/protein on its surface obtainable by a method comprising:

causing or allowing the attachment of said (poly)peptide/protein after expression to a member of the protein coat of said bacteriophage particle, wherein said attachment is caused by the formation of a disulfide bond between a first cysteine residue comprised in said (poly)peptide/protein and a second cysteine residue comprised in said member of the protein coat.

In another embodiment, the present invention relates to a bacteriophage particle displaying a (poly)peptide/protein attached to its surface, wherein said attachment is caused by the formation of a disulfide bond between a first cysteine residue comprised in said (poly)peptide/protein and a second cysteine residue comprised in a member of the protein coat of said bacteriophage particle.

In a preferred embodiment, the bacteriophage particle further contains a vector comprising one or more nucleic acid sequences encoding said (poly)peptide/protein.

In a most preferred embodiment of the present invention, the bacteriophage particle contains a vector according to the present invention, wherein said vector comprises a nucleic acid sequence encoding a modified wild type bacteriophage coat protein and furthermore one or more nucleic acid sequences encoding a (poly)peptide/protein and most preferably comprising at least a functional domain of an immunoglobulin.

The preferred embodiments of the method of the present invention referred to hereinabove mutatis mutandis apply to the bacteriophages of the present invention.

In a further embodiment, the present invention relates to a diverse collection of bacteriophage particles according to the present invention, wherein each of said bacteriophage particles displays a (poly)peptide/protein out of a diverse collection of (poly)peptides/proteins.

A "diverse collection of bacteriophage particles" may as well be referred to as a "library" or a "plurality of bacteriophage particles". Each member of such a library displays a distinct member of the library.

In the context of the present invention the term "diverse collection" refers to a collection of at least two particles or molecules which differ in at least part of their compositions, properties, and/or sequences. For example, a diverse collection of (poly)peptides/proteins is a set of (poly)peptides/proteins which differ in at least one amino acid position of their sequence. Such a diverse collection of (poly)peptides/proteins can be obtained in a variety of ways, for example by random mutagenesis of at least one codon of a nucleic acid sequence encoding a starting (poly)peptide/protein, by using error-prone PCR to amplify a nucleic acid sequence encoding a starting (poly)peptide/protein, or by using mutator strains as host cells in a method according to the present invention. These and additional or alternative methods for the generation of diverse collections of (poly)peptides/proteins are well-known to one of ordinary skill in the art.

A "diverse collection of bacteriophage particles" may be referred to as a library or a plurality of bacteriophage particles. Each member of such a library displays a distinct member of the library.

In another embodiment, the invention relates to a method for obtaining a (poly)peptide/protein having a desired property comprising:

(a) providing the diverse collection of bacteriophage particles according to the present invention; and (b) screening said diverse collection and/or selecting from said diverse collection to obtain at least one bacteriophage particle displaying a (poly)peptide/protein having said desired property.

In the context of the present invention the term "desired property" refers to a predetermined property which one of the (poly)peptides/proteins out of the diverse collection of (poly)peptides/proteins should have and which forms the basis for screening and/or selecting the diverse collection. Such properties comprise properties such as binding to a target, blocking of a target, activation of a target-mediated reaction, enzymatic activity, and further properties which are known to one of ordinary skill. Depending on the type of desired property, one of ordinary skill will be able to identify format and necessary steps for performing screening and/or selection.

Most preferred is a method, wherein said desired property is binding to a target of interest.

Said target of interest can be presented to said diverse collection of bacteriophage particles in a variety of ways well known to one of ordinary skill, such as coated on surfaces for solid phase biopanning, linked to particles such as magnetic beads for biopanning in solution, or displayed on the surface of cells for whole cell biopanning or biopanning on tissue sections. Bacteriophage particles having bound to said target can be recovered by a variety of methods well known to one of ordinary skill, such as by elution with appropriate buffers, either by using a pH-or salt gradient, or by specific elution using soluble target.

In a preferred embodiment, the method for obtaining a (poly)peptide/protein further comprises:

(ba) contacting said diverse collection of bacteriophage particles with the target of interest;

(bb) eluting bacteriophage particles not binding to the target of interest;

(bc) eluting bacteriophage particles binding to the target of interest by treating the complexes of target of interest and bacteriophages binding to said target of interest formed in step (ba) under reducing conditions.

Under reducing conditions, such as by incubation with DTT, the disulfide bonds are cleaved, thus allowing to recover the specific bacteriophage particles for further rounds of biopanning and/or for identification of the (poly)peptide/proteins specifically binding to said target.

BRIEF DESCRIPTION OF THE DRAWINGS

FIG. 1*b*: Vector sequence of pMorphX7-hag2-LH (SEQ ID NO:35).

FIG. 2: Vector sequence of pTFT74-N1-hag-HIPM (SEQ ID NO:36)

FIG. 3: Vector sequence of pQE60-MacI (SEQ ID NO:37)

Phages derived from constructs pMorphX7-MacI5-LCH, pMorphX7-MacI5-LHC and pMorphX7-MacI5-LH were produced by standard procedures and pre-incubated in PBSTM either with 5 mM DTT (+DTT) or without DTT. 5 μg/well of specific antigen (MacI, dark columns) as well as unspecific control antigen (BSA, light columns) were coated onto Maxisorp Nunc-Immuno microtiter plates and incubated with $1\times10^{10}$ phages/well, respectively. Bound phages were detected via anti-M13-HRP conjugate and BM blue soluble substrate. Phages derived from conventional phage display vector pMorph13-MacI5 were used as control ($3\times10^7$ phages/well). Experimental details are given in Example 1.

Figure 5:
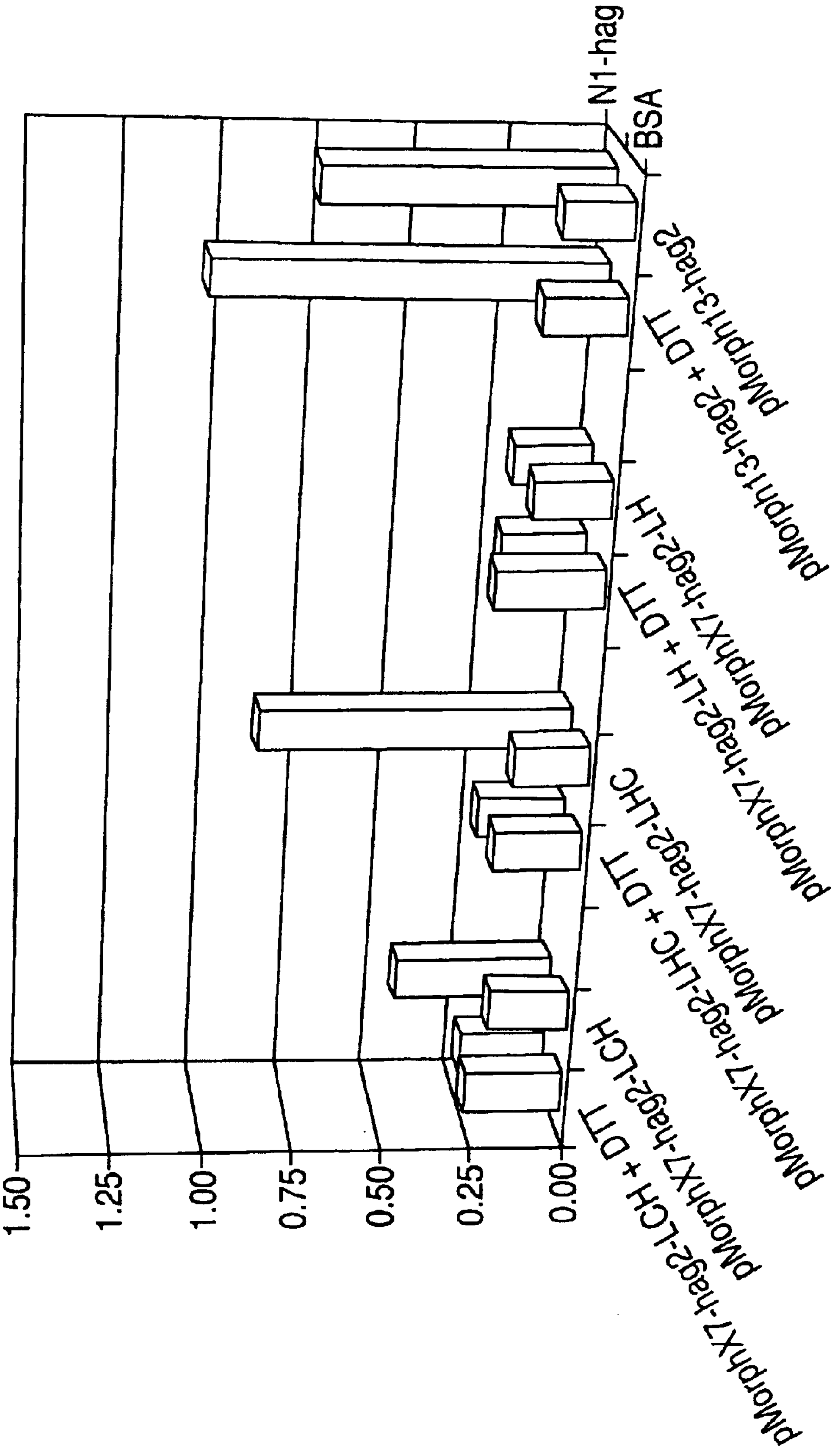

FIG. 5: Specific binding of scFv displayed on non-engineered phages.

Phages derived from constructs pMorphX7-hag2-LCH, pMorphX7-hag2-LHC and pMorphX7-hag2-LH were produced by standard procedures and pre-incubated in PBSTM either with 5 mM DTT (+DTT) or without DTT. 5 μg/well of specific antigen (N1-hag, dark columns) as well as unspecific control antigen (BSA, light columns) were coated onto Maxisorp Nunc-Immuno microtiter plates and incubated with $1\times10^{10}$ phages/well, respectively. Bound phages were detected via anti-M13-FIRP conjugate and BM blue soluble substrate. Phages derived from conventional phage display vector pMorph13-hag2 were used as control ($3\times10^7$ phages/well). Experimental details are given in Example 1.

Figure 6A:
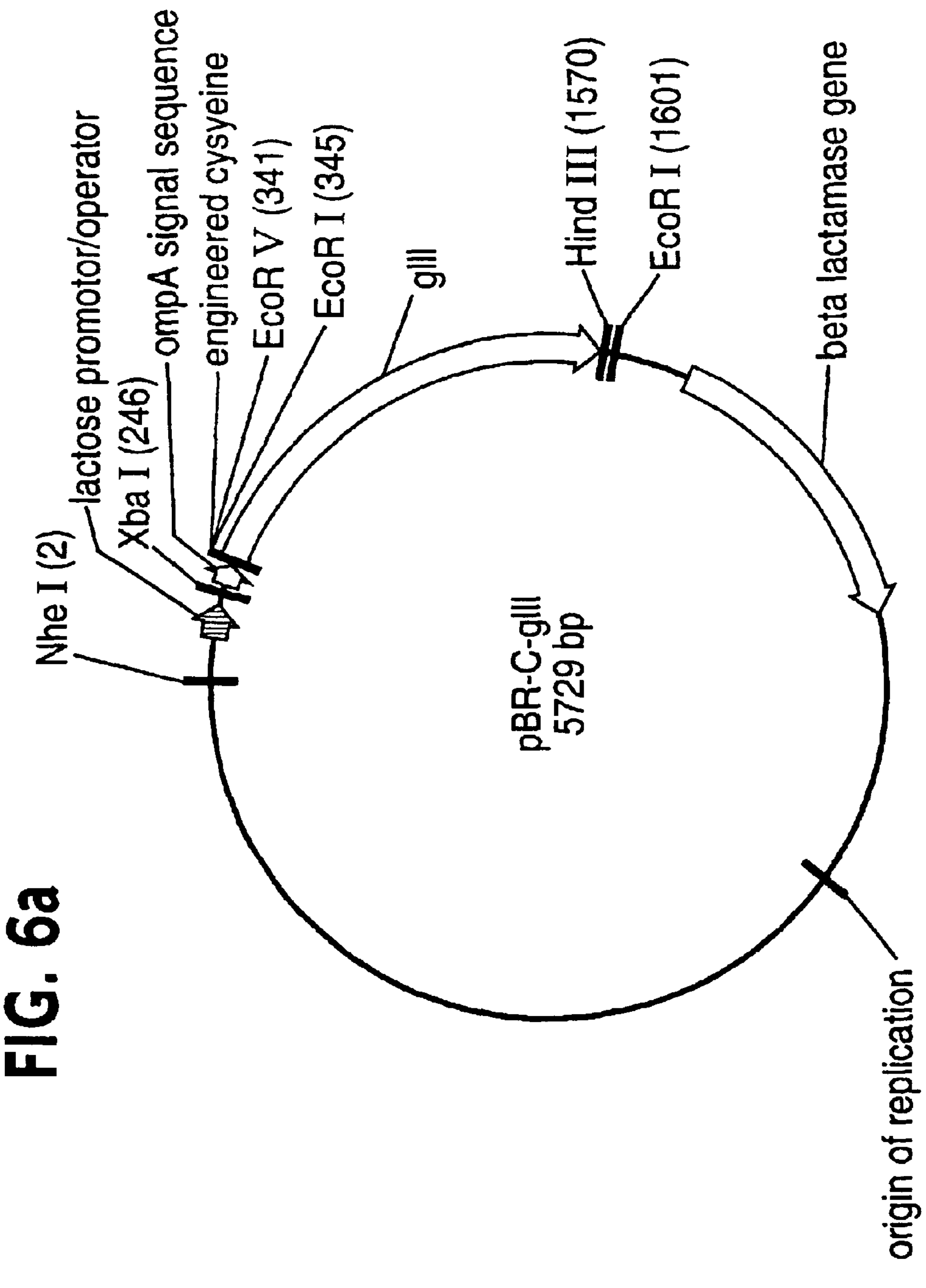

FIG. 6*a*: Vector map of construct pBR-C-gIII.

FIG. 6*b*: Sequence of expression cassette for full length pIII with an N-terminal cysteine residue (C-gm) (SEQ ID NO:38).

FIG. 6*c*: Sequence of expression cassette for truncated pill with an N-terminal cysteine residue (C-gIIICT) (SEQ ID NO:39).

Figure 7A:
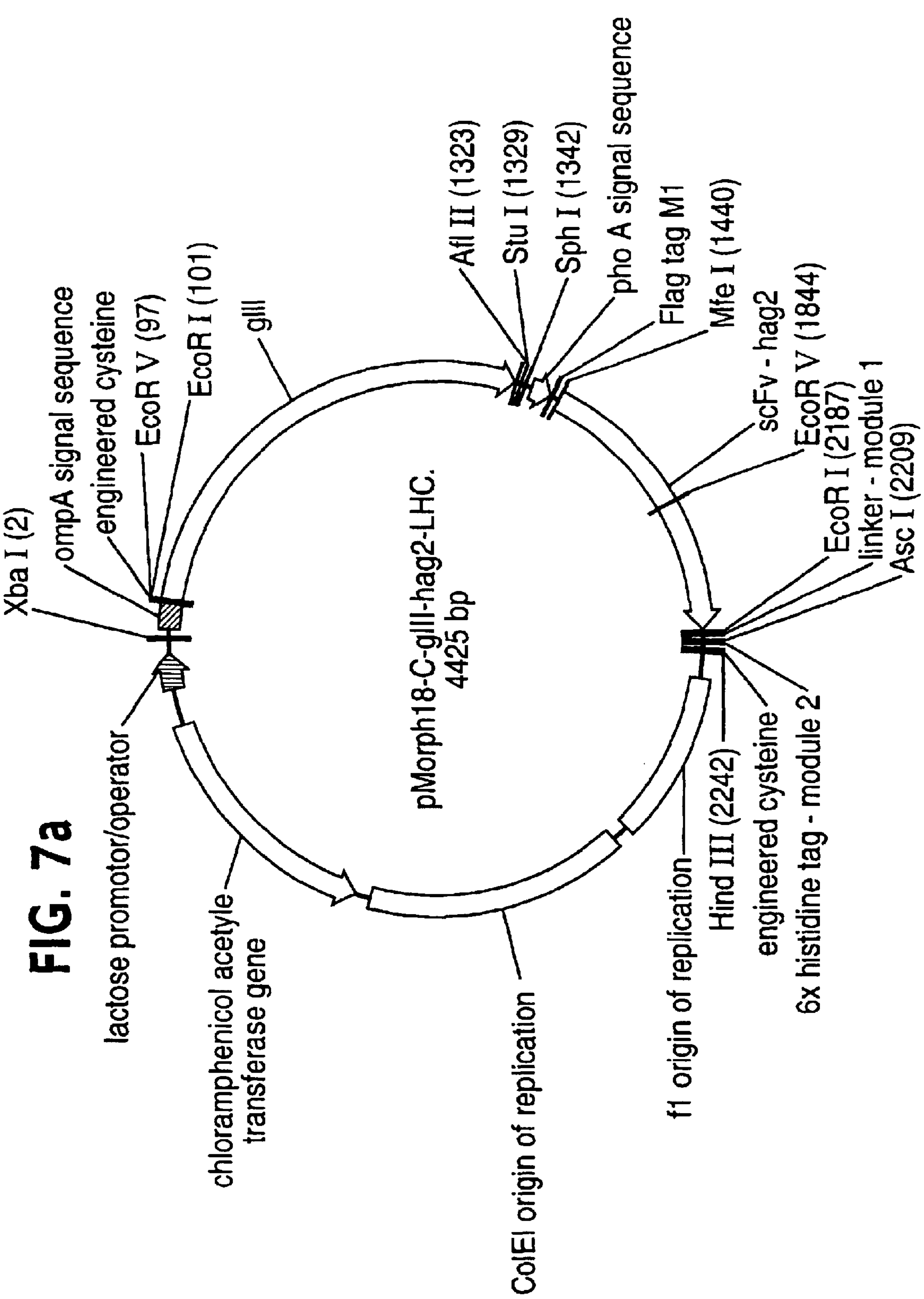

FIG. 7*a*: Vector map of construct pMorph18-C-gIII-hag2-LHC.

FIG. 7*b*: Vector sequence of pMorph18-C-gIII-hag2-LHC (SEQ ID NO:40).

FIG. 8: Detection of scFv MacI-5 displayed on engineered phages—Two-vector system.

Phages derived from constructs pMorphX7-MacI-5-LH/pBR-C-gIII (lanes 1 & 5), pMorphX7-MacI-5-LHC/pBR-C-gIII (lanes 2 & 6), pMorphX7-MacI-5-LHC (lanes 3 & 7) and pMorphX7-MacI-5-LH (lanes 4 & 8) were produced by standard procedures. 1 . 5×$10^{10}$ phages were pre-incubated in PBS with DTT (lanes 1–4) or without DTT (lanes 5–8). SDS loading buffer lacking reducing agents was added, phages were applied to an 4–15% SDS PAA Ready gel and analysed in immunoblots. Detection of scFvs associated with phages was done via anti-FLAG Ml antibody, anti-mouse-IgG-AP conjugate and Fast BCTP/NPT substrate (6A) and via anti-pill antibody, anti-mouse-IgG-AP conjugate and Fast BCIP/NPT substrate (6B). Low range marker (Amersham #RPN756) is marked as M. Experimental details are given in Example 2.1.

FIG. 9: Detection of scFvs Displayed on Engineered Phages—One-vector system.

Phages derived from constructs pMorph18-C-gIII-hag2-LHC (lanes 1–8; 7A), pMorph18-C-gIII-AB1.1-LHC (lanes 1, 2, 5 and 6; 7B) and pMorph18-C-gIII-MacI-5-LHC (lanes 3, 4, 7 and 8; 7B) were produced by standard procedures. 1–5×$10^{10}$ phages were pre-incubated in PBS with DTT (lanes 1, 2, 5 and 6; 7A and lanes 1–4; 7B) or without DTT (lanes 3, 4, 7 and 8; 7A and lanes 5–8; 7B). SDS loading buffer lacking reducing agents was added, phages were applied to an 4–15% SDS PAA Ready gel and analysed in immunoblots. Detection of scFvs associated with phages was done via anti-FLAG M1 antibody, anti-mouse-IgG-AP conjugate and Fast BCIP/NPT substrate (lanes 1–4; 7A) and via anti-pill antibody, anti-mouse-IgG-AP conjugate and Fast BCIP/NPT substrate (lanes 5–8; 7A and lanes 1–8; 7B). Low range marker (Amersham #RPN756) is marked as M, Experimental details are given in Example 2.1.

Figure 10:
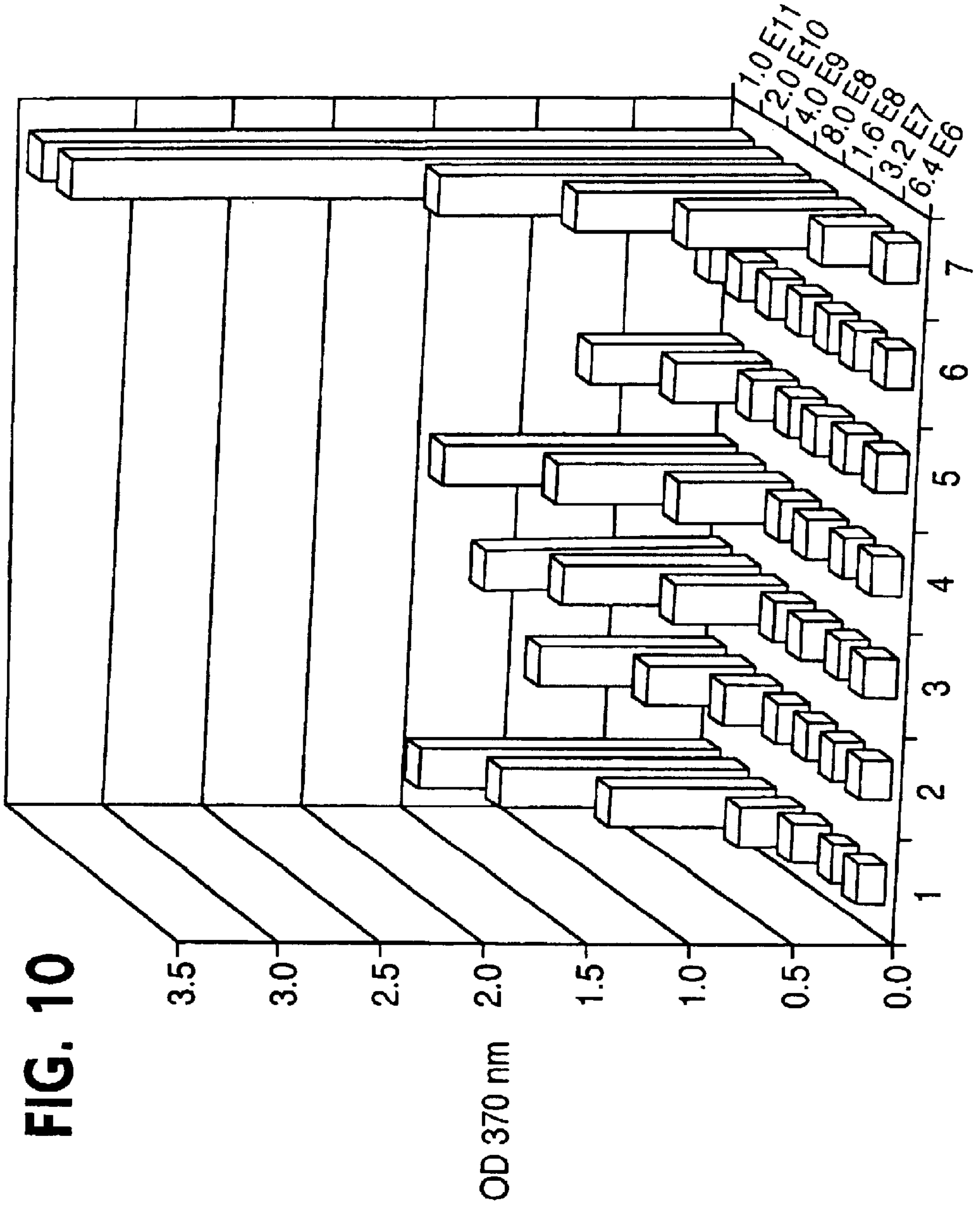

FIG. 10: Specific binding of scFv displayed on engineered phages—Comparison of the different two-vector systems Phages derived from constructs pMorphX7-MacI-5-LHC/pBR-C-gIII (1), pMorphX7-MacI-5-LHC/pBR-C-gIIICT (2), pMorphX7-MacI-5-LHC/pUC-C-gIII (3), pMorphX7-MacI-5-LHC/pUC-C-gIIICT (4), pMorphX7-MacI-5-LHC (5), pMorphX7-MacI-5-LH (6) and the conventional phage display vector pMorph13-MacI-5 (7) were produced by standard procedures. 5 $\mu$g of specific antigen (MacI) as well as unspecific control antigen (BSA, data not shown) were coated onto Maxisorp Nunc-Immuno microtiter plates and incubated with a range of 6.4×$10^{6}$ and 1×$10^{11}$ phages per well. Bound phages were detected via anti-M13-HRP conjugate and BM blue substrate. Experimental details are given in Example 2.1

Figure 11:
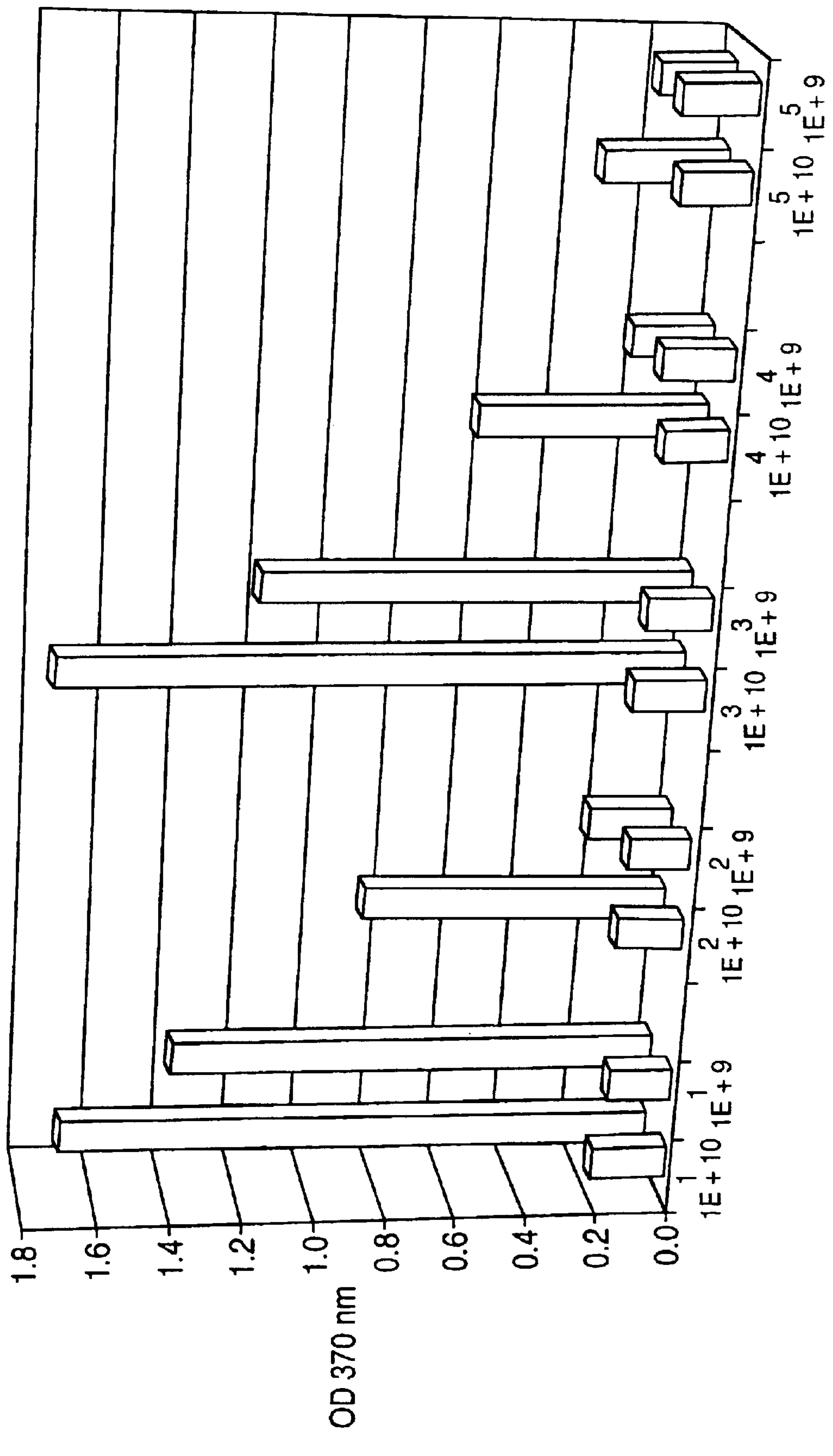

FIG. 11: Specific binding of scFv displayed on engineered phages—Comparison of the one- and two-vector system Phages derived from constructs pMorphX7-MacI-5-LHC/pBR-C-gIII (1), pMorphX7-MacI-5-LHC/pBR-C-gIIICT (2), pMorph18-C-gIII-MacI-5-LHC (3), pMorph18-C-gIIICT-MacI-5-LHC (4) and pMorphX7-MacI-5-LHC (5) were produced by standard procedures. 5 $\mu$g of specific antigen (MacI, dark columns) as well as unspecific control antigen (BSA, light columns) were coated onto Maxisorp Nunc-Immuno microtiter plates and incubated with 1×$10^{10}$ and 1×$10^{9}$ phages, respectively. Bound phages were detected via anti-M13-HRP conjugate and BM blue substrate. Experimental details are given in Example 2.1.

Figure 12:
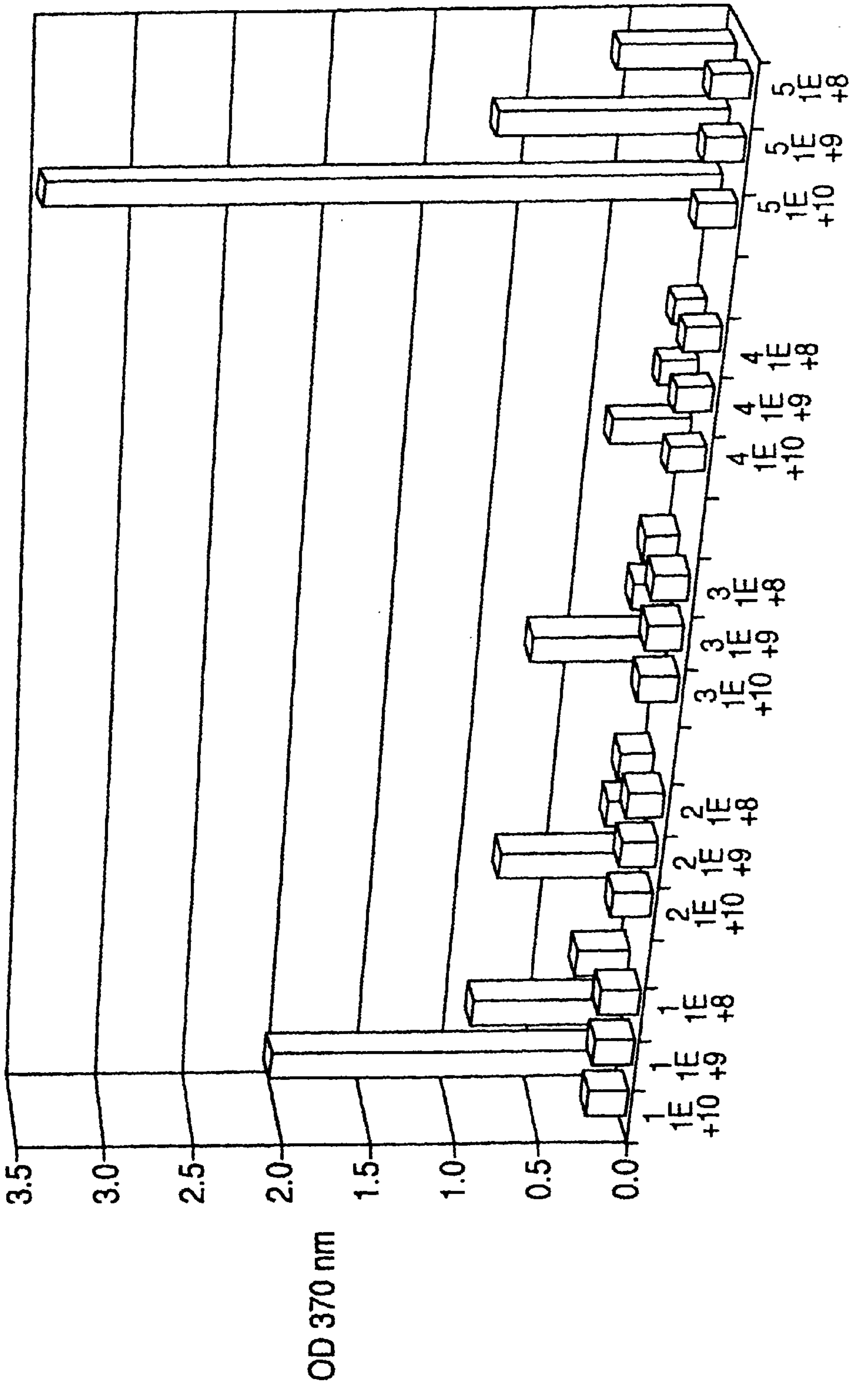

FIG. 12: Specific binding of scFv displayed on engineered phages—Comparison of engineered gene III and gene IX proteins in the one-vector system Phages derived from constructs pMorph18-C-gIII-MacI-5-LHC (1), pMorph18-C-gIIICT-MacI-5-LHC (2), pMorph18-C-gIX-MacI-5-LHC (3), pMorphX7-MacI-5-LHC (4) and the conventional phage display vector pMorph13-MacI-5 (5) were produced by standard procedures. 5 $\mu$g of specific antigen (MacI, dark columns) as well as unspecific control antigen (BSA, light columns) were coated onto Maxisorp Nunc-Immuno microtiter plates and incubated with 1×$10^{10}$, 1×$10^{9}$ and 1×$10^{8}$ phages, respectively. Bound phages were detected via anti-M13-HRP conjugate and BM blue substrate. Experimental details are given in Example 2.1.

Figure 13:
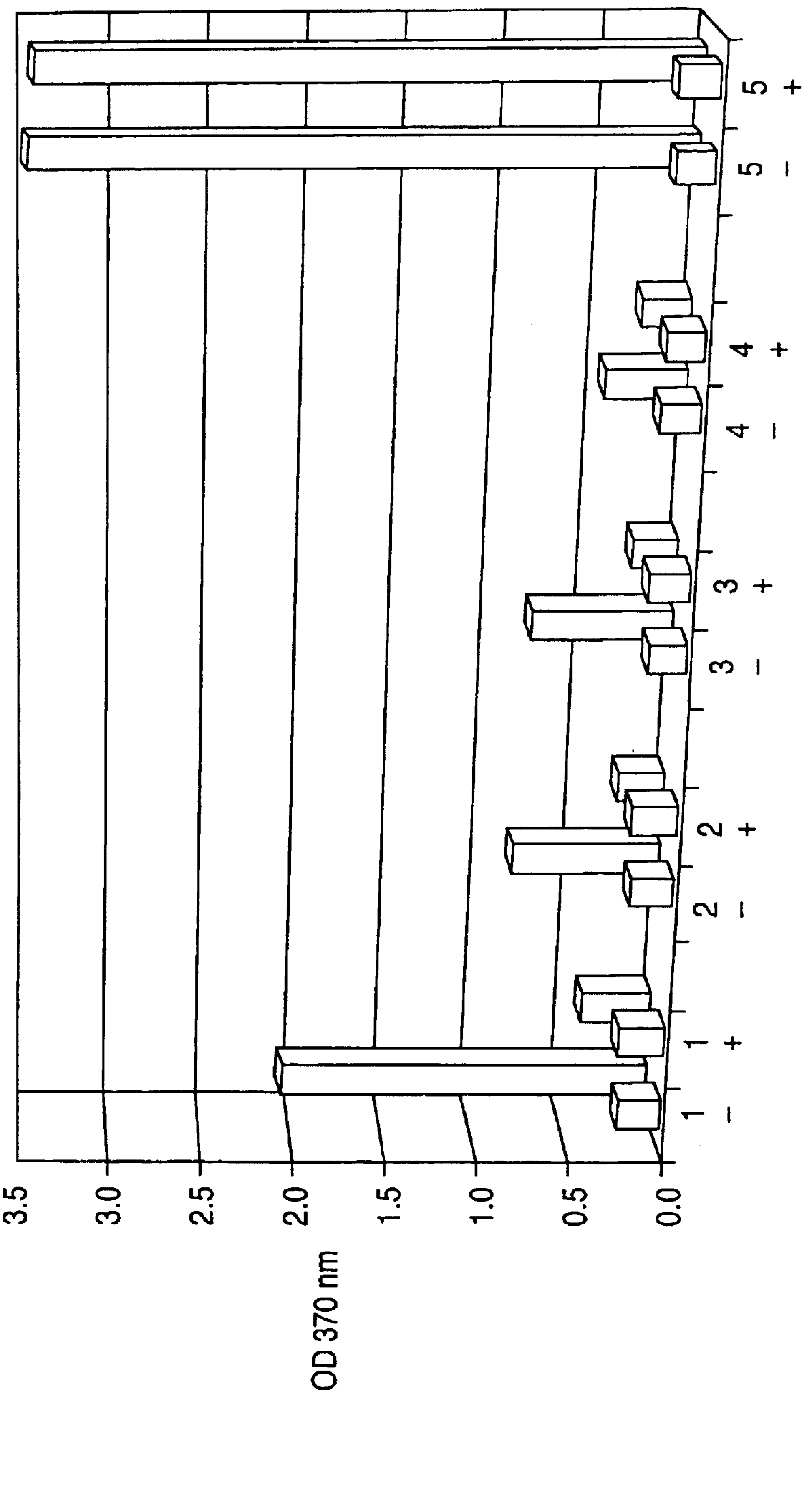

FIG. 13: Specific binding of scFv displayed on engineered phages—Impact of DTT.

Phages derived from constructs pMorph18-C-gJII-MacJ-5-LHC (1), pMorph18-C-gIIICT-MacI-5-LHC (2), pMorph18-C-gIX-MacI-5-LHC (3), pMorphX7-MacI-5-LHC (4) and the conventional phage display vector pMorph13-MacI-5 (5) were produced by standard procedures and pre-incubated in PBSTM either with 5 mM DTT (+) or without DTT (−). 5 $\mu$g of specific antigen (MacI, dark columns) as well as unspecific control antigen (B SA, light columns) were coated onto Maxisorp Nunc-Immuno microtiter plates and incubated with 1×$10^{10}$ phages respectively. Bound phages were detected via anti-M13-HRP conjugate and BM blue substrate. Experimental details are given in Example 2.1.

Figure 14:
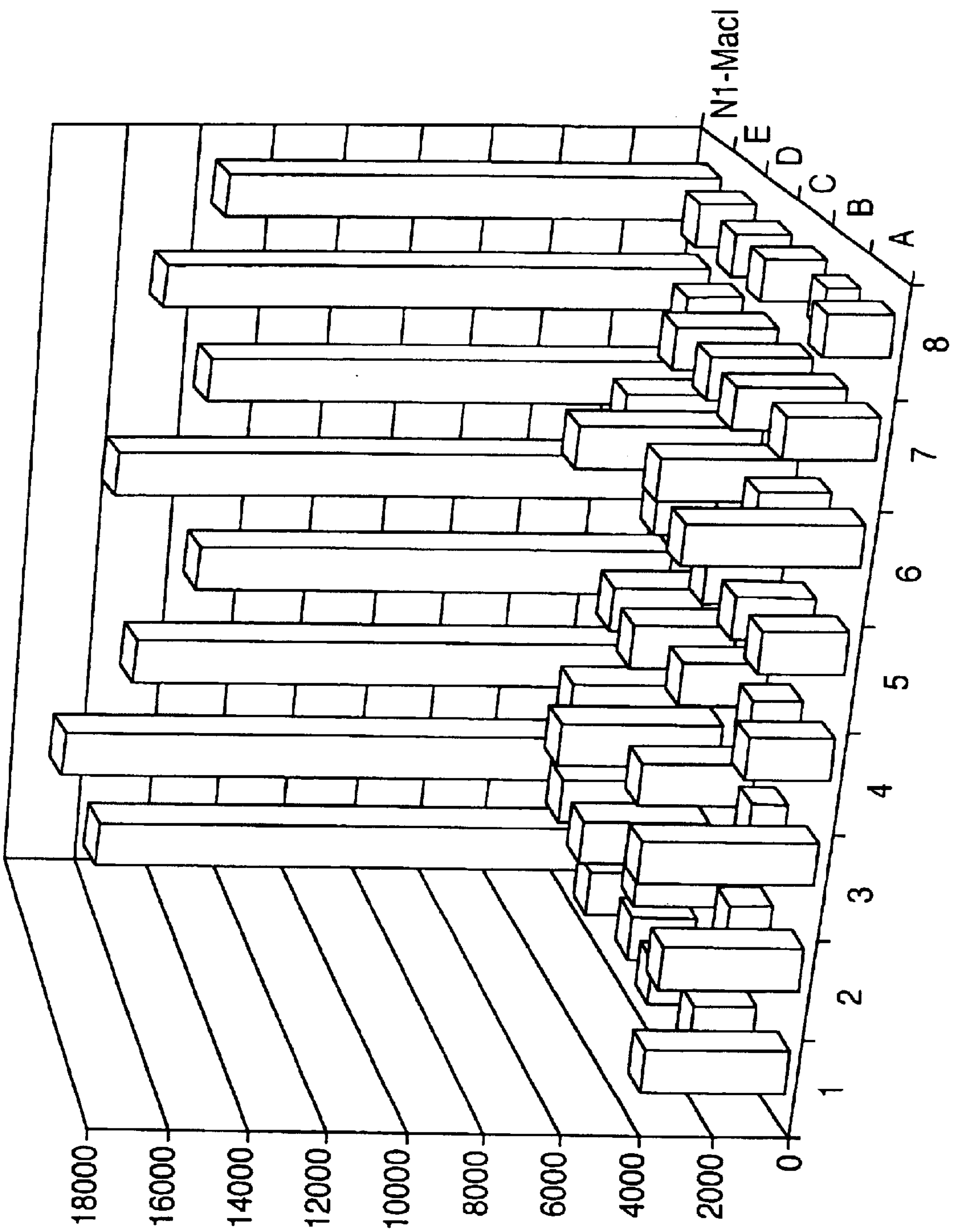

FIG. 14: Specificity of selected scFvs—Panning of preselected pools against N1-MacI.

scFvs selected after two rounds of cys-display panning against antigen N1-MacI from the κ-chain (1–5) and the λ-chain pool (6–8) were expressed according to standard procedures. 0.1 $\mu$g/well of milk powder (A), BSA (B), FITC-BSA (C, FJTC coupled to BSA), N1-hag (D), N1-Np50 (E) and N1-MacI (N1-MacI) was coated onto 384 well plates (Maxisorp; Nunc) and incubated with 10 $\mu$l scFv solution, respectively. Bound scFvs were detected via a mixture of anti-Flag M1, anti-Flag M2 and anti-mouse IgG-AP conjugate as well as AttoPhos fluorescence substrate (Roche #1484281). Each scFv was tested in quadruplicates and mean values are presented.

Figure 15:
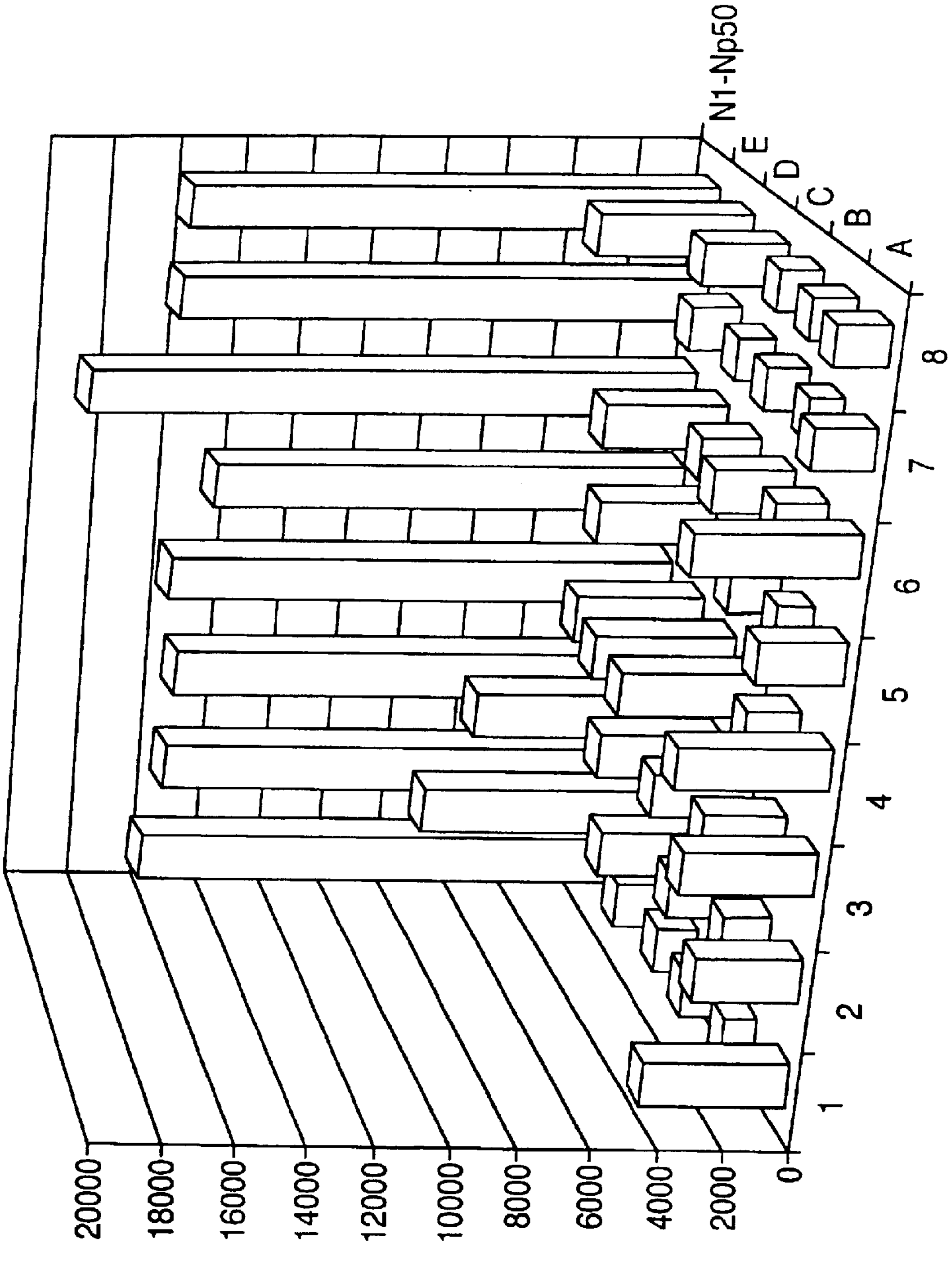

FIG. 15: Specificity of selected scFvs—Panning of preselected pools against N1-Np50.

scFvs selected after two rounds of cys-display panning against antigen N1-Np50 (1–8) were expressed according to standard procedures. 0.1 $\mu$g/well of milk powder (A), BSA (B), FITC-BSA (C, FITC coupled to BSA), N1-hag (D), N1-MacI (E) and N1-Np50 (N1-Np50) was coated onto 384 well plates (Maxisorp; Nunc) and incubated with 10 $\mu$l scFv solution, respectively. Bound scFvs were detected via a mixture of anti-Flag M1, anti-Flag M2 and anti-mouse IgG-AP conjugate as well as AttoPhos fluorescence substrate (Roche #1484281). Each scFv was tested in quadruplicates and mean values are presented.

Figure 16A:
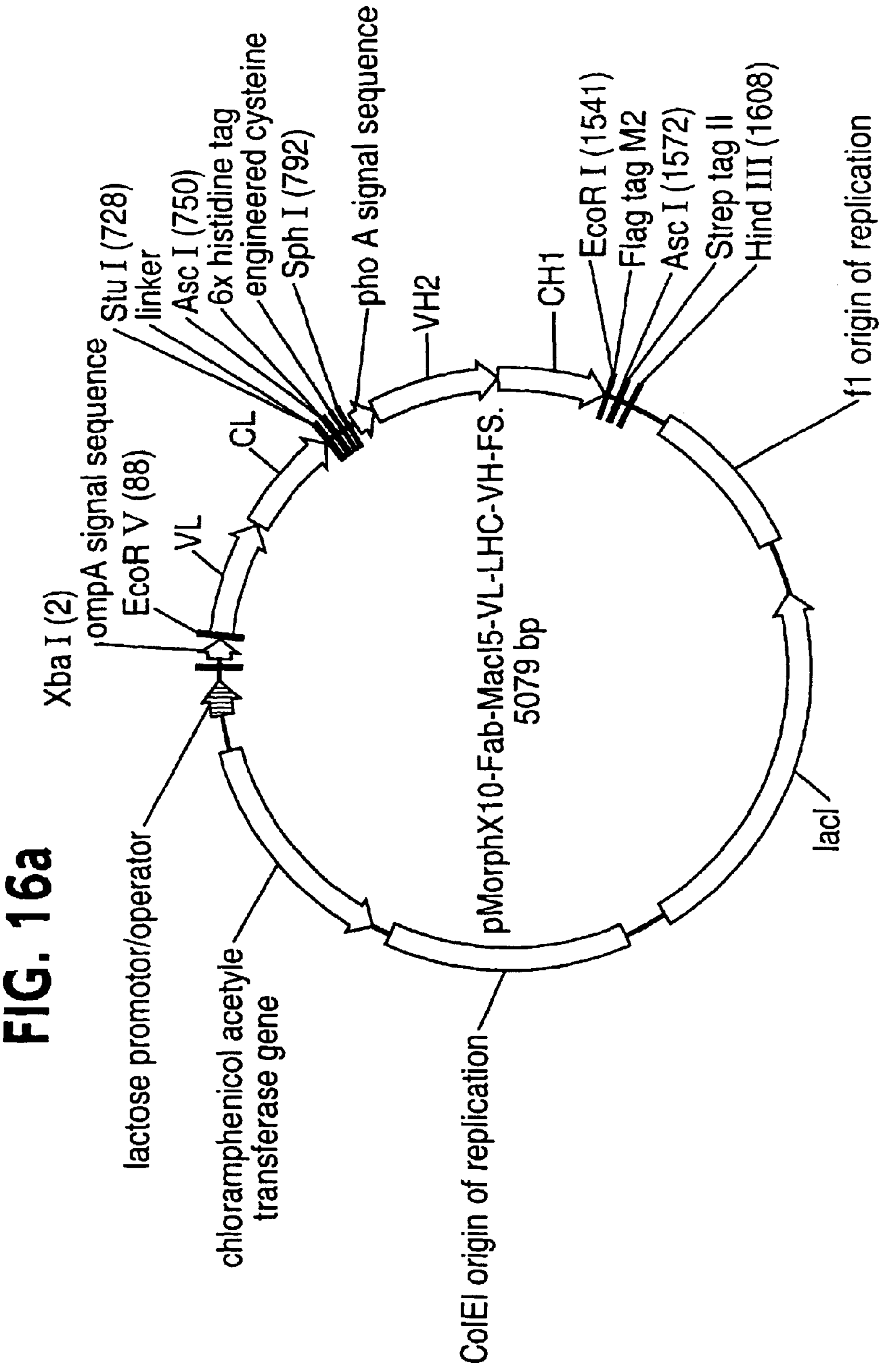

FIG. 16*a*: Vector map of construct pMorphX10-Fab-MacI5-VL-LHC-VH-FS.

FIG. 16*b*: Complete vector sequence of pMorphX10-Fab-MacI5-VL-LHC-VH-FS (SEQ NO:41).

Figure 17:
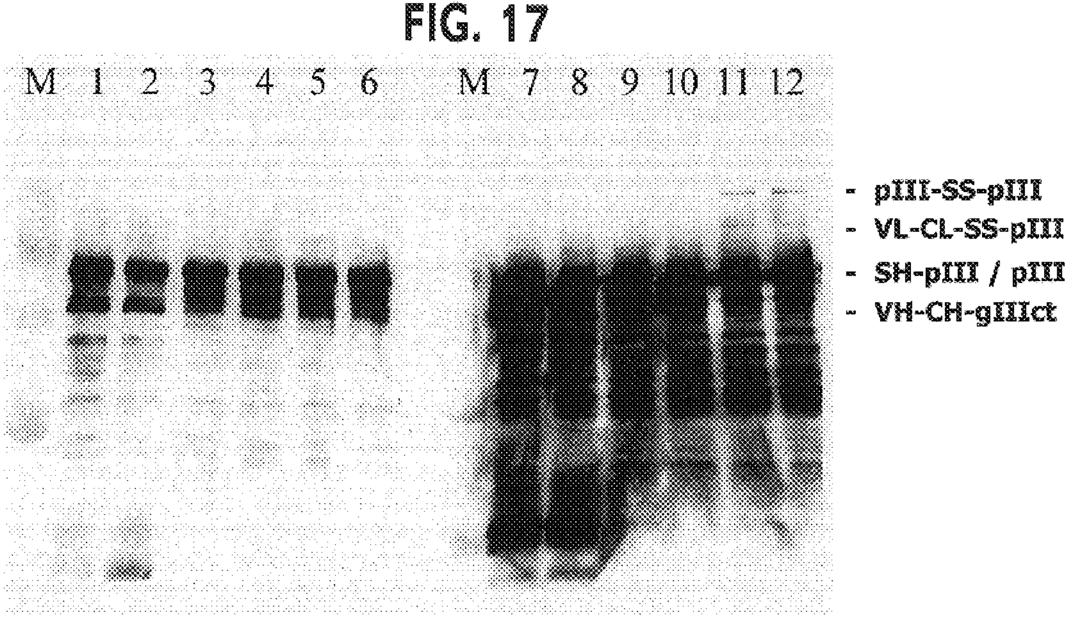

FIG. 17: Detection of Fab ICAM1-C8 displayed on engineered phages

Phages derived from constructs pMorphX10-Fab-ICAM1C8-VL-LHC-VH-MS/pBAD-SS-C-gIII (lanes 5, 6, 11, 12), pMorphX10-Fab-ICAM1C8-VL-LHC-VH-MS (lanes 3, 4, 9, 10) and pMorph18-Fab-ICAM1C8 (lanes 1, 2, 7, 8) were produced by standard procedures. $1\times10^{10}$ phages were pre-incubated in PBS with DTT (lanes 1–6) or without DTT (lanes 7–12). SDS loading buffer lacking reducing agents was added, phages were applied to an 12% SDS PAA Ready gel and analysed in immunoblots. Detection was done via anti-pIII antibody, anti-mouse-IgG-HRP conjugate and BM Blue POD precipitating substrate. Low range molecular weight marker (Amersham Life Science #RPN756) is marked as M. Experimental details are given in Example 2.2.

Figure 18:
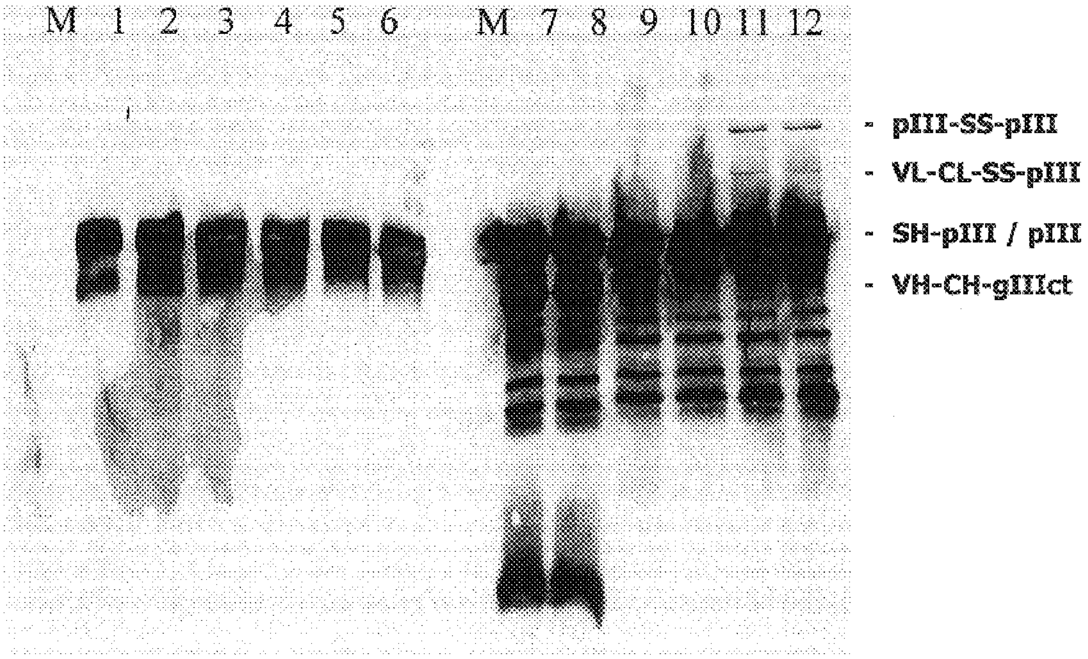

FIG. 18: Detection of Fab MacI-A8 displayed on engineered phages.

Phages derived from constructs pMorphX10-Fab-MacIA8-VL-LHC-VH-FS/pBAD-SS-C-gIII (lanes 5, 6, 11, 12), pMorphX10-Fab-MacIA8-VL-LHC-VH-FS (lanes 3, 4, 9, 10) and pMorph18-Fab-MacIA8 (lanes 1, 2, 7, 8) were produced by standard procedures. $1\times10^{10}$ phages were pre-incubated in PBS with DTT (lanes 1–6) or without DTT (lanes 7–12). SDS loading buffer lacking reducing agents was added, phages were applied to an 12% SDS PAA Ready gel and analysed in immunoblots. Detection was done via anti-pIII antibody, anti-mouse-IgG-HRP conjugate and BM Blue precipitating substrate. Low range molecular weight marker (Amersham Life Science #RPN756) is marked as M. Experimental details are given in Example 2.2.

Figure 19:
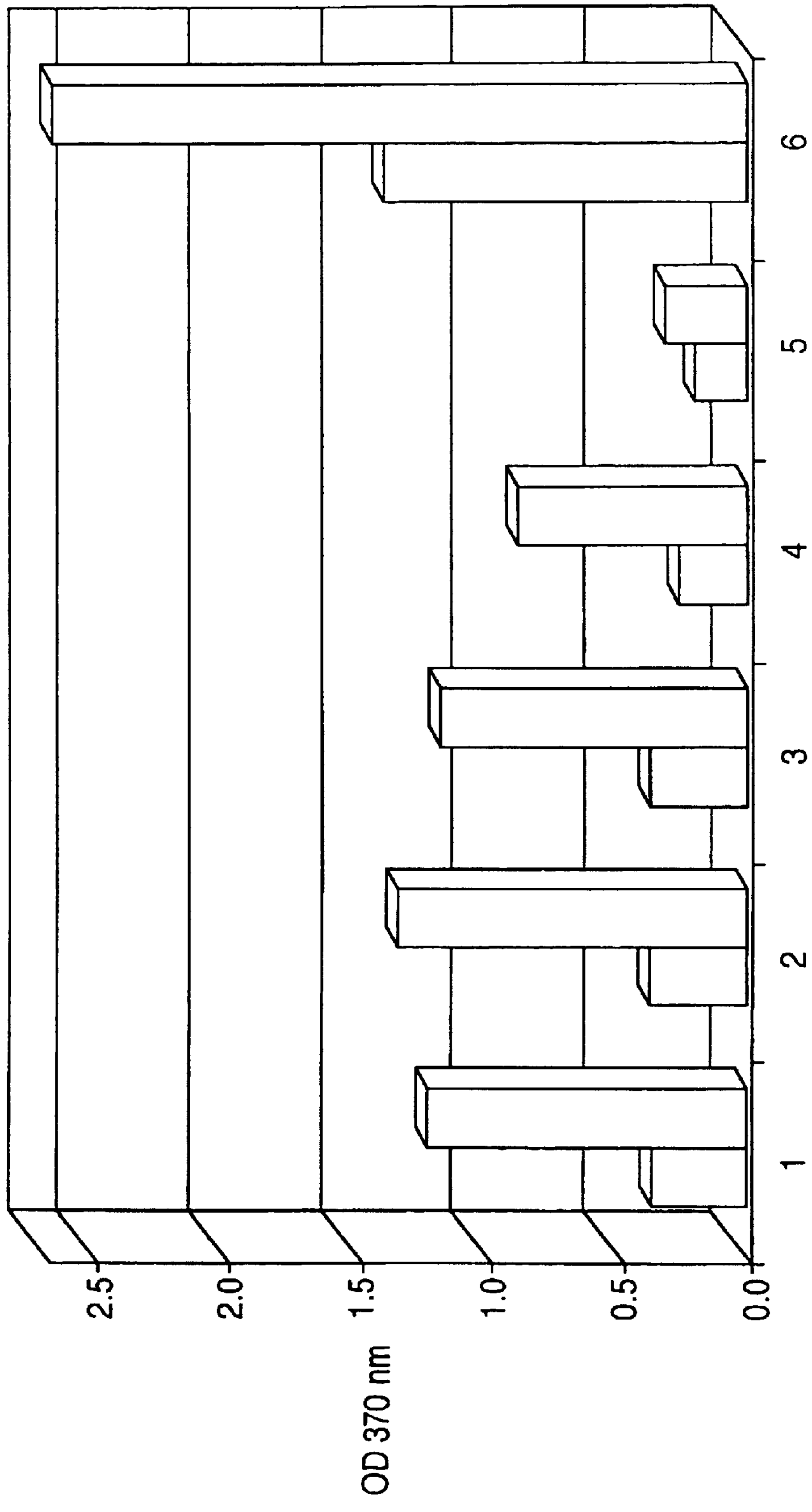

FIG. 19: Specific binding of Fabs displayed on engineered phages—Fab MacI-5.

Phages derived from constructs pMorphX10-Fab-MacI5-VL-LHC-VH-FS/pBR-C-gIII (1), pMorphX10-Fab-MacI5-VL-C-VH-FS/pBR-C-gIII (2), pMorphX10-Fab-MacI5-VL-VH-CFS/pBR-C-gIII (3), pMorphX10-Fab-MacI5-VL-VH-LHC/pBR-C-gIII (4), pMorphX9-Fab-MacI5-FS (5), and the conventional phage display vector pMorph18-Fab-MacI5 (6) were produced by standard procedures. 5 $\mu$g/well of specific antigen (N1-MacI) were coated onto Maxisorp Nunc-Immuno microtiter plates and incubated with $1\times10^8$ (light columns) and $1\times10^9$ (dark columns) phages per well. Bound phages were detected via anti-M13-HRP conjugate and BM blue soluble substrate. Each column represents the mean value of three independent phage preparations tested in duplicates. Experimental details are given in Example 2.2.

Figure 20:
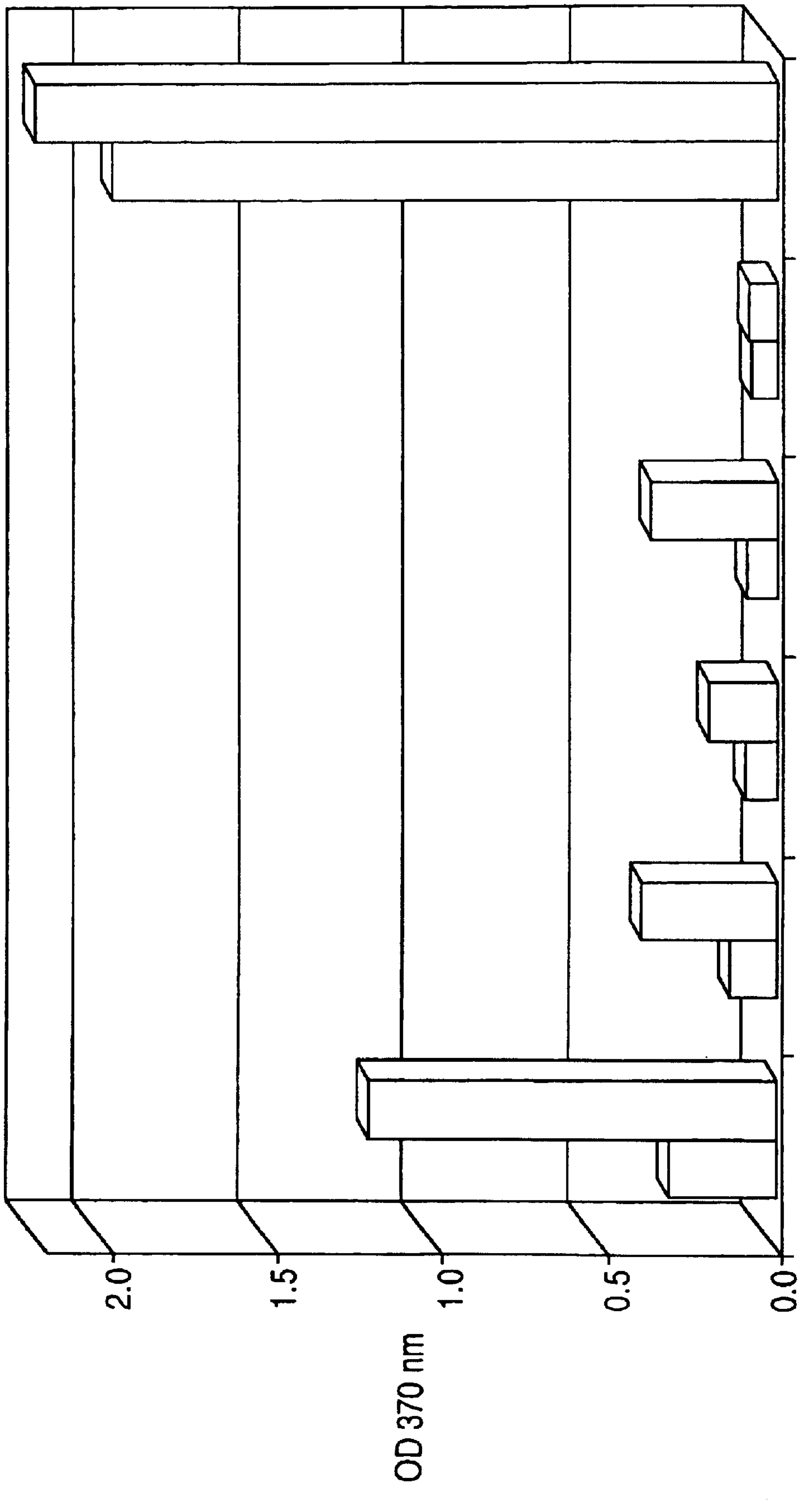

FIG. 20: Specific binding of Fabs displayed on engineered phages—Fab MacI-A8.

Phages derived from constructs pMorphX10-Fab-MacIA8-VL-LHC-VH-FS/pBR-C-gIII (1), pMorphX10-Fab-MacIA8-VL-C-VH-FS/pBR-C-gIII (2), pMorphX10-Fab-MacIA8-VL-VH-CFS/pBR-C-gIII (3), pMorphX10-Fab-MacIA8-VL-VH-LHC/pBR-C-gIII (4), pMorphX9-Fab-MacIA8-FS (5), and the conventional phage display vector pMorph18-Fab-MacIA8 (6) were produced by standard procedures. 5 $\mu$g/well of specific antigen (N1-MacI) were coated onto Maxisorp Nunc-Immuno microtiter plates and incubated with $1\times10^9$ (light columns) and $1\times10^{10}$ (dark columns) phages per well. Bound phages were detected via anti-M13-HRP conjugate and BM blue soluble substrate. Each column represents the mean value of three independent phage preparations tested in duplicates. Experimental details are given in Example 2.2.

Figure 21:
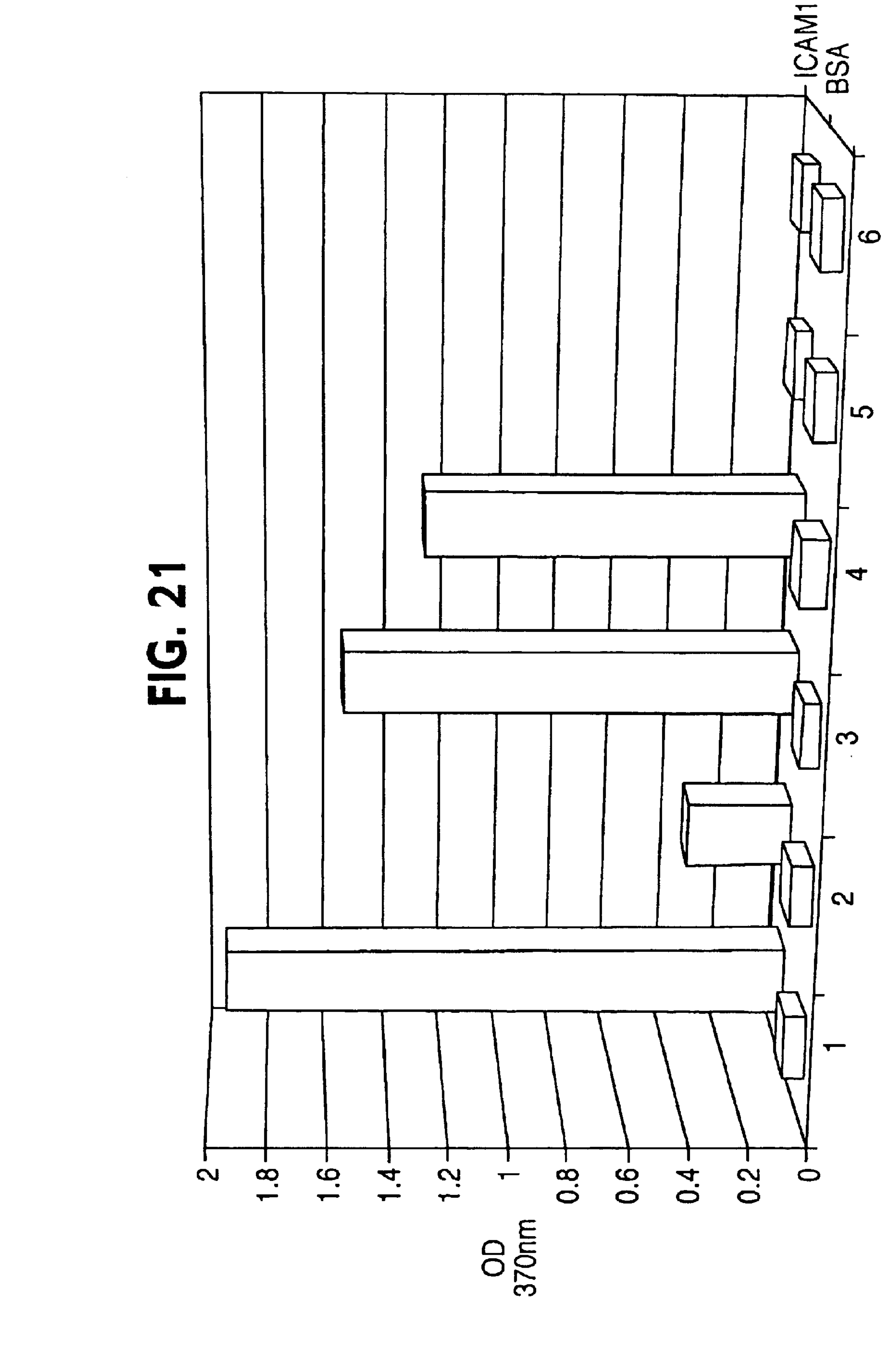

FIG. 21: Specific binding of Fabs displayed on engineered phages—Fab ICAM1-C8.

Phages derived from constructs pMorphX10-Fab-ICAM1C8-VL-LHC-VH-MS/pBR-C-gIII (1), pMorphX10-Fab-ICAM1C8-VL-C-VH-MS/pBR-C-gIII (2), pMorphX10-Fab-ICAM1C8-VL-VH-CMS/pBR-C-gIII (3), pMorphX10-Fab-ICAM1C8-VL-VH-LHC/pBR-C-gIII (4), pMorphX9-Fab-ICAM1C8-MS (5), pMorphX9-Fab-ICAM1C8-MS/pBR-C-gIII (6) were produced by standard procedures. 5 $\mu$g/well of specific antigen (ICAM1, dark columns) or unspecific antigen (BSA, light columns) were coated onto Maxisorp Nunc-Immuno microtiter plates and incubated with $1\times10^9$ phages per well. Bound phages were detected via anti-M13-HRP conjugate and BM blue soluble substrate. Each column represents the mean value of one phage preparation tested in duplicates. Experimental details are given in Example 2.2.

Figure 22:
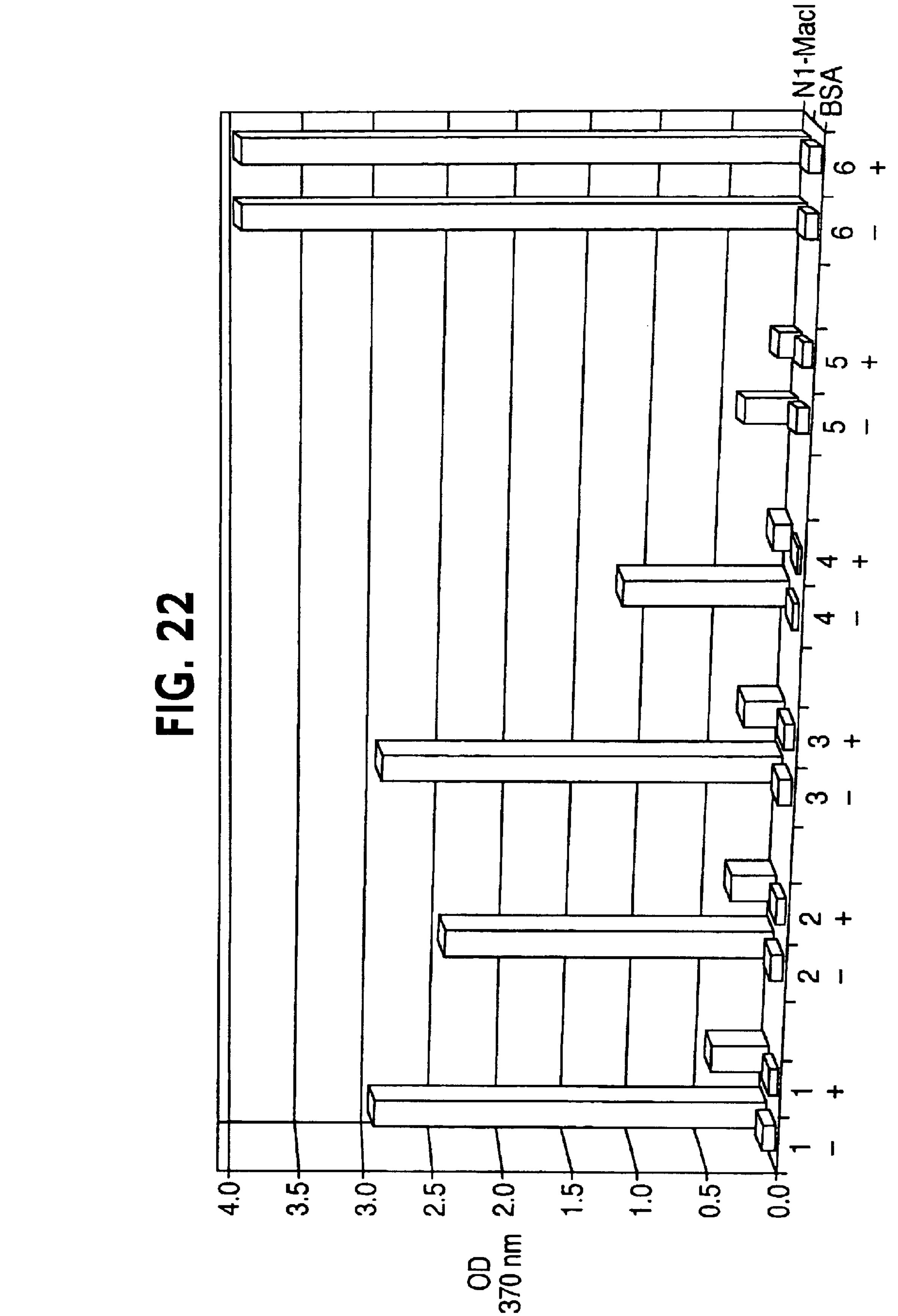

FIG. 22: Specific binding of Fabs displayed on engineered phages—Impact of DTT.

Phages derived from constructs pMorphX10-Fab-MacI5-VL-LHC-VH-FS/pBR-C-gIII (1), pMorphX10-Fab-MacI5-VL-C-VH-FS/pBR-C-gIII (2), pMorphX10-Fab-MacI5-VL-VH-CFS/pBR-C-gIII (3), pMorphX10-Fab-MacI5-VL-VH-LHC/pBR-C-gIII (4), pMorphX9-Fab-MacI5-FS (5), and the conventional phage display vector pMorph18-Fab-MacI5 (6) were produced by standard procedures and pre-incubated in PBSTM either with 10 MM DTT (+) or without DTT (–). 5 $\mu$g/well of specific antigen (N1-MacI, dark columns) as well as unspecific control antigen (BSA, light columns) were coated onto Maxisorp Nunc-Immuno microtiter plates and incubated with $1\times10^9$ phages respectively. Bound phages were detected via anti-M13-HRP conjugate and BM blue substrate. Each column represents the mean value of one phage preparation tested in duplicates. Experimental details are given in Example 2.2.

The examples illustrate the invention.

EXAMPLE 1

Display of (Poly)Peptides/Proteins on the Surface of Non-Engineered Filamentous Bacteriophage Particles Via Formation of Disulfide Bonds In the following example, all molecular biology experiments are performed according to standard protocols (Ausubel et al., 1999).

Construction of Vectors Expressing scFvs

Figure 1A:
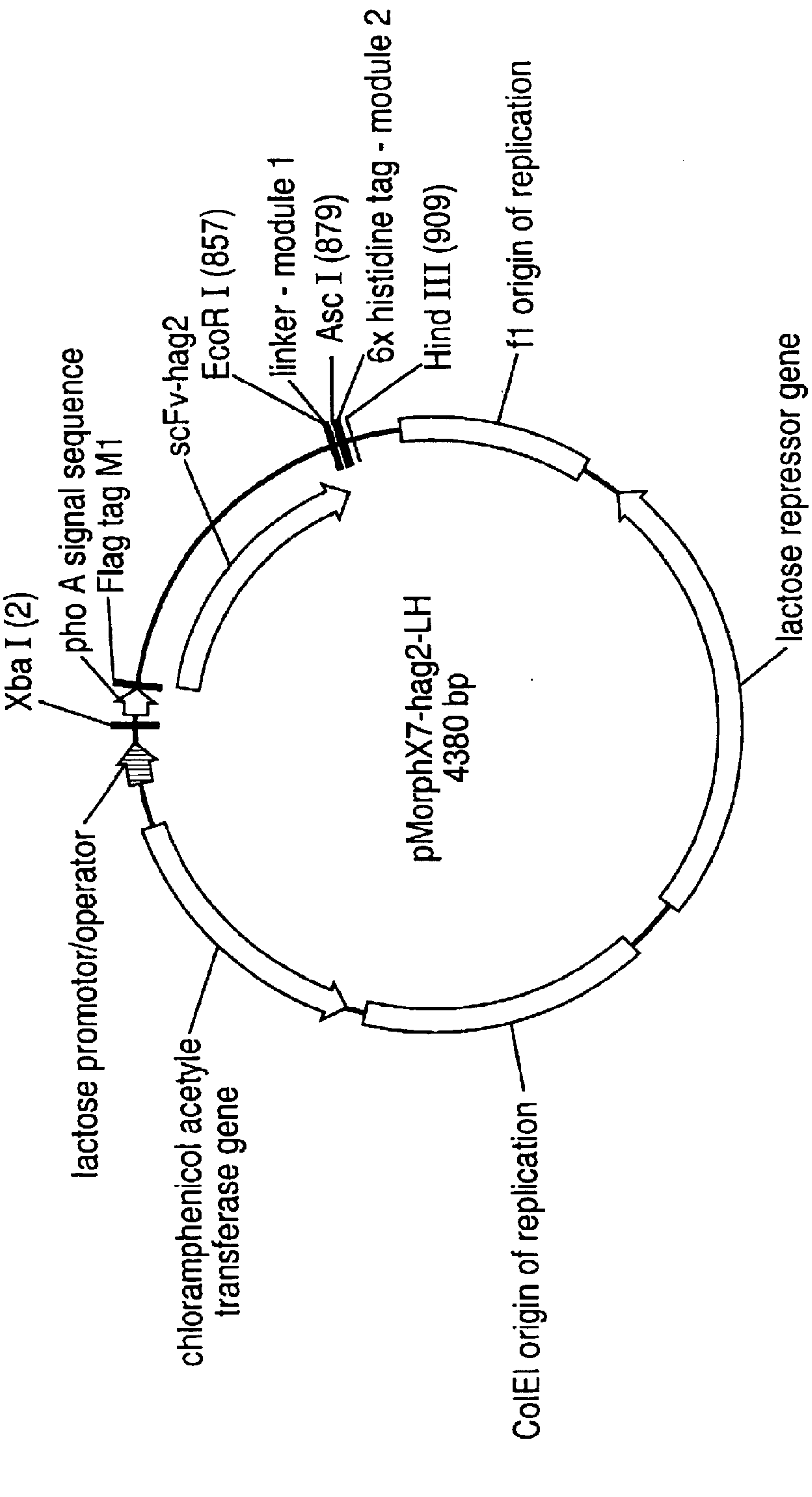
FIG. 1*a*: Vector map of construct pMorphX7-hag2-LH.

All vectors used are derivatives of the high copy phagemid pMorphX7-LH (FIGS. 1*a*+*b*), a derivative of the pCAL vector series (WO 97/08320; Knappik et al., 2000). The expression cassette comprises the phoA signal sequence, a minimal binding site for the monoclonal antibody (mab) anti-FLAG M1 (Sigma #F-3040) (Knappik and Plückthun, 1994), a single chain fragment (scFv), a short linker (PGGSG) and a 6× histidine tag (6His; Hochuli et al., 1988) (FIG. 1*a*). pMorphX7-LCH and pMorphX7-LHC have been generated by inserting oligonucleotide cassettes coding for Cys-6His and 6His-Cys, respectively, between the unique AscI and HindIII sites of pMorphX7-LH (FIG. 1*a*, Table 1). All vectors express soluble scFv not genetically fused to any phage coat protein. The conventional phage display vector pMorph13 which is based on the pCAL4 vector described in WO 97/08320 and expresses a fusion of an scFv to the C-terminal part of phage protein pIII was used as positive control. The scFvs have been exchanged between the respective vectors via the unique XbaI and EcoRI sites (c.f. FIG 1*a*).

Description of the scfv—Antigen Interactions

All scFvs derive from a human combinatorial antibody library (HuCAL; WO 97/08320; Knappik et al., 2000). The HuCAL VH and VL consensus genes (described in WO 97/08320), and the CDR3 sequences of the scFvs are given in Table 2. Clone hag2 was selected against a peptide from influenza virus hemagglutinine (aa 99–110 from hemagglutinine plus additional flanking aa (shown in italics, CAGPYDVPDYASLRSHH (SEQ ID NO:14)), and clone MacI-5 against a fragment (MacI) of human CR-3 alpha chain (SWISS-PROT entry P11215, aa 149–353 of human CR-3 alpha fused to a C-terminal sequence containing a 6× histidine tag). The corresponding antigens for ELISA and doped library experiments were obtained as follows. The hag2 specific antigen N1-hag was produced using expression vector pTFT74-N1-hag-HIPM, a derivative of vector pTFT74 (Freund et al., 1993) (FIG. 2). N1-hag comprises aa 1–82 of mature gene III protein of phage M13 containing an additional methionine residue at the N-terminus (N1) fused to the amino acid sequence PYDVPDYASLRSHHHHHH (hag) (SEQ ID NO:1) comprising aa 99–110 from influenza virus hemagglutinine and a 6× histidine tag (in italics) Expression, purification and refolding of N1-hag was done as described (Krebber, 1996, Krebber et al., 1997). As antigen for MacI-5, a purified fragment (MacI) of human CR-3 alpha chain (SWISS-PROT entry P11215) fused to a C-terminal 6× histidine tag was used. In detail, the expression cassette encodes an N-terminal methionine, amino acids 149–353 of human CR-3 alpha and amino acids IEGRHHHHIIH (SEQ ID NO:2). This cassette is flanked by unique restriction sites BspHI and HindIII and can e.g. be introduced into the unique NcoI and HindIII sites of pQE-60 (QIAGEN GmbH, Hilden, Germany), yielding expression vector pQE60-MacI (FIG. 3). Expression and purification was performed using standard methods (The QIAexpressionist™ 3rd edition: A handbook for high-level expression and purification of 6×His-tagged proteins (July 1998). QIAGEN GmbH, Hilden, Germany). Bovine serum albumin (BSA, Sigma #A7906) was used as negative control antigen.

Functionality of scFvs Displayed on Non-Engineered Phages

To demonstrate that the displayed scFvs are functional with respect to recognition of their specific antigens phage ELISAs were performed. The analysis was done for the two HuCAL scFvs hag2 and MacI-5. Three expression systems differing in the modules fused to the C-terminus of the scFv were analysed, namely pMorphX7-LH, pMorphX7-LHC and pMorphX7-LCH.

Phages were produced according to standard procedures using helper phage VCSM13 (Kay et al., 1996). Specific antigen or control antigen (BSA, Sigma #A7906) was coated for 12 h at 4° C. at a concentration of 5 μg/well in PBS to Nunc Maxisorp microtiter plates (#442404).

Figure 4:
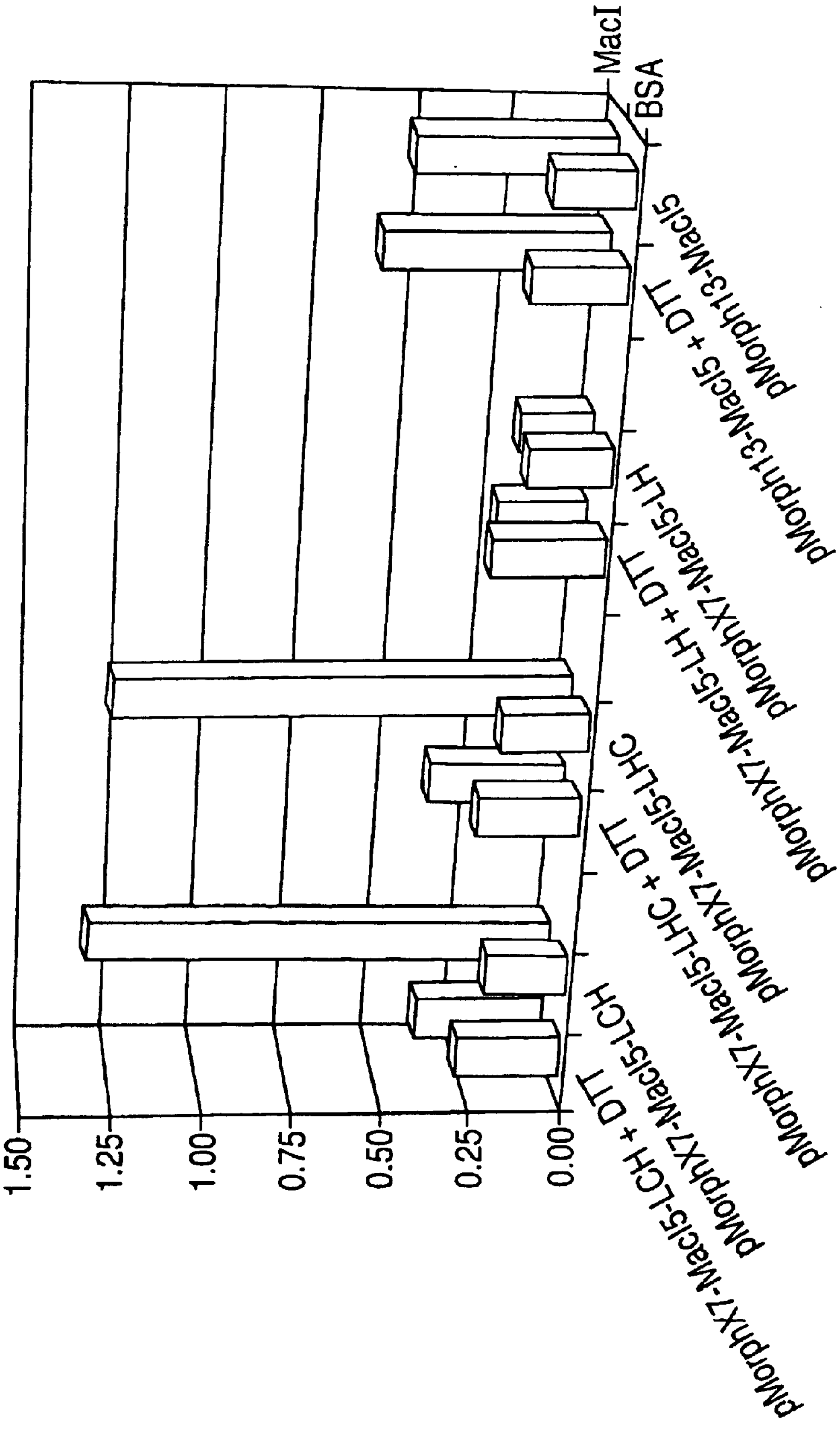
FIG. 4: Specific binding of scFv displayed on non-engineered phages.

Phages were pre-incubated in PBSTM (PBS containing 5% skimmed milk powder and 0.1% Tween 20), either with or without 5 mM DTT, for 2 h at room temperature before they were applied to the ELISA well coated with antigen at a concentration of $1\times10^{10}$ phages per well except for pMorph13 which was used at a concentration of $3\times10^{7}$ phages per well. After binding for 1 h at RT, non-specifically bound phages were washed away with PBS containing 0.05% Tween 20 and bound phages were detected in ELISA using an anti-M13-HRP conjugate (Amersham Pharmacia Biotech #27-9421-01) and BM blue soluble (Boehringer Mannheim #1484281). Absorbance at 370 nm was measured. ELISA signals obtained with the specific antigen were compared to those with the control antigen. Specific binding of scFv displaying phages to antigen could be shown. As an example two of such ELISAs for scFvs hag2 and MacI-5 are presented in FIGS. 4 and 5, respectively. With phages derived from pMorphX7-LCH and pMorphX7-LHC signals between 1.9 and 5.8 times above background were achieved. When 5 mM DTT was added to the phages prior to antigen binding during the pre-incubation step, the ELISA signal was decreased to almost background levels while DTT had no major effect on the conventional display phages (pMorph13).

Enrichment of Non-Engineered Phages Displaying scFv

To prove that non-engineered phages displaying scFvs can be enriched on specific antigen a so called doped library experiment was performed. Specific phages were mixed with a high excess of unspecific phages and three rounds of panning on specific antigen were performed. The enrichment for specific phages was determined after each round. The analysis was done for the two HuCAL scFvs hag2 and MacI-5 in the pMorphX7-LHC vector.

pMorphX7-hag2-LHC and pMorphX7-MacI-5-LHC derived phages were mixed at ratios of $1:10^5$ (pMorphX7-hag2-LHC panning) as well as $10^5:1$ (pMorphX7-MacI-5-LHC panning). Three rounds of panning were performed on the hag2 and MacI-5 specific antigen, respectively. Phages were prepared by standard procedure and pre-blocked by mixing 1:1 with PBSTM (PBS, 5% skimmed milk powder, 0.1% Tween20) and incubation for 2 h at RT. Wells of a Nunc Maxisorp microtiter plate (#442404) were coated with specific antigen N1-hag (as well as BSA) at a concentration of 5 μg/well in PBS overnight at 4° C., and subsequently blocked with 400 μl PBSM (PBS, 5% skimmed milk powder) for 2 h at RT. For the first round, $10^{11}$ pre-blocked phages were applied per well and incubated for 1 h at RT on a microtiter plate shaker. Phage solution was removed and wells were washed 3 times with PBST (PBS, 0.05% Tween20) and 3 times with PBS. Bound phages were eluted with 100 mM triethylamine according to standard protocols and used for infection of TG1 cells. In addition, residual phages were eluted by direct infection of TG1 added to the wells. After each round of panning on specific antigen the ratio of specific to unspecific phages was determined by analysing at least 46 independent infected cells via PCR. The PCR was performed according to standard protocols using single colonies as source of template and oligonucleotides specific for VH CDR3 and VL CDR3 of each scFv as primers. After 3 rounds of panning, ~4% positive clones (4 out of 93 clones analysed) were obtained for the pMorphX7-hag2-LHC panning and ~90% positive clones (82 out of 91 clones analysed) were obtained for the pMorphX7-MacI-5-LHC panning.

EXAMPLE 2

Display of (Poly)Peptides/Proteins on the Surface of Engineered Filamentous Bacteriophage Particles Via Formation of Disulfide Bonds

EXAMPLE 2.1

Display of scFvs

Example 1 described above shows that functional scfvs can be displayed on non-engineered phages via disulfide bonds. This system can be further improved, e.g. via engineering an exposed cysteine on a phage coat protein. One candidate phage coat protein is protein III (pIII) which is composed of three domains N1, N2 and pIIICT. Possible sites for positioning an unpaired cysteine residue are the linker regions between the domains or the exposed N-terminus of the domain or the pIIICT in a truncated pIII version. A further example would be phage coat protein IX (pIX) where the cysteine could e.g. be linked to the N-terminus of the full length protein. In principle the cassettes for expression of such engineered proteins can be placed on the vector which is providing the scFv (one-vector system), or on a separate vector (two-vector system).

In the following we will describe experiments in which we engineered both a full length and a truncated pIII version as well as pIX) These proteins were co-expressed in the same bacterial cell together with the scfv, either from the same phagemid (pMorph18-C-gIII-scFv-LHC derivatives; one-vector system) or from a separate plasmid (pBR322-C-gIII or pUC 19-C-gill and derivatives; two-vector system).

Construction of Vectors Expressing scFvs and Engineered Phage Coat Proteins

Phage coat protein expression cassettes for the two-vector system were constructed as follows: Two different expression cassettes flanked by unique NheI and HindIII restriction sites at the ends were made positioning an unpaired cysteine residue at the exposed N-terminus of the N1-domain of frill length mature pIII (C-gIII) or at the N-terminus of the pIIICT domain of the truncated protein (amino acids 216 to 406 of protein pIII; C-gIIICT) (FIGS. 6*b*+*c*)). Both expression cassettes are under the control of the lac promotor/operator region and comprise the signal sequence ompA, amino acids DYCDIEF (SEQ ID NO:3) and the pill or pIIICT ORF (complete amino acid sequences are given in Table 3). Plasmids expressing the modified pIII proteins were obtained by inserting these NheI-HindIII cassettes into plasmid pBR322 and pUC19 via the unique NheI and HindIII or XbaI and HindIII sites, respectively. As an example, the vector map of pBR-C-gIII is depicted in FIG. 6*a*. The resulting plasmids, pBR-C-gIII, pBR-C-gIIICT, pUC-C-gIII and pUC-C-gIIICT, were co-transformed with pMorphX7-LHC phagemids expressing the modified scFv (Example 1) into *E. coli* TG1 selecting for both antibiotic markers.

In the one-vector system both the modified phage coat proteins as well as the modified scFv were expressed from a dicistronic phagemid under control of the lac promotor/operator region. The first expression cassette comprises the signal sequence ompA, amino acids DYCDIEF (SEQ ID NO:3) and the ORF for the respective phage coat protein or part thereof The unpaired cysteine residue was linked to the exposed N-terminus of the N1-domain of full length mature pIII (C-gIII), to the N-terminus of the truncated protein III (amino acids 216 to 406 of protein pIII; C-gIIICT) and to the N-terminus of protein IX (C-gIX), respectively (amino acid sequences are given in Table 4). The second expression cassette comprises the phoA signal sequence, the ORF of the respective scFv, a short linker (PGGSG), a 6× histidine tag (6His; Hochuli et al., 1988) and the single cysteine residue (see pMorphX7-LHC, Table 1). The complete vector sequence of pMorph18-C-gIII-hag2-LHC coding for modified full length pIII as well as modified scFv hag2 and the respective vector map are given in FIGS. 7*a*+*b*. The different phage coat proteins can be exchanged via EcoRI and StuI in a three fragment cloning procedure due to a second EcoRI site at the 3' end of the scFvs. The different engineered scFvs can be cloned via the unique MfeI and HindIII sites. A derivative of this vector, pMorph20-C-gIII-hag2-LHC, contains a unique EcoRI site at the 3' end of the scFv while the second site (between the ompA signal sequence and the gIII ORF) was deleted via silent PCR mutagenesis. This construct allows the cloning of scFvs or scFv pools via the unique SphI and EcoRI sites.

Attachment of scFvs to Phage Coat Proteins via Disulfide Bonds

Phage for biopanning applications can be produced using helper phage VCSM13 following standard protocols (Kay et al., 1996). In addition to helper phage proteins, engineered phage coat protein and soluble modified scFv were co-expressed from the one-or two-vector systems described above. To demonstrate that the scFvs attach to the engineered phage coat proteins via disulfide bridges and are incorporated into phage particles, scFv displaying phages were run on SDS PAGE under non-reducing and reducing conditions. Western blot analysis was performed with anti-pIII and anti-Flag M1 antisera.

Phages were produced according to standard procedures using helper phage VCSM13 (Kay et al., 1996). Phages were pre-incubated in PBS with 5 mM DTT or without DTT (reducing and non-reducing conditions, respectively) for 30 minutes at room temperature before adding SDS loading buffer lacking reducing agents such as DTT or β-mercaptoethanol. 1–5×$10^{10}$ phages per lane were run on a 4–15% SDS PAGE (BioRad) and blotted onto PVDF membranes. For the anti-pIII Western blot, the membrane was blocked in MPBST (PBS buffer containing 5% milk powder and 0.05% Tween20) and developed with mouse anti-pIII (1:250 dilution; Mobitec) as primary antibody, anti-mouse-IgG-AP conjugate (1:10000 dilution; SIGMA) as secondary antibody and BCIP/NPT tablets (SIGMA) as substrate. For the anti-Flag M1 Western blot, the membrane was blocked in MTBST-$CaCl_2$ (TBS buffer containing 5% milk powder, 0.05% Tween20 and 1 mM $CaCl_2$) and developed with mouse anti-Flag M1 (1:5000 dilution; Sigma) as primary antibody, anti-mouse-IgG-AP conjugate (1:10000 dilution; SIGMA) as secondary antibody and BCIP/NPT tablets (SIGMA) as substrate.

Figure 8A:
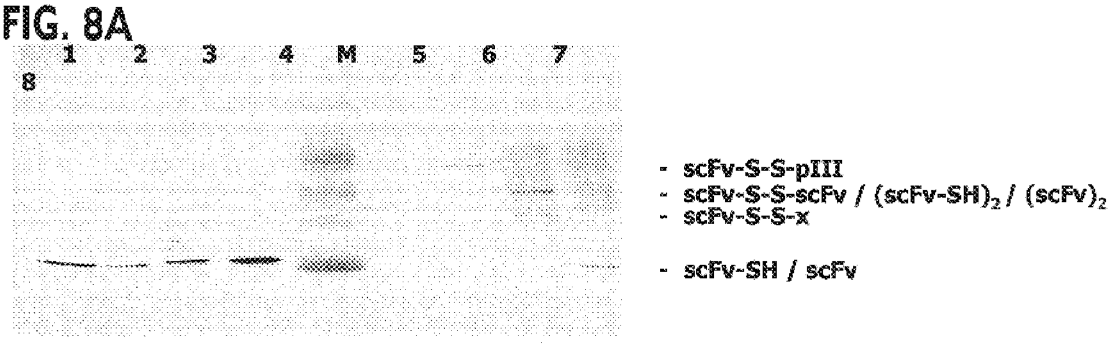
Figure 8B:
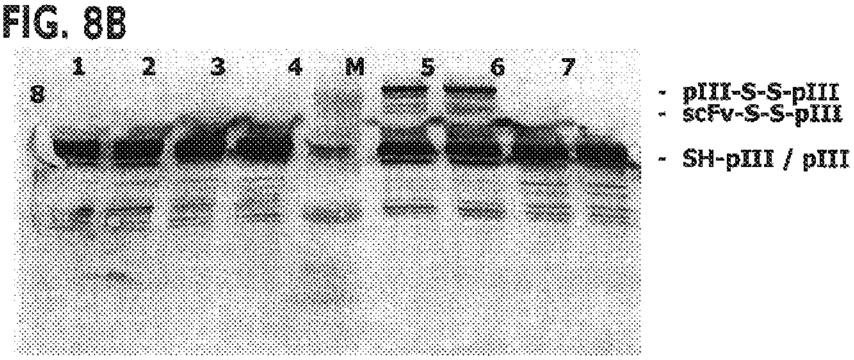
Figure 9A:
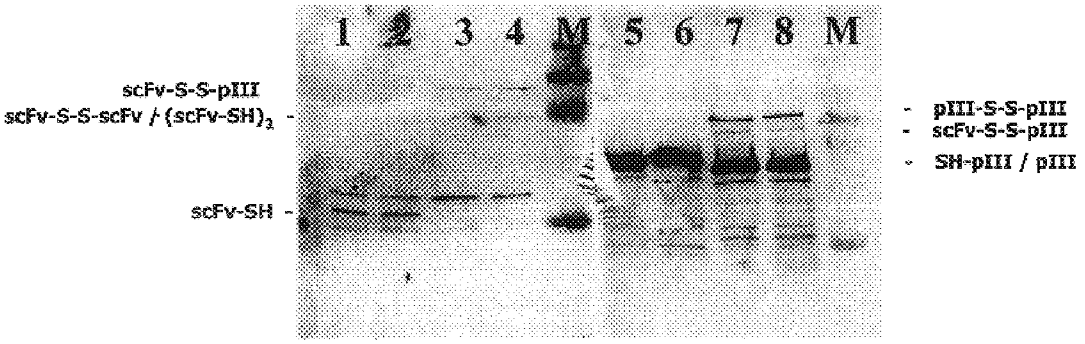
Figure 9B:
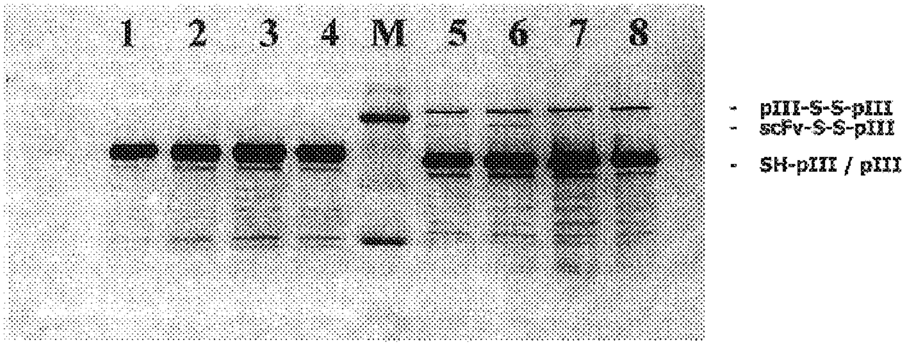

Specific bands migrating at the height expected for the scFv linked to the full length pIII could be shown both for the one-and two-vector system. This signal can only be seen under non-reducing conditions and disappears under DTT indicating that pIII and scFv are linked via disulfide bonds (scFv-S—S-pIII). As an example for the two-vector system an anti-Flag M1 and anti-pIII Western blot for scFv MacI-5 is shown in FIG. 8. When the scFv without additional cysteines (pMorph7x-MacI-5-LH) is expressed, only free scFv sticking to phages can be detected in the anti-Flag M1 Western blot (lane 8, FIG. 8A). When an additional cysteine is added to the scFv (pMorphX7-MacI-5-LHC), those bands can hardly be seen and a band migrating at the height of scFv dimers (scFv-S—S-scFv and/or $(scFv\text{-}SH)_2$) (and an unknown additional band (scFv-S-SX)) appear (lane 7, FIG. 8A). When the engineered scFvs are co-expressed with an engineered pIII containing an additional cysteine at the N-terminus (pMorphX7-MacI-5-LHC and pBR-C-gIII) the signals shift to a molecular weight corresponding to scFv-pIII heterodimers (scFv-S—S-pIII) (lane 6, FIG. 8A). As expected, this scFv-S—S-pIII signal cannot be seen when non-engineered scFvs are co-expressed with the engineered pIII (pMorphX7-MacI-5-LH and pBR-C-gIII), although similar numbers of phage particles are loaded in each lane (lane 5, FIG. 8A). In the presence of reducing agents, the predominant signals are obtained from free scFvs for all expression systems (lanes 1–4, FIG. 8A). In the anti-pIII Western blot, free protein III (pIII-SH and/or pIII) can be seen for all expression systems both under reducing and non-reducing conditions (lanes 1–8, FIG. 8B). Specific bands migrating at the height expected for disulfide bonded protein III dimers (pIII-S—S-pIII) can only be detected under non-reducing conditions when engineered protein III is expressed (lanes 5 and 6 of FIG. 8B). Only when both engineered scFv and engineered protein III are co-expressed an additional band migrating at the height of a disulfide-linked scFv and protein III (scFv-S—S-pIII) appears in addition to the disulfide bonded protein III dimers (lane 6, FIG. 8B). This band corresponds in size to the scFv-S—S-pIII signal detected in the anti-Flag M1 Western (c.f. lane 6, FIG. 8A) and is DTT sensitive (c.f. lane 2, FIG. 8A). DTT sensitive bands migrating at the height of disulfide-linked scFv and protein III and being detected both with anti-Flag M1 and anti-pIII antisera were also observed when engineered scFv and engineered pIII were co-expressed from the same phagemid (pMorph18-C-pIII-scFv-LHC). As an example for this one-vector system an anti-Flag M1 and anti-pIII Western blot for scFv hag2 and anti-pIII Western blots for scFvs AB 1.1 and MacI-5 are shown in FIGS. 9A and 9B, respectively.

Functionality of scFvs Displayed on Engineered Phages

To show that the displayed scFvs are functional with respect to recognition of the specific antigen, phage ELISAs were performed. The analysis was done for the HuCAL scFvs MacI-5 and hag2. For the two-vector system, pMorphX7-LHC was co-transformed with pBR-C-gIII, pBR-C-gIIICT, pUC-C-gIII and pUC-C-gIIICT, respectively. Three different one-vector constructs were analysed, namely pMorph18-C-gIII-scFv-LHC, pMorph18-C-gIIICT-scFv-LRC and pMorph18-C-gIX-scFv-LHC. To demonstrate that the scFvs attach to the engineered phage coat proteins via disulfide bonds, phage ELISAs were performed both under non-reducing and reducing conditions.

Phages were produced according to standard procedures using helper phage VCSM13 and phage titers were determined (Kay et al., 1996). Specific antigen or control antigen (BSA, Sigma #A7906) was coated for 12 hours at 4° C. at an amount of 5 μg/well in PBS to Nunc Maxisorp microtiter plates (# 442404) and blocked with PBS containing 5% skimmed milk powder for 2 h. Phages were pre-incubated in PBS containing 2.5% skimmed milk powder, 0.05% Tween 20, as well as 5 mM DTT, where applicable, for 2 h at room temperature before they were applied to the ELISA well coated with antigen at a concentration range between 6.4×$10^6$ and 1×$10^{11}$ phages per well. After binding for 1 h at RT, unspecifically bound phages were washed away with PBS containing 0.05% Tween 20 and bound phages were detected in ELISA using an anti-M13HRP conjugate (Amersham Pharmacia Biotech #27-9421-01) and BM blue soluble (Boehringer Mannheim #1484281). Absorbance at 370 nm was measured. ELISA signals obtained with the specific antigen were compared to those with the control antigen. Specific binding of scFv displaying phages to antigen could be shown for the C-gIII, C-gIIICT and C-gIX constructs in the one-vector format. C-gIII and C-gIIICT were also tested and shown to work in both two-vector systems. As an example four such ELISAs for scFv MacI-5 are presented in FIGS. 10–13. In all cases where phage coat proteins are engineered with an additional cysteine residue, ELISA signals are significantly increased compared to the pMorphX7-LHC signals where only the scFv carries an additional cysteine. When 5 mM DTT was added to the phages prior to antigen binding during the pre-incubation step, the ELISA signal was decreased to almost background levels for all three engineered phage coat constructs as well as the non-engineered pMorphX7-LHC phages while DTT had no major effect on the conventional display phages (pMorph13; FIG. 13). This shows that for both the non-engineered and engineered phages disulfide bonds are essential for the functional display of scFvs on phages and thus for the specific binding of scFv displaying phages to antigen.

Enrichment of Engineered Phages Displaying scfv in "Doped Library" Experiments

To prove that engineered phages displaying scFvs can be enriched on specific antigen, a "doped library" experiment was performed: specific phages were mixed with a high excess of unspecific phages and three rounds of panning on specific antigen were performed The enrichment for specific phages was determined after each round. The analysis was done for the two HuCAL scFvs hag2 and MacI-5 in the pMorph18-C-gIII-scFv-LHC one-vector system.

pMorph18-C-gIII-hag2-LHC and pMorph18-C-gIII-MacI-5-LHC derived phages were mixed at ratios of 1:10 (pMorph18-C-gIII-hag2-LHC panning) as well as $10^5$:1 (pMorph18-C-gIII-MacI-5-LHC panning). Three rounds of panning were performed on the hag2 and MacI-5 specific antigen, respectively. Phages were prepared by standard procedure and pre-blocked by mixing 1:1 with PBSTM (PBS, 5% skimmed milk powder, 0.1% Tween20) and incubation for 2 h at RT Wells of a Nunc Maxisorp plate (#442404) were coated with specific antigen (as well as BSA) at a concentration of 5 μg/well in PBS overnight at 4° C., and subsequently blocked with 400 μl PBSM (PBS, 5% skimmed milk powder) for 2 h at RT. For the first round, $10^{10}$ pre-blocked phages were applied per well and incubated for 1 h at RT on a microtiter plate shaker. Phage solution was removed and wells were washed 3 times with PBST (PBS, 0.05% Tween20) and 3 times with PBS. Bound phages were eluted with 100 mM triethylamine according to standard protocols and used for infection of TG1 cells. In addition, residual phages were eluted by direct infection of TG1 cells added to the wells. After each round of panning on specific antigen, the ratio of specific to unspecific phages was determined by analysing at least 91 independent infected cells via PCR. The PCR was performed according to standard protocols using single colonies as source of template and oligonucleotides specific for VH CDR3 and VL CDR3 of each scFv as primers. After 2 rounds of panning, ~0% positive clones (0 out of 93 clones analysed) were obtained for the pMorph18-C-gIII-hag2-LHC panning and ~3% positive clones (3 out of 91 clones analysed) were obtained for the pMorph18-C-gIII-MacI-5-LHC panning. After 3 rounds of panning, the specific clones were enriched to ~79% (92 out of 117 clones analysed) for the pMorph18-C-gIII-hag2-LHC panning and to ~100% (229 out of 229 clones analysed) for the pMorph18-C-gIII-MacI-5-LHC panning.

Enrichment of Engineered Phages Displaying scFv in Pannings of Pre-Selected Pools To prove that engineered phages displaying scFvs can be selected out of a diverse pool, pannings of pre-selected libraries were performed. Pools after one round of conventional panning were subcloned into the engineered one-vector format and panning was continued for up to three further rounds (cys-display pannings).

Pannings were performed against the following antigens: (i) ICAM1 comprising the extracellular part of mature ICAM1 (amino acids 1–454) plus amino acids CGRDYKDDDKHHHHHH (SEQ ID NO:4) containing the M2-Flag and the 6× histidine tag. (ii) N1-MacI comprising aa 1–82 of mature gene III protein of phage M13 containing an additional methionine residue at the N-terminus plus a short linker at the C-terminus (N1), fused to a polypeptide containing amino acids 149–353 of human CR-3 alpha chain (SWISS-PROT entry P11215) plus the C-terminal sequence IEGRHHHHHH (SEQ ID NO:2) which includes the 6× histidine tag; and (iii) N1-Np50 comprising N1 fused to a polypeptide containing amino acids 2–366 of human NFκB p50 plus amino acids EFSHHHHHH (SEQ ID NO:5) which include the 6× histidine tag. Expression vectors for N1-MacI and N1-Np50 are based on vector pTFT74 (Freund et al., 1993) (complete vector sequence of pTFT74-N1-hag-HIPM given in FIG. 2). Expression, purification and refolding was done as described (Krebber, 1996; Krebber et al., 1997).

Initially, one round of conventional panning of the antibody library HuCAL-scFv (WO 97/08320; Knappik et al., 2000) was performed according to standard protocols. Briefly, wells of Maxisorp microtiterplates (Nunc; #442404) were coated with the respective antigen dissolved in PBS and blocked with 5% skimmed milk powder in PBS. 1≧5×$10^{12}$ HuCAL-scFv phage were added for 1 h at 20° C. After several washing steps with PBST (PBS, 0.05% Tween20) and PBS, bound phage were eluted either with 100 mM triethylamine or 100 mM glycine pH 2.2, immediately neutralised with 1 M Tris/HCl pH 7.0 and used for infection of TG1 cells. In addition, residual phages were eluted by direct infection of TG1 cells added to the wells. Pannings against N1-Np50 used the complete HuCAL-scFv library (κ and λ pools combined), in pannings against N1-MacI κ and λ light chain pools were kept separated. Against ICAM1 one round of conventional panning of the λ Light chain part of HuCAL-scFv was performed and subsequently the selected heavy chains again combined with the complete library of λ light chains. The resulting light chain optimised library had a diversity of $1.4\times10^{7}$.

The scFvs of the respective pools were subcloned into vector pMorph20-C-gIII-scFv-LHC (one-vector format) via the unique SphI and EcoRI sites. Subsequently, three rounds of cys-display panning were performed. Phages were prepared by standard procedure and pre-blocked by mixing 1:1 with PBSTM (PBS, 5% skimmed milk powder, 0.1% Tween20) and incubated for 2 hrs at RT. Wells of a Nunc Maxisorp plate (#442404) were coated with specific antigens at a concentration of 5 μg/well in PBS overnight at 4° C., and subsequently blocked with 400 μl PBSM (PBS, 5% skimmed milk powder) for 2 hrs at RT. For each round of cys-display panning, between $1\times10^{10}$ and $4.5\times10^{11}$ pre-blocked phages were applied per well and incubated for 1 h at RT on a microtiter plate shaker. Phage solution was removed and wells were washed with PBST (PBS, 0.05% Tween20) and PBS with increasing stringency. The $1^{st}$ round was washed 3× quick and 2×5 mm with PBST and PBS, respectively, the $2^{nd}$ round 1× quick and 4×5 mm with PBST and PBS, respectively, and the $3^{rd}$ round 10× quick and 5×5 mm with PBST and PBS, respectively. Bound phages were eluted with 100 mM triethylamine according to standard protocols and used for infection of TG1 cells. In addition, residual phages were eluted by direct infection of TG1 cells added to the wells.

After each round of panning the number of antigen specific phages was determined in an ELISA. N1-MacI, N1-Np50 and ICAM-Strep (comprising amino acids 1–455 of mature ICAM1 plus SAWSHPQFEK (SEQ ID NO:6) containing the Strep-tag II) were used as antigens, respectively. To ensure high level expression the selected scFvs were subcloned into expression vector pMorphX7-FS (Table 1). Subcloning was done in two steps. First the scFv fragments were isolated from pMorph20-C-gIII-scFv-LHC via AflII and EcoRI, then the fragments were re-digested with SphI and cloned into the EcoRI/SphI digested pMorphX7-FS vector. This procedure ensured that only scFvs from vector pMorph20-C-gIII-scFv-LHC were subcloned and excluded any contamination with scFvs from a conventional display or expression vector. Expression of the scFvs and their testing in ELISA against the respective antigens was done according to standard procedures. Clones which showed a signal of at least 3× above background in ELISA were considered positive. The results are summarised in Table 5. To prove that the selected scFvs bind strongly and specifically to their respective antigen several positive clones after 2 rounds of cys-display panning were selected and re-tested in quadruplicates in a specificity ELISA on six different antigens (FIGS. 14 & 15). Enrichment of antigen-specific binders could clearly be demonstrated. Already after two rounds of cys-display panning of the pre-selected pools against N1-MacI, N1-Np50 and ICAM1 between 80% and 97% of the tested clones were positive in ELISA. The affinity of some of the selected scFvs was determined in Biacore and Kd values in the range of 1 nM to 2.2 μM were determined. These results are similar to the enrichment factors and affinities obtained in a conventional panning of the respective pools performed in parallel. Some of the scFvs were selected independently via cys-display as well as conventional panning.

Elution of Engineered Phages Displaying scFv via Reducing Agents

When screening phage display libraries in biopanning the problem remains how to best recover phages which have bound to the desired target. Normally, this is achieved by elution with appropriate buffers, either by using a pH- or salt gradient, or by specific elution using soluble target. However, the most interesting binders which bind with high affinity to the target might be lost by that approach. One option with engineered cys-display phages is that the complexes of target and specific bacteriophages can be treated with reducing agents, e.g. by incubation with DTT, to cleave the disulfide bond between scFv and phage coat protein and to recover the specific bacteriophage particles.

Pannings of pre-selected pools against N1-MacI were performed according to the protocol described above. Phages were eluted either according to the standard protocol with 100 mM triethylamine and a direct infection of TG1 cells by residual phages, or by incubation of the wells with 20 mM DTT in Tris buffer pH 8.0 for 10 min. After each round of panning the pool of selected scFvs was subcloned into expression vector pMorphX7-FS according to the two step procedure described above, and the number of N1-MacI specific scFvs was determined in ELISA. To prove that the selected scFvs bind strongly and specifically to their respective antigen several positive clones were selected and re-tested in triplicates in a specificity ELISA. Enrichment of antigen-specific binders could clearly be demonstrated for both elution procedures. After two rounds of panning of the MacI κ-pool and the MacI λ-pool a two-fold and five-fold, respectively, higher number of ELISA positive clones was obtained for elution with reducing agents compared to conventional elution.

EXAMPLE 2.2: Display of Fabs

Example 2.1 shows that functional single chain fragments can be displayed on engineered phages via disulfide bonds. In the following we will describe experiments which show that the same is true for Fabs. The cysteine was engineered at different positions of the Fab antibody fragment. These Fabs were co-expressed in the same bacterial cell together with engineered full length pIII based on a two-vector system.

Construction of Vectors Expressing Fabs and Engineered pIII

Heavy and light chains of the Fab fragment were expressed from a dicistronic phagemid under control of the lac promotor/operator region. The first expression cassette comprises the signal sequence ompA and the variable and constant domain of the light chain, the second expression cassette comprises the signal sequence phoA and the variable and constant domain of the heavy chain. Heavy and light chain are not linked via a disulfide bond. Modules containing the engineered cysteine were located at the C-terminus of either the light or the heavy chain. Several constructs differing in the amino acid composition of the modules were compared and are summarised in Table 6. As an example the complete vector sequence of pMorphX10-Fab-VL-LHC-VH-FS coding for the modified Fab MacI-5 and the respective vector map are given in FIGS. 16*a+b*.

Two different plasmids were used for expression of full length pIII. Plasmid pBR-C-gIII was already described above. The respective expression cassette comprises the signal sequence ompA, amino acids DYCDIEF (SEQ ID NO:3) and the pill ORF under control of the lactose promotor/operator region (Table 3, FIG. 6). Alternatively, plasmid pBAD-SS-C-gIII was used. Here the respective expression cassette comprises the signal sequence of pIII, amino acids TMACDIEF (SEQ ID NO:7) and the pIII ORF under control of the arabinose promotor/operator region (Table 3). For construction of pBAD-SS-C-gIII the fragment coding for the engineered cysteine plus pIII was amplified from pUG-C-gill via PCR introducing the restriction sites NcoI and HindIII and cloned into the commercially available vector pBAD/gIII A (Invitrogen). The plasmids pBR-C-gIII or pBAD-SS-C-gIII were co-transformed with the respective pMorphX10-Fab phagemids expressing the modified Fab into *E. coli* TG1 selecting for both antibiotic markers.

Description of the Fab–Antigen Interactions

Three different Fabs all deriving from a human combinatorial antibody library (HuCAL; WO 97/08320; Knappik et al., 2000) were used for evaluation of Fab display on engineered phage. The HuCAL VH and VL consensus genes (described in WO 97/08320), and the CDR3 sequences of the Fabs are given in Table 2. Fab MacI-5 is derived from the scFv MacI-5 described above and was converted into the Fab format (complete vector map of pMorphX10-Fab-MacI5-VL-LHC-VH-FS is given in FIG. 16*a*). Fabs MacI-A8 and ICAM1-C8 were isolated directly from one of the HuCAL-Fab libraries. Clone MacI-A8 was selected against antigen MacI-Strep, which comprises an N-terminal methionine, amino acids 149–353 of human CR-3 alpha chain (SWISS-PROT entry P11215) and amino acids SAWSHPQFEK (SEQ ID NO:6) which include the Strep-tag II (Schmidt et al., 1996). Expression and purification were done according to Schmidt & Skerra (1994). N1-MacI was used as corresponding antigen for ELISAs. N1-MacI is described above, and comprises an N-terminal methionine, amino acids 1–82 of mature gene III protein of phage M13 plus a short linker (N1), amino acids 149–353 of human CR-3 alpha chain (SWISS-PROT entry P11215) and amino acids IEGRHHHHHH (SEQ ID NO:2) which include the 6× histidine tag. Clone ICAM1-C8 was selected against antigen ICAM1 described above, which comprises the extracellular part of mature ICAM1 (amino acids 1–454) plus amino acids CGRDYKDDDKHHHHHH (SEQ ID NO:4) containing the M2-Flag and the 6× histidine tags. The same antigen was used for ELISA assays as well as in the doped library experiment.

Attachment of Fabs to Phage Coat Proteins Via Disulfide Bonds

To demonstrate that the Fabs attach to pIII via disulfide bridges and are incorporated into phage particles, the respective phages were run on SDS PAGE under non-reducing and reducing conditions. Western blot analyses were performed with antibodies detecting pill, the heavy chain, the lambda light and the kappa light chain, respectively. All constructs described in table 6 were analysed and the results are shown for pMorphX10-ICAM1C8-VL-LHC-VH-FS plus pBAD-SS-C-gill and pMorphX10-MacIA8-VL-LHC-VH-MS plus pBAD-SS-C-gIII as an example in FIGS. 17 and 18.

Phages were produced using helper phage VCSM13 following standard protocols (Kay et al., 1996). In addition to helper phage proteins, engineered phage coat protein and soluble modified Fab were co-expressed from the two-vector system. Phages were pre-incubated in PBS with or without 20 mM DTT (reducing and non-reducing conditions, respectively) for 1 h at room temperature before adding SDS loading buffer lacking reducing agents such as DTT or β-mercaptoethanol. $1\times10^{10}$ phages per lane were run on a 12% SDS PAGE (BioRad) and blotted onto nitrocellulose membranes (Schleicher & Schuell). For the anti-pIII Western blot, the membrane was blocked in MTBST (50 mM Tris buffer pH 7.4, containing 5% milk powder and 0.05% Tween20) and developed with mouse anti-pIII (1:250 dilution, Mobitec) as primary antibody, anti-mouse-IgG-HRP conjugate (1:5000 dilution; SIGMA) as secondary antibody and BM Blue POD precipitating (Roche #1442066) as substrate. For the detection of the heavy chain, kappa light and lambda light chain the primary antibodies anti-Fd (1:5000 dilution; The binding site PC075), anti-human kappa (1:5000 dilution; Sigma K-4377) and anti-human lambda (1:500 dilution, Sigma L-6522) were used, respectively.

In the anti-pIII Western blots, free protein III (SH-pIII and/or pIII) can be detected for all expression systems both under reducing and non-reducing conditions (FIGS. 17 and 18). When both engineered Fab and engineered protein III are co-expressed a signal migrating at the height of a hetero-dimer of light chain and protein III (VL-CL-SS-pIII) appears under non-reducing conditions. In addition, a band migrating at the height expected for disulfide bonded protein III dimers (pIII-SS-pIII) can be seen (lanes 11 & 12, FIGS. 17, 18). Both hetero-and homo-dimers disappear when the samples are treated with DTT (lanes 5 & 6, FIGS. 17 and 18) or when modified Fabs are coexpressed with non-engineered pIII (lanes 3, 4, 9 & 10, FIGS. 17 and 18). The hetero-dimer in this case of light chain linked to the full length pIII could also be detected with anti-light chain antibodies in non-reducing gels but was absent under reducing conditions. In addition, a band migrating at the height expected for the homo-dimer of the light chain (VL-CL-SS-VL-CL) was detectable (data not shown). Similar results were obtained for all constructs described in Table 6, and no significant difference between vectors pBR-C-gIII and pBAD-SS-C-gIII for supply of engineered pIII was detected (data not shown).

Functionality of Fabs Displayed on Engineered Phages

To show that the displayed Fabs are functional with respect to recognition of the specific antigen phage ELISAs were performed. The analysis was done for the HuCAL Fabs MacI-5, MacI-A8 and ICAM1-C8. All formats differing in the position of cysteine at the Fab were compared (Table 6). To demonstrate that the Fabs attach to the engineered phage coat proteins via disulfide bonds, phage ELISAs were performed both under non-reducing and reducing conditions.

The respective phagemids expressing the modified Fab were co-transformed with pBR-C-gIII and phage production was performed under standard conditions (Kay et al., 1996). Conventional Fab display phages (pMorph18-Fab) served as positive control, a phagemid expression vector for expression of non-engineered Fab (pMorphX9-Fab-FS) served as negative control. Specific antigen or control antigen (BSA, Sigma #A7906) was coated for 12 hours at 4° C. at an amount of 5 μg/well in PBS to Nunc Maxisorp microtiter plates (# 442404) and blocked with PBS containing 5% skimmed milk powder, 0.05% Tween 20 for 1 h. Phages were pre-incubated in PBS containing 5% skimmed milk powder, 0.05% Tween 20, and 10 mM DTT where applicable for 1 h at room temperature before they were applied to the ELISA well coated with antigen at a concentration range between $1\times10^8$ and $1\times10^{10}$ phages per well. After binding for 1 h at RT, unspecifically bound phages were washed away with PBS containing 0.05% Tween 20 and PBS. Bound phages were detected in ELISA using an anti-M13-HRP conjugate (Amersham Pharmacia Biotech #27-9421-01) and BM blue soluble (Roche #1484281). Absorbance at 370 nm was measured. ELISA signals obtained with the specific antigen were compared to those with the control. Up to three independent phage preparations were analysed and mean values are given in FIGS. 19 to 22.

For all different two-vector formats specific binding of Fab displaying phages to antigen could be demonstrated (FIGS. 19–21, lanes 1–4). For Fab MacI-5 no significant difference between the four formats was detected (FIG. 19), while construct pMorphX10-Fab-VL-LHC-VH-FS showed reproducibly best results for Fab MacI-A8 and ICAM1-C8 (FIGS. 20 and 21). When 10 mM DTT was added to the phages prior to antigen binding during the pre-incubation step, the ELISA signal was decreased to almost background levels for all cys-display phages while DTT had no major effect on conventional display phages (pMorph18-Fab) (shown for Fab MacI-5 in FIG. 22). This shows that disulfide bonds are essential for the functional display of Fabs on phages and thus for the specific binding of Fab displaying phages to antigen.

Enrichment of Engineered Phages Displaying Fabs in Doped Library Experiments

To prove that engineered phages displaying Fabs can be enriched on specific antigen, a "doped library" experiment was performed: specific phages were mixed with a high excess of unspecific phages and three rounds of panning on specific antigen were performed. The enrichment for specific phages was determined after each round. The analysis was done for the HuCAL Fab ICAM1-C8 in the two vector system pMorphX10-Fab-VL-LHC-VH-FS plus pBAD-SS-C-gIII.

Engineered phages displaying ICAM1-C8 and MacI-A8 were mixed at ratios of $1:10^5$. Three rounds of panning were performed on the ICAM1 antigen. Phages were prepared by standard procedure, pre-blocked by mixing 1:1 with PBSTM (PBS, 5% skimmed milk powder, 0.1% Tween 20) and incubated for 2 hrs at RT. Wells of a Nunc Maxisorp plate (#442404) were coated with specific antigen at a concentration of 5 μg/well in PBS overnight at 4° C., and subsequently blocked with 400 μl PBSM (PBS, 5% skimmed milk powder) for 2 hrs at RT. For the first round, $10^{11}$ pre-blocked phages were applied per well and incubated for 1 h at RT on a microtiter plate shaker. Phage solution was removed and wells were washed 3 times with PBST (PBS, 0.05% Tween 20; 1× quick, 2× 5 min) and 3 times with PBS (1× quick, 2×5 min). Bound phages were eluted with 100 mM triethylamine according to standard protocols. In addition, residual phages were eluted by direct infection of cells added to the wells. As a direct infection of TG1 cells harbouring pBAD-SS-C-gIII was not efficient enough, eluted phages were used for infection of TG1 cells, amplified and than used for infection of TG1 cells harbouring pBAD-SS-C-gIII. Thus the two-vector system was restored and the next round of panning was performed. While no difference between the two plasmids for expression of engineered pIII (pBR-C-gIII and pBAD-SS-C-gIII) was observed with respect to phage ELISA and WB, infection of TG1 cells harbouring pBR-C-gIII was not as efficient as infection of TG1 cells harbouring pBAD-SS-C-gIII. After each round of panning the ratio of specific to unspecific phages was determined by analysing at least 92 independent infected cells via PCR. The PCR was performed according to standard protocols using single colonies as source of template and oligonucleotides specific for the lambda light chain (priming in framework 4), the kappa light chain (priming in framework 3) and a vector sequence upstream of the Fab fragment (commercial M13-rev primer,NEB) as primers. Fragments of roughly 420 bp length were expected for lambda Fabs (ICAM1-C8) and 290 bp for kappa Fabs (MacI-A8). After 2 rounds of panning, 61% positive clones (57 out of 93 clones analysed) were obtained, which could be enriched to 100% (92 out of 92 clones analysed) after the third round.

REFERENCES

Ausubel, F. M., Brent, R., Kingston, R. E., Moore, D. D., Sedman, J. G., Smith, J. A. & Struhl, K. eds. (1999). Current Protocols in Molecular Biology. New York: John Wiley and Sons.

Bass, S., Greene, R. & Wells, J. A. (1990) Hormone phage: an enrichment method for variant proteins with altered binding properties. Proteins: Structure, Function and Genetics 8, 309–314.

Bird, R. E., Hardman, K. D., Jacobson, J. W., Johnson, S., Kaufman, B. M., Lee S. M., Lee T., Pope S. H., Riordan G. S. & Whitlow M. (1988). Single-chain antigen-binding proteins [published erratum appears in (1989). Science 244, 409]. Science 242, 423–6.

Brinkmann, U., Reiter, Y., Jung, S., Lee, B. & Pastan, I. (1993). A recombinant immunotoxin containing a disulfide-stabilized Fv fragment. Proc. Natl. Acad. Sci. U.S.A. 90, 7538–7542.

Crameri, R., & Suter, M. (1993). Display of biologically active proteins on the surface of filamentous phages: a cDNA cloning system for selection of functional gene products linked to the genetic information responsible for their production. Gene 137, 69–75.

Crissman, J. W. & Smith, G. P. (1984). Gene-III protein of filamentous phages: evidence for a carboxy-terminal domain with a role in morphogenesis. Virology 132, 445–455.

Dunn, I. S. 1996. Phage display of proteins. Curr. Opin. Biotechnol. 7:547–553.

Freund, C., Ross, A., Guth, B., Plückthun, A. & Holak, T. A. (1993). Characterization of the linker peptide of the single-chain Fv fragment of an antibody by NMR spectroscopy. FEBS Lett. 320, 97–100.

Gao, C., Mao, S., Lo, C.-H. L., Wirsching, P., Lemer, R. A., & Janda, K. D. (1999). Making artificial antibodies: A format for phage display of combinatorial heterodimeric arrays. Proc. Natl. Acad. Sci. U.S.A. 96, 6025–6030.

Ge, L., Knappik, A., Pack, P., Freund, C. & Plückthun, A. (1995). Expressing antibodies in *Escherichia coli*. Antibody Engineering. A Practical Approach (Ed. C.A.K. Borrebaeck). IRL Press, Oxford, pp. 229–266.

Glockshuber, R., Malia, M., Pfitzinger, I. & Plückthun, A (1992). A comparison of strategies to stabilize immunoglobulin Fv-fragments. Biochemistry 29, 1362–1366.

Greenwood J., Willis A. E. & Perham R. N. (1991) Multiple display of foreign peptides on a filamentous bacteriophage. Peptides from Plasmodium falciparum circumsporozoite protein as antigens. J. Mol. Biol. 220, 821–827.

Hiatt, A. (1990). Antibodies produced in plants. Nature 344, 469–470.

Hiatt, A. & Ma, J. K. (1993). Characterization and applications of antibodies produced in plants. Int. Rev. Immunol. 10, 139–152.

Hochuli, E., Bannwarth, W., Döbeli, H., Gentz, R. & Stüber, D. (1988). Genetic approach to facilitate purification of recombinant proteins with a novel metal chelate adsorbent. Bio/Technology 6, 1321–1325.

Hopp, T. P., Prickett, K. S., Price, V. L., Libby, R. T., March, C. J., Cerretti, D. P., Urdal, D. L. & Conlon, P. J. (1988). A short polypeptide marker sequence useful for recombinant protein identification and purification. Bio/Technology 6, 1204–1210.

Horwitz, A. H., Chang, C. P., Better, M., Hellstrom, K. E. & Robinson, R. R. (1988). Secretion of functional antibody and Fab fragment from yeast cells. Proc. Natl. Acad. Sci. U.S.A. 85, 8678–8682.

Huston, J. S., Levinson, D., Mudgett-Hunter, M., Tai, M. S., Novotny, J., Margolies, M. N., Ridge, R. J., Bruccoleri, R. E., Haber, E. & Crea, R. (1988). Protein engineering of antibody binding sites. Recovery of specific activity in an anti-digoxin single-chain Fv analogue produced in *Escherichia coli*. Proc. Natl. Acad. Sci. U. S. A. 85, 5879–5883.

Jespers L. S., Messens S. H., De Keyser A., Eeckhout D., Van d. B., I, Gansemans Y. G., Lauwereys M. J., Vlasuk G. P. & Stanssens P. E. (1995). Surface expression and ligand-based selection of cDNAs fused to filamentous phage gene VI. Biotechnology (N.Y.) 13, 378–382.

Kay, B. K., Winter, J. & McCafferty, J., eds. (1996). Phage display of peptides and proteins: a laboratory manual. Academic Press, Inc., San Diego.

Knappik, A. & Plückthun, A. (1994). An improved affinity tag based on the FLAG peptide for detection and purification of recombinant antibody fragments. BioTechniques 17, 754–761.

Knappik, A., Ge, L., Honegger, A., Pack, P., Fischer, M., Wellnhofer, G., Hoess, A., Wölle, J., Plückthun, A. & Virnekäs, B. (2000). Fully synthetic Human Combinatorial Antibody Libraries (HuCAL) based on modular consensus frameworks and CDRs randomized with trinucleotides. J. Mol. Biol. 296, 57–86.

Krebber, C. (1996). Selektiv infektiöse Phagen: In vivo Selektion auf Interaktionen zwischen Protein und Ligand. Dissertation at the University of Zurich.

Krebber, C., Spada, S., Desplancq, D., Krebber, A., Ge, L. & Plückthun, A. (1997). Selectively-infective phage (SIP): A mechanistic dissection of a novel in vivo selection for protein-ligand interactions. J. Mol. Biol. 268, 607–618.

Lindner, P., Guth, B., Wulfing, C., Krebber, C., Steipe, B., Muller, F. & Plückthun, A. (1992). Purification of native proteins from the cytoplasm and periplasm of *Escherichia coli* using IMAC and histidine tails: a comparison of proteins and protocols. *Methods: A Companion to* Methods Enzymol. 4, 41–56.

Maruyama I. N., Maruyama H. I. & Brenner S. (1994) Lambda foo: a lambda phage vector for the expression of foreign proteins. Proc. Natl. Acad. Sci. U.S.A. 91, 8273–8277.

McGregor, D. (1996). Selection of proteins and peptides from libraries displayed on filamentous bacteriophage. Mol. Biotechnol. 6:155–162.

Mikawa Y. G., Maruyama I. N. & Brenner S. (1996). Surface display of proteins on bacteriophage lambda heads. J. Mol. Biol. 262, 21–30.

Model, P. & Russel, M. (1988). Filamentous bacteriophage. p 375–456. In R. Calendar (ed.), The bacteriophages, vol. 2, Plenum, New York, N.Y.

Nyyssönen, E., Penttila, M., Harkki, A., Saloheimo, A., Knowles, J. K. & Keranen, S. (1993). Efficient production of antibody fragments by the filamentous fungus Trichoderma reesei. Bio/Technology 11, 591–595.

Parmley S. F. & Smith G. P. (1988) Antibody-selectable filamentous fd phage vectors: affinity purification of target genes. Gene 73, 305–318.

Potter, K. N., Li, Y. & Capra, J. D. (1993). Antibody production in the baculovirus expression system. Int. Rev. Immunol. 10, 103–112.

Ridder, R., Schmitz, R., Legay, F. & Gram, H. (1995). Generation of rabbit monoclonal antibody fragments from a combinatorial phage display library and their production in the yeast Pichia pastoris. Bio/Technology 13, 255–260.

Riechmann, L. & Holliger, P. (1997). The C-terminal domain of TolA is the co-receptor for filamentous phage infection of *E. coli*. Cell 90, 351–360.

Sambrook, J., Fritsch, E. F. & Maniatis, T. (1989). Molecular Cloning: A laboratory manual, Cold Spring Harbor Laboratory Press, Cold Spring Harbor, USA.

Schmidt, T. G. & Skerra, A. (1994). One-step affinity purification of bacterially produced proteins by means of the "Strep tag" and immobilized recombinant core streptavidin. J. Chromatogr. A 676, 337–345.

Schmidt, T. G., Koepke, J., Frank, R., Skerra, A. (1996). Molecular interaction between the Strep-tag affinity peptide and its cognate target, streptavidin. J. Mol. Biol. 255, 753–766.

Skerra, A. & Plückthun, A. (1988). Assembly of a functional immunoglobulin Fv fragment in *Escherichia coli*. Science 240, 1038–1041.

Smith G. P. (1985). Filamentous fusion phage: novel expression vectors that display cloned antigens on the virion surface. Science 228, 1315–1317.

Stengele, I., Bross, P., Garces, X., Giray, J. & Rasched, I. (1990). Dissection of functional domains in phage fd adsorption protein. J. Mol. Biol. 212, 143–149.

Sternberg N. & Hoess R. H. (1995). Display of peptides and proteins on the surface of bacteriophage lambda. Proc. Natl. Acad. Sci. U.S.A. 92, 1609–1613.

Trill, J. J., Shatzman, A. R. & Ganguly, S. (1995). Production of monoclonal antibodies in COS and CHO cells. Curr. Opin. Biotechnol. 6, 553–560.

Ward, V. K., Kreissig, S. B., Hammock, B. D. & Choudary, P. V. (1995). Generation of an expression library in the baculovirus expression vector system. J. Virol. Methods 53, 263–272.

Whitelam, G. C., Cockburn, W. & Owen, M. R. (1994). Antibody production in transgenic plants. Biochem. Soc. Trans. 22, 940–944.

Wu, X. C., Ng, S. C., Near, R. I. & Wong, S. L. (1993). Efficient production of a functional single-chain anti-digoxin antibody via an engineered Bacillus subtilis expression-secretion system. Bio/Technology 11, 71–76.

TABLE 1

Amino acid sequence of ORF modules between the EcoRI and HindIII sites of vectors pMorphX7-hag2-FS, pMorphX7-hag2-LH, pMorphX7-hag2-LCH and pMorphX7-hag2-LHC

| Construct | EcoRI | Module 1 | AscI | Module 2 | HindIII |
|---|---|---|---|---|---|
| pMorphX7-FS | EF | DYKDDDDK (SEQ ID NO:8) | GAP | WSHPQFEK-stop (SEQ ID NO: | stop |
| pMorphX7-LH | EF | PGGSG (SEQ ID NO:10) | GAP | HHHHHH-stop (SEQ ID NO:11) | stop |
| pMorphX7-LCH | EF | PGGSG (SEQ ID NO:10) | GAP | CHHHHHH-stop (SEQ ID NO:12) | stop |
| pMorphX7-LHC | EF | PGGSG (SEQ ID NO:10) | GAP | HHHHHHC-stop (SEQ ID NO:13) | stop |

TABLE 2

Amino acid sequence of HuCAL scFvs and HuCAL Fabs*

| scFv | antigen | VH | VH CDR3 | VL | VL CDR3 |
|---|---|---|---|---|---|
| hag2 | peptide of influenza virus hemagglutinine (CAGPYDVPDYASLRSHH) (SEQ ID NO: | VH3 | RSGAYDY (SEQ ID NO: | VK4 | QQYSSFPL (SEQ ID NO: |
| AB 1.1 | 12 amino acid peptide | VH3 | 10 amino acid residues | Vλ1 | 9 amino acid residues |
| MacI-5 | fragment of human CR-3 alpha chain | VH2 | FDPFFDSFFDY (SEQ ID NO:17) | Vλ1 | QSYDQNALVE (SEQ ID NO:18) |
| MacI-A8 | fragment of human CR-3 alpha chain | VH3 | HGYRKYYTDM FDV (SEQ ID NO:19) | Vκ1 | HQVYSTSP (SEQ ID NO:20) |
| ICAM1-C8 | human ICAM1 | VH2 | FPYTYTIGFMID N (SEQ ID NO:21) | Vλ3 | QSYDSGNL (SEQ ID NO:22) |

*details are given in the Examples

TABLE 3

Amino acid sequence of engineered phage coat proteins of vector pBR-C-gIII and derivatives

| Construct | Signal Sequence | | EcoRV-EcoRI | sequence | HindIII |
|---|---|---|---|---|---|
| pUC-C-gIII pBR-C-gIII | MKKTAIAIAVAL AGFATVAQA (ompA) | **DYC** | DI EF | AETVESCLAKPHTENSFTNYWKDD KTLDRYANYEGCLWNATGVVVCT GDETOCYGTWVPJGLAIPENEGGGS EGGGSEGGGSEGGGTKPPEYGDTPI PGYTYPNPLDGTYPPGTEQNPAMN PSLEESOPLNTFMFQThRfRNRQGA LTVYTGTVTOGTDPVKTYYOYTPV SSKAMYDAYWNGKFRDCAFHSGF NEDPFVCEYOGQSSDLPOPPVNAG GGSGGGSGGGSEGGGSEGGGSEGG GSEGGGSGGGSGSGDFDYEKMAN ANKGAMTENADENALOSDAKGKL DSVATDYGAAIDGFIGDVSGLANG NGATGDFAGSNSQMAQVGDGDNS PLMNNFROYLPSLPQSVECRPYVFG AGKPYEFSIDCDKTNLFRGVFAFLLY VATFMYVFSTFAMILRLNKES (SEQ ID NO:23) | stop |
| pUC-C-gIIICT pBR-C-gIIICT | MKKTAIAIAVAL AGFATVAQA (ompA) | **DYC** | DI EF | NAGGGSGGGSGGGSEGGGSEGGGS EGGGSEGGGSGGGSGSGDFDYEK MANANKGAMTENADENALOSDAK GKLDSVATDYGAAIDGFIGDVSGL ANGNGATGDFAGSNSOMAOVGDG DNSPLMNNFRQYLPSLPOSVECRPF VFGAGKPYEFSTDCDKINLFRGVFA FLLYVATFMYVFSTFANILRNKES (SEQ ID NO:24) | stop |
| pBAD-SS-C-gIII | MIKKLLFAIPLVVTMA PFYSHS | DY **C** | DI EF | AETVESCLAKPHTENSFTNVWKDDKT LDRYANYEGCLWNATGVVVCTGDET | stop |

TABLE 3-continued

Amino acid sequence of engineered phage coat proteins of vector pBR-C-gIII and derivatives

| Construct | Signal Sequence | | EcoRV-EcoRI | sequence | HindIII |
|---|---|---|---|---|---|
| | (gIII) | NcoI<br>(StyI)<br>/SphI | | QCYGTWVPIGLAIPENEGGGSEGGGSE<br>GGGSEGGGTKPPEYGDTPIPGYTYINP<br>LDGTYPPGTEQNPANPNPSLEESQPLN<br>TFMFQNNRFRNRQGALTVYTGTVTQG<br>TDPVKTYYQYTPVSSKAMYDAYWNG<br>KFRDCAFHSGFNEDPFVCEYQGQSSDL<br>PQPPVNAGGGSGGGSGGGSEGGGSEG<br>GGSEGGGSEGGGSGGGSGSGDFDYEK<br>MANANKGAMTENADENALQSDAKGK<br>LDSVATDYGAAIDGFIGDVSGLANGNG<br>ATGDFAGSNSQMAQVGDGDNSPLMN<br>NFRQYLPSLPQSVECRYVFGAGKPYE<br>FSIDCDKJNLFRGVFAFLLYVATFMYV<br>FSTFANILRNKES<br>(SEQ ID NO:25) | |

The engineered Cys is written in bold

Sequence of wild type phage coat proteins is underlined

TABLE 4

Amino acid sequence of engineered phage coat proteins of vector pMorph18-C-gIII-scFv-LHC and derivatives

| Construct | OmpA Signal Sequence | | EcoRV-EcoRI | sequence | StuI |
|---|---|---|---|---|---|
| pMorph18-C-gIII-scFv-LHC | MKKTAIAIAVAL AGFATVAQA | DY **C** | DI EF | AETVESCLAKPHTENSFTNVSKD<br>DKTLDRYANYEGCLWNATGVVV<br>CTGDETQCYGTWVPIGLAIPENEG<br>GGSEGGGSEGGGSEGGGTKPPEY<br>GDTPIPGYTYIMNPLDGTYPPGTEQ<br>NPANPNPSLEESOPLNTFMQNNR<br>FRNRQGALTVYTGTVTOGTDPVK<br>TYYOYTPVSSKAMYDAYWNGKF<br>RDCAFHSGFNEDPFVCEYOGQSSD<br>LPQPPVNAGGGSGGGSGGGSEEG<br>GSEGGGSEGGGSEGGGSGGGSGS<br>GDFDYEKMANANKGAMTENADE<br>NALOSDAKGKLDSVATDYGAAID<br>GFIGDVSGLANGNGATGDFAGSN<br>SQMAOVGDGDNSPLMINMBRQYL<br>PSLPQSVECRPYVFGAGKYYEFSID<br>CDKTNLFRGVFAFLLYVATFMYXTF<br>STFANILRNKES<br>(SEQ lID NO:26) | stop |
| pMorph18-C-gIIICT-scFv-LHC | MKKTAIAIAVAL AGFATVAQA | DY **C** | DI EF | NAGGGSGGGSGSEGGGSEGGG<br>SEGGGSEGGGSGGGSGSGDFDYE<br>KMANANKGAMTENADENAIOSD<br>AKGKLDSVATDYGAAIDGFIGDVS<br>GLANGNGATGDFAGSNSQMAOV<br>GDGDNSPLMNNFRQYLPSLPQSV<br>ECRPFVFGAGKPYEFSIDCDKINLF<br>RGVFAFLLYVATFMYVFSTFANIL<br>RINKES<br>(SEQ ID NO:27) | stop |
| pMorph18-C-gIX-scFv-LHC | MIKKTAIAIAVAL AGFATVAQA | DY **C** | DI EF | GGGGSMSVLVYSFASFVLGWCLR<br>SGITYFTRLMETSS<br>(SEQ ID NO:28) | stop |

The engineered Cys is written in bold
Sequence of wild type phage coat proteins is underlined

TABLE 5

| Cys-display panning of pre-selected pools | | | | | | |
|---|---|---|---|---|---|---|
| Preselected Pool | # of clones[a] | # of positives[b] | Panning Format | round 1 | round 2 | round 3 |
| N1-MacI κ chains | $2 \times 10^5$ | 3/186 = 2% | Cys-display | 78/279 = 28% | 89/93 = 96% | 92/93 = 99% |
| | | | conventional | 10/93 = 11% | 71/93 = 76% | nd |
| N1-MacI λ chains | $4 \times 10^4$ | 4/186 = 2% | Cys-display | 72/279 = 26% | 90/93 = 97% | 90/93 = 97% |
| | | | conventional | 34/93 = 37% | 87/93 = 94% | nd |
| N1-Np50 | $5 \times 10^4$ | 0/186 = 0% | Cys-display | 17/93 = 18% | 244/279 = 87% | nd |
| | | | conventional | 51/93 = 55% | 86/93 = 92% | nd |
| ICAM1 | $1.4 \times 10^7$ | nd | Cys-display | 4/186 = 2% | 149/186 = 80% | nd |

nd: not determined
[a]N1-MacI, N1-Np50: number of clones after one round of conventional panning; ICAM1: diversity of the light chain optimised pool.
[b]number of ELISA positives of the respective pre-selected pools.

TABLE 6

| Amino acid sequence of modules of engineered Fab fragment | | | | |
|---|---|---|---|---|
| | Module at the light chain | | Module at the heavy chain | |
| Construct | elements | amino acids | elements | amino acids |
| pMorphX10-Fab-VL-LHC-VH-FS | linker-histidine tag-cysteine | SPGGSG-GAP-HHHHHH-**C**-stop (SEQ ID NO:29) | linker Flag tag-linker Strep-tag II | EF-DYKDDDDK-GAP-WSLIPQFEK-stop (SEQ ID NO:30) |
| pMorphX10-Fab-VL-LHC-VH-MS | linker-histidine tag-cysteine | SPGGSG-GAP-HHHHHH-**C**-stop (SEQ ID NO:29) | linker-myc tag-linker-Strep-tag II | EF-EQKLISEEDLN-GAP-WSHIPQFEK-stop (SEQ ID NO:31) |
| pMorphX10-Fab-VL-C-VH-FS | cysteine | deletion of A-**C**-stop (κ-chains) **C**S-stop (λ-chains) | linker-Flag tag-linker-Strep-tag II | EF-DYKDDDDK-GAP-WSIIPQFEK-stop (SEQ ID NO:30) |
| pMorphX10-Fab-VL-C-VH-MS | cysteine | deletion of A-**C**-stop (κ-chains) **C**S-stop (λ-chains) | linker-myc tag-linker-Strep-tag II | EF-EQKLISEEDLN-GAP-WSFEPQFEK-stop (SEQ ID NO:3 1) |
| pMorphX10-Fab-VL-VH-LHC | — | — | linker-histidine tag-cysteine | EF-PGGSG-GAP-HHHHHH-C-stop (SEQ ID NO:32) |
| pMorphX10-Fab-VL-VH-CFS | — | — | cysteine-linker-Flag tag-linker-Strep-tag II | C-EF-DYKDDDDK-GAP-WSHPQFEK-stop (SEQ ID NO:33) |
| pMorphX10-Fab-VL-VH-CMS | — | — | cysteine-linker-myc tag-linker-Strep-tag II | C-EF-EQKLISEEDLN-GAP-WSHPQFEK-stop (SEQ ID NO:34) |

The engineered cysteine is written in bold

What is claimed is:

1. A method for displaying a (poly)peptide/protein on the surface of a bacteriophage particle comprising: causing or allowing the attachment of said (poly)peptide/protein after its expression in an appropriate host cell to a member of the protein coat of said bacteriophage particle being assembled in said host cell, wherein said attachment is caused by the formation of a disulfide bond in said host cell between a first cysteine residue comprised in said (poly)peptide/protein and a second cysteine residue comprised in said member of the protein coat.

2. The method of claim 1, wherein said second cysteine residue is present at a corresponding amino acid position in a wild type coat protein of a bacteriophage.

3. The method of claim 2, wherein said member of the protein coat is a wild type coat protein of a bacteriophage.

4. The method of claim 2, wherein said member of the protein coat is a truncated variant of a wild type coat protein of a bacteriophage, wherein said truncated variant comprises at least that part of said wild type coat protein causing the incorporation of said coat protein into the protein coat of the bacteriophage particle.

5. The method of claim 2, wherein said member of the protein coat is a modified variant of a wild type coat protein of a bacteriophage, wherein said modified variant is capable of being incorporated into the protein coat of the bacteriophage particle.

6. The method of claim 1, wherein said second cysteine residue is not present at a corresponding amino acid position in a wild type coat protein of a bacteriophage.

7. The method of claim 6, wherein said second cysteine has been artificially introduced into a wild type coat protein of a bacteriophage.

8. The method of claim 6, wherein said second cysteine has been artificially introduced into a truncated variant of a wild type coat protein of a bacteriophage.

9. The method of claim 6, wherein said second cysteine has been artificially introduced into a modified variant of a wild type coat protein of a bacteriophage.

10. The method of any one of claims 4 to 9, wherein said second cysteine is present at, or in the vicinity of, the C- or the N-terminus of said member of the phage coat of said bacteriophage particle.

11. The method of claim 1, wherein said bacteriophage is a filamentous bacteriophage.

12. The method of claim 11, wherein said member of the protein coat of the bacteriophage particle is or is derived from the wild type coat protein pIII.

13. The method of claim 11, wherein said member of the protein coat of the bacteriophage particle is or is derived from the wild type coat protein pIX.

14. The method of claim 1, comprising:

(a) providing a host cell harbouring a nucleic acid sequence comprising a nucleic acid sequence encoding said (poly)peptide/protein;

(b) causing or allowing the expression of said nucleic acid sequence; and (c) causing or allowing the production of bacteriophage particles in said host cell.

15. The method of claim 1, wherein said (poly)peptide/protein comprises an immunoglobulin or a functional fragment thereof.

16. The method of claim 15, wherein said functional fragment is an scFv or Fab fragment.

17. The method of claim 1, wherein said (poly)peptide/protein is a member of a diverse collection of(poly)peptides/proteins displayed on a diverse collection of a plurality of bacteriophage particles.

18. A method for displaying a (poly)peptide/protein on the surface of a bacteriophage particle comprising the step of: causing or allowing the attachment of said (poly)peptide/protein after its expression in an appropriate host cell to a member of the protein coat of said bacteriophage particle being assembled in said host cell, wherein said attachment is caused by the formation of a disulfide bond between a first cysteine residue comprised in said (poly)peptide/protein and a second cysteine residue comprised in said member of the protein coat, wherein said (poly)peptide/protein is a member of a diverse collection of (poly)peptides/proteins displayed on a diverse collection of a plurality of bacteriophage particles.

19. The method of claim 18, wherein said bacteriophage is a filamentous bacteriophage.

* * * * *

SEQUENCE LISTING

```
<160> NUMBER OF SEQ ID NOS: 41

<210> SEQ ID NO 1
<211> LENGTH: 18
<212> TYPE: PRT
<213> ORGANISM: artificial sequence
<220> FEATURE:
<223> OTHER INFORMATION: Description of Artificial Sequence: synthetic
      module

<400> SEQUENCE: 1

Pro Tyr Asp Val Pro Asp Tyr Ala Ser Leu Arg Ser His His His His
1               5                   10                  15
```

-continued

His His

<210> SEQ ID NO 2
<211> LENGTH: 10
<212> TYPE: PRT
<213> ORGANISM: artificial sequence
<220> FEATURE:
<223> OTHER INFORMATION: Description of Artificial Sequence: synthetic
module

<400> SEQUENCE: 2

Ile Glu Gly Arg His His His His His His
1 5 10

<210> SEQ ID NO 3
<211> LENGTH: 7
<212> TYPE: PRT
<213> ORGANISM: artificial sequence
<220> FEATURE:
<223> OTHER INFORMATION: Description of Artificial Sequence: synthetic
module

<400> SEQUENCE: 3

Asp Tyr Cys Asp Ile Glu Phe
1 5

<210> SEQ ID NO 4
<211> LENGTH: 16
<212> TYPE: PRT
<213> ORGANISM: artificial sequence
<220> FEATURE:
<223> OTHER INFORMATION: Description of Artificial Sequence: synthetic
module

<400> SEQUENCE: 4

Cys Gly Arg Asp Tyr Lys Asp Asp Asp Lys His His His His His His
1 5 10 15

<210> SEQ ID NO 5
<211> LENGTH: 9
<212> TYPE: PRT
<213> ORGANISM: artificial sequence
<220> FEATURE:
<223> OTHER INFORMATION: Description of Artificial Sequence: synthetic
module

<400> SEQUENCE: 5

Glu Phe Ser His His His His His His
1 5

<210> SEQ ID NO 6
<211> LENGTH: 10
<212> TYPE: PRT
<213> ORGANISM: artificial sequence
<220> FEATURE:
<223> OTHER INFORMATION: Description of Artificial Sequence: synthetic
module

<400> SEQUENCE: 6

Ser Ala Trp Ser His Pro Gln Phe Glu Lys
1 5 10

<210> SEQ ID NO 7
<211> LENGTH: 8
<212> TYPE: PRT
<213> ORGANISM: artificial sequence
<220> FEATURE:

-continued

<223> OTHER INFORMATION: Description of Artificial Sequence: synthetic
      module

<400> SEQUENCE: 7

Thr Met Ala Cys Asp Ile Glu Phe
1               5

<210> SEQ ID NO 8
<211> LENGTH: 8
<212> TYPE: PRT
<213> ORGANISM: artificial sequence
<220> FEATURE:
<223> OTHER INFORMATION: Description of Artificial Sequence: synthetic
      module

<400> SEQUENCE: 8

Asp Tyr Lys Asp Asp Asp Asp Lys
1               5

<210> SEQ ID NO 9
<211> LENGTH: 8
<212> TYPE: PRT
<213> ORGANISM: artificial sequence
<220> FEATURE:
<223> OTHER INFORMATION: Description of Artificial Sequence: synthetic
      module

<400> SEQUENCE: 9

Trp Ser His Pro Gln Phe Glu Lys
1               5

<210> SEQ ID NO 10
<211> LENGTH: 5
<212> TYPE: PRT
<213> ORGANISM: artificial sequence
<220> FEATURE:
<223> OTHER INFORMATION: Description of Artificial Sequence: synthetic
      module

<400> SEQUENCE: 10

Pro Gly Gly Ser Gly
1               5

<210> SEQ ID NO 11
<211> LENGTH: 6
<212> TYPE: PRT
<213> ORGANISM: artificial sequence
<220> FEATURE:
<223> OTHER INFORMATION: Description of Artificial Sequence: synthetic
      module

<400> SEQUENCE: 11

His His His His His His
1               5

<210> SEQ ID NO 12
<211> LENGTH: 7
<212> TYPE: PRT
<213> ORGANISM: artificial sequence
<220> FEATURE:
<223> OTHER INFORMATION: Description of Artificial Sequence: synthetic
      module

<400> SEQUENCE: 12

Cys His His His His His His
1               5

-continued

<210> SEQ ID NO 13
<211> LENGTH: 7
<212> TYPE: PRT
<213> ORGANISM: artificial sequence
<220> FEATURE:
<223> OTHER INFORMATION: Description of Artificial Sequence: synthetic
module

<400> SEQUENCE: 13

His His His His His His Cys
1 5

<210> SEQ ID NO 14
<211> LENGTH: 17
<212> TYPE: PRT
<213> ORGANISM: artificial sequence
<220> FEATURE:
<223> OTHER INFORMATION: Description of Artificial Sequence: synthetic
module

<400> SEQUENCE: 14

Cys Ala Gly Pro Tyr Asp Val Pro Asp Tyr Ala Ser Leu Arg Ser His
1 5 10 15

His

<210> SEQ ID NO 15
<211> LENGTH: 7
<212> TYPE: PRT
<213> ORGANISM: artificial sequence
<220> FEATURE:
<223> OTHER INFORMATION: Description of Artificial Sequence: synthetic
module

<400> SEQUENCE: 15

Arg Ser Gly Ala Tyr Asp Tyr
1 5

<210> SEQ ID NO 16
<211> LENGTH: 8
<212> TYPE: PRT
<213> ORGANISM: artificial sequence
<220> FEATURE:
<223> OTHER INFORMATION: Description of Artificial Sequence: synthetic
module

<400> SEQUENCE: 16

Gln Gln Tyr Ser Ser Phe Pro Leu
1 5

<210> SEQ ID NO 17
<211> LENGTH: 11
<212> TYPE: PRT
<213> ORGANISM: artificial sequence
<220> FEATURE:
<223> OTHER INFORMATION: Description of Artificial Sequence: synthetic
module

<400> SEQUENCE: 17

Phe Asp Pro Phe Phe Asp Ser Phe Phe Asp Tyr
1 5 10

<210> SEQ ID NO 18
<211> LENGTH: 10
<212> TYPE: PRT
<213> ORGANISM: artificial sequence
<220> FEATURE:
<223> OTHER INFORMATION: Description of Artificial Sequence: synthetic
module -continued

<400> SEQUENCE: 18

Gln Ser Tyr Asp Gln Asn Ala Leu Val Glu
1 5 10

<210> SEQ ID NO 19
<211> LENGTH: 13
<212> TYPE: PRT
<213> ORGANISM: artificial sequence
<220> FEATURE:
<223> OTHER INFORMATION: Description of Artificial Sequence: synthetic module

<400> SEQUENCE: 19

His Gly Tyr Arg Lys Tyr Tyr Thr Asp Met Phe Asp Val
1 5 10

<210> SEQ ID NO 20
<211> LENGTH: 8
<212> TYPE: PRT
<213> ORGANISM: artificial sequence
<220> FEATURE:
<223> OTHER INFORMATION: Description of Artificial Sequence: synthetic module

<400> SEQUENCE: 20

His Gln Val Tyr Ser Thr Ser Pro
1 5

<210> SEQ ID NO 21
<211> LENGTH: 11
<212> TYPE: PRT
<213> ORGANISM: artificial sequence
<220> FEATURE:
<223> OTHER INFORMATION: Description of Artificial Sequence: synthetic module

<400> SEQUENCE: 21

Phe Pro Tyr Thr Tyr His Gly Phe Met Asp Asn
1 5 10

<210> SEQ ID NO 22
<211> LENGTH: 8
<212> TYPE: PRT
<213> ORGANISM: artificial sequence
<220> FEATURE:
<223> OTHER INFORMATION: Description of Artificial Sequence: synthetic module

<400> SEQUENCE: 22

Gln Ser Tyr Asp Ser Gly Asn Leu
1 5

<210> SEQ ID NO 23
<211> LENGTH: 434
<212> TYPE: PRT
<213> ORGANISM: artificial sequence
<220> FEATURE:
<223> OTHER INFORMATION: Description of Artificial Sequence: synthetic module

<400> SEQUENCE: 23

Met Lys Lys Thr Ala Ile Ala Ile Ala Val Ala Leu Ala Gly Phe Ala
1 5 10 15

Thr Val Ala Gln Ala Asp Tyr Cys Asp Ile Glu Phe Ala Glu Thr Val
20 25 30

-continued

```
Glu Ser Cys Leu Ala Lys Pro His Thr Glu Asn Ser Phe Thr Asn Val
        35                  40                  45

Trp Lys Asp Asp Lys Thr Leu Asp Arg Tyr Ala Asn Tyr Glu Gly Cys
    50                  55                  60

Leu Trp Asn Ala Thr Gly Val Val Val Cys Thr Gly Asp Glu Thr Gln
65                  70                  75                  80

Cys Tyr Gly Thr Trp Val Pro Ile Gly Leu Ala Ile Pro Glu Asn Glu
                85                  90                  95

Gly Gly Gly Ser Glu Gly Gly Gly Ser Glu Gly Gly Gly Ser Glu Gly
            100                 105                 110

Gly Gly Thr Lys Pro Pro Glu Tyr Gly Asp Thr Pro Ile Pro Gly Tyr
        115                 120                 125

Thr Tyr Ile Asn Pro Leu Asp Gly Thr Tyr Pro Pro Gly Thr Glu Gln
    130                 135                 140

Asn Pro Ala Asn Pro Asn Pro Ser Leu Glu Glu Ser Gln Pro Leu Asn
145                 150                 155                 160

Thr Phe Met Phe Gln Asn Asn Arg Phe Arg Asn Arg Gln Gly Ala Leu
                165                 170                 175

Thr Val Tyr Thr Gly Thr Val Thr Gln Gly Thr Asp Pro Val Lys Thr
            180                 185                 190

Tyr Tyr Gln Tyr Thr Pro Val Ser Ser Lys Ala Met Tyr Asp Ala Tyr
        195                 200                 205

Trp Asn Gly Lys Phe Arg Asp Cys Ala Phe His Ser Gly Phe Asn Glu
    210                 215                 220

Asp Pro Phe Val Cys Glu Tyr Gln Gly Gln Ser Ser Asp Leu Pro Gln
225                 230                 235                 240

Pro Pro Val Asn Ala Gly Gly Gly Ser Gly Gly Gly Ser Gly Gly Gly
                245                 250                 255

Ser Glu Gly Gly Gly Ser Glu Gly Gly Gly Ser Glu Gly Gly Gly Ser
            260                 265                 270

Glu Gly Gly Gly Ser Gly Gly Gly Ser Gly Ser Gly Asp Phe Asp Tyr
        275                 280                 285

Glu Lys Met Ala Asn Ala Asn Lys Gly Ala Met Thr Glu Asn Ala Asp
    290                 295                 300

Glu Asn Ala Leu Gln Ser Asp Ala Lys Gly Lys Leu Asp Ser Val Ala
305                 310                 315                 320

Thr Asp Tyr Gly Ala Ala Ile Asp Gly Phe Ile Gly Asp Val Ser Gly
                325                 330                 335

Leu Ala Asn Gly Asn Gly Ala Thr Gly Asp Phe Ala Gly Ser Asn Ser
            340                 345                 350

Gln Met Ala Gln Val Gly Asp Gly Asp Asn Ser Pro Leu Met Asn Asn
        355                 360                 365

Phe Arg Gln Tyr Leu Pro Ser Leu Pro Gln Ser Val Glu Cys Arg Pro
    370                 375                 380

Tyr Val Phe Gly Ala Gly Lys Pro Tyr Glu Phe Ser Ile Asp Cys Asp
385                 390                 395                 400

Lys Ile Asn Leu Phe Arg Gly Val Phe Ala Phe Leu Leu Tyr Val Ala
                405                 410                 415

Thr Phe Met Tyr Val Phe Ser Thr Phe Ala Asn Ile Leu Arg Asn Lys
            420                 425                 430

Glu Ser
```

<210> SEQ ID NO 24

-continued

<211> LENGTH: 219
<212> TYPE: PRT
<213> ORGANISM: artificial sequence
<220> FEATURE:
<223> OTHER INFORMATION: Description of Artificial Sequence: synthetic module

<400> SEQUENCE: 24

Met Lys Lys Thr Ala Ile Ala Ile Ala Val Ala Leu Ala Gly Phe Ala
1 5 10 15

Thr Val Ala Gln Ala Asp Tyr Cys Asp Ile Glu Phe Asn Ala Gly Gly
20 25 30

Gly Ser Gly Gly Gly Ser Gly Gly Gly Ser Glu Gly Gly Gly Ser Glu
35 40 45

Gly Gly Gly Ser Glu Gly Gly Gly Ser Glu Gly Gly Gly Ser Gly Gly
50 55 60

Gly Ser Gly Ser Gly Asp Phe Asp Tyr Glu Lys Met Ala Asn Ala Asn
65 70 75 80

Lys Gly Ala Met Thr Glu Asn Ala Asp Glu Asn Ala Leu Gln Ser Asp
85 90 95

Ala Lys Gly Lys Leu Asp Ser Val Ala Thr Asp Tyr Gly Ala Ala Ile
100 105 110

Asp Gly Phe Ile Gly Asp Val Ser Gly Leu Ala Asn Gly Asn Gly Ala
115 120 125

Thr Gly Asp Phe Ala Gly Ser Asn Ser Gln Met Ala Gln Val Gly Asp
130 135 140

Gly Asp Asn Ser Pro Leu Met Asn Asn Phe Arg Gln Tyr Leu Pro Ser
145 150 155 160

Leu Pro Gln Ser Val Glu Cys Arg Pro Phe Val Phe Gly Ala Gly Lys
165 170 175

Pro Tyr Glu Phe Ser Ile Asp Cys Asp Lys Ile Asn Leu Phe Arg Gly
180 185 190

Val Phe Ala Phe Leu Leu Tyr Val Ala Thr Phe Met Tyr Val Phe Ser
195 200 205

Thr Phe Ala Asn Ile Leu Arg Asn Lys Glu Ser
210 215

<210> SEQ ID NO 25
<211> LENGTH: 432
<212> TYPE: PRT
<213> ORGANISM: artificial sequence
<220> FEATURE:
<223> OTHER INFORMATION: Description of Artificial Sequence: synthetic module

<400> SEQUENCE: 25

Met Lys Lys Leu Leu Phe Ala Ile Pro Leu Val Val Pro Phe Tyr Ser
1 5 10 15

His Ser Thr Met Ala Cys Asp Ile Glu Phe Ala Glu Thr Val Glu Ser
20 25 30

Cys Leu Ala Lys Pro His Thr Glu Asn Ser Phe Thr Asn Val Trp Lys
35 40 45

Asp Asp Lys Thr Leu Asp Arg Tyr Ala Asn Tyr Glu Gly Cys Leu Trp
50 55 60

Asn Ala Thr Gly Val Val Val Cys Thr Gly Asp Glu Thr Gln Cys Tyr
65 70 75 80

Gly Thr Trp Val Pro Ile Gly Leu Ala Ile Pro Glu Asn Glu Gly Gly
85 90 95

-continued

```
Gly Ser Glu Gly Gly Gly Ser Glu Gly Gly Gly Ser Glu Gly Gly Gly
            100                 105                 110

Thr Lys Pro Pro Glu Tyr Gly Asp Thr Pro Ile Pro Gly Tyr Thr Tyr
        115                 120                 125

Ile Asn Pro Leu Asp Gly Thr Tyr Pro Pro Gly Thr Glu Gln Asn Pro
    130                 135                 140

Ala Asn Pro Asn Pro Ser Leu Glu Glu Ser Gln Pro Leu Asn Thr Phe
145                 150                 155                 160

Met Phe Gln Asn Asn Arg Phe Arg Asn Arg Gln Gly Ala Leu Thr Val
                165                 170                 175

Tyr Thr Gly Thr Val Thr Gln Gly Thr Asp Pro Val Lys Thr Tyr Tyr
            180                 185                 190

Gln Tyr Thr Pro Val Ser Ser Lys Ala Met Tyr Asp Ala Tyr Trp Asn
        195                 200                 205

Gly Lys Phe Arg Asp Cys Ala Phe His Ser Gly Phe Asn Glu Asp Pro
    210                 215                 220

Phe Val Cys Glu Tyr Gln Gly Gln Ser Ser Asp Leu Pro Gln Pro Pro
225                 230                 235                 240

Val Asn Ala Gly Gly Gly Ser Gly Gly Gly Ser Gly Gly Gly Ser Glu
                245                 250                 255

Gly Gly Gly Ser Glu Gly Gly Gly Ser Glu Gly Gly Gly Ser Glu Gly
            260                 265                 270

Gly Gly Ser Gly Gly Gly Ser Gly Ser Gly Asp Phe Asp Tyr Glu Lys
        275                 280                 285

Met Ala Asn Ala Asn Lys Gly Ala Met Thr Glu Asn Ala Asp Glu Asn
    290                 295                 300

Ala Leu Gln Ser Asp Ala Lys Gly Lys Leu Asp Ser Val Ala Thr Asp
305                 310                 315                 320

Tyr Gly Ala Ala Ile Asp Gly Phe Ile Gly Asp Val Ser Gly Leu Ala
                325                 330                 335

Asn Gly Asn Gly Ala Thr Gly Asp Phe Ala Gly Ser Asn Ser Gln Met
            340                 345                 350

Ala Gln Val Gly Asp Gly Asp Asn Ser Pro Leu Met Asn Asn Phe Arg
        355                 360                 365

Gln Tyr Leu Pro Ser Leu Pro Gln Ser Val Glu Cys Arg Pro Tyr Val
    370                 375                 380

Phe Gly Ala Gly Lys Pro Tyr Glu Phe Ser Ile Asp Cys Asp Lys Ile
385                 390                 395                 400

Asn Leu Phe Arg Gly Val Phe Ala Phe Leu Leu Tyr Val Ala Thr Phe
                405                 410                 415

Met Tyr Val Phe Ser Thr Phe Ala Asn Ile Leu Arg Asn Lys Glu Ser
            420                 425                 430
```

<210> SEQ ID NO 26
<211> LENGTH: 434
<212> TYPE: PRT
<213> ORGANISM: artificial sequence
<220> FEATURE:
<223> OTHER INFORMATION: Description of Artificial Sequence: synthetic module

<400> SEQUENCE: 26

```
Met Lys Lys Thr Ala Ile Ala Ile Ala Val Ala Leu Ala Gly Phe Ala
1               5                   10                  15

Thr Val Ala Gln Ala Asp Tyr Cys Asp Ile Glu Phe Ala Glu Thr Val
```

-continued

```
            20                  25                  30

Glu Ser Cys Leu Ala Lys Pro His Thr Glu Asn Ser Phe Thr Asn Val
        35                  40                  45

Trp Lys Asp Asp Lys Thr Leu Asp Arg Tyr Ala Asn Tyr Glu Gly Cys
    50                  55                  60

Leu Trp Asn Ala Thr Gly Val Val Val Cys Thr Gly Asp Glu Thr Gln
65                  70                  75                  80

Cys Tyr Gly Thr Trp Val Pro Ile Gly Leu Ala Ile Pro Glu Asn Glu
                85                  90                  95

Gly Gly Gly Ser Glu Gly Gly Gly Ser Glu Gly Gly Gly Ser Glu Gly
            100                 105                 110

Gly Gly Thr Lys Pro Pro Glu Tyr Gly Asp Thr Pro Ile Pro Gly Tyr
        115                 120                 125

Thr Tyr Ile Asn Pro Leu Asp Gly Thr Tyr Pro Pro Gly Thr Glu Gln
    130                 135                 140

Asn Pro Ala Asn Pro Asn Pro Ser Leu Glu Glu Ser Gln Pro Leu Asn
145                 150                 155                 160

Thr Phe Met Phe Gln Asn Asn Arg Phe Arg Asn Arg Gln Gly Ala Leu
                165                 170                 175

Thr Val Tyr Thr Gly Thr Val Thr Gln Gly Thr Asp Pro Val Lys Thr
            180                 185                 190

Tyr Tyr Gln Tyr Thr Pro Val Ser Ser Lys Ala Met Tyr Asp Ala Tyr
        195                 200                 205

Trp Asn Gly Lys Phe Arg Asp Cys Ala Phe His Ser Gly Phe Asn Glu
    210                 215                 220

Asp Pro Phe Val Cys Glu Tyr Gln Gly Gln Ser Ser Asp Leu Pro Gln
225                 230                 235                 240

Pro Pro Val Asn Ala Gly Gly Gly Ser Gly Gly Gly Ser Gly Gly Gly
                245                 250                 255

Ser Glu Gly Gly Gly Ser Glu Gly Gly Gly Ser Glu Gly Gly Gly Ser
            260                 265                 270

Glu Gly Gly Gly Ser Gly Gly Gly Ser Gly Ser Gly Asp Phe Asp Tyr
        275                 280                 285

Glu Lys Met Ala Asn Ala Asn Lys Gly Ala Met Thr Glu Asn Ala Asp
    290                 295                 300

Glu Asn Ala Leu Gln Ser Asp Ala Lys Gly Lys Leu Asp Ser Val Ala
305                 310                 315                 320

Thr Asp Tyr Gly Ala Ala Ile Asp Gly Phe Ile Gly Asp Val Ser Gly
                325                 330                 335

Leu Ala Asn Gly Asn Gly Ala Thr Gly Asp Phe Ala Gly Ser Asn Ser
            340                 345                 350

Gln Met Ala Gln Val Gly Asp Gly Asp Asn Ser Pro Leu Met Asn Asn
        355                 360                 365

Phe Arg Gln Tyr Leu Pro Ser Leu Pro Gln Ser Val Glu Cys Arg Pro
    370                 375                 380

Tyr Val Phe Gly Ala Gly Lys Pro Tyr Glu Phe Ser Ile Asp Cys Asp
385                 390                 395                 400

Lys Ile Asn Leu Phe Arg Gly Val Phe Ala Phe Leu Leu Tyr Val Ala
                405                 410                 415

Thr Phe Met Tyr Val Phe Ser Thr Phe Ala Asn Ile Leu Arg Asn Lys
            420                 425                 430

Glu Ser
```

-continued

```
<210> SEQ ID NO 27
<211> LENGTH: 219
<212> TYPE: PRT
<213> ORGANISM: artificial sequence
<220> FEATURE:
<223> OTHER INFORMATION: Description of Artificial Sequence: synthetic
      module

<400> SEQUENCE: 27

Met Lys Lys Thr Ala Ile Ala Ile Ala Val Ala Leu Ala Gly Phe Ala
1               5                   10                  15

Thr Val Ala Gln Ala Asp Tyr Cys Asp Ile Glu Phe Asn Ala Gly Gly
            20                  25                  30

Gly Ser Gly Gly Gly Ser Gly Gly Gly Ser Glu Gly Gly Gly Ser Glu
        35                  40                  45

Gly Gly Gly Ser Glu Gly Gly Gly Ser Glu Gly Gly Gly Ser Gly Gly
    50                  55                  60

Gly Ser Gly Ser Gly Asp Phe Asp Tyr Glu Lys Met Ala Asn Ala Asn
65                  70                  75                  80

Lys Gly Ala Met Thr Glu Asn Ala Asp Glu Asn Ala Leu Gln Ser Asp
                85                  90                  95

Ala Lys Gly Lys Leu Asp Ser Val Ala Thr Asp Tyr Gly Ala Ala Ile
            100                 105                 110

Asp Gly Phe Ile Gly Asp Val Ser Gly Leu Ala Asn Gly Asn Gly Ala
        115                 120                 125

Thr Gly Asp Phe Ala Gly Ser Asn Ser Gln Met Ala Gln Val Gly Asp
    130                 135                 140

Gly Asp Asn Ser Pro Leu Met Asn Asn Phe Arg Gln Tyr Leu Pro Ser
145                 150                 155                 160

Leu Pro Gln Ser Val Glu Cys Arg Pro Phe Val Phe Gly Ala Gly Lys
                165                 170                 175

Pro Tyr Glu Phe Ser Ile Asp Cys Asp Lys Ile Asn Leu Phe Arg Gly
            180                 185                 190

Val Phe Ala Phe Leu Leu Tyr Val Ala Thr Phe Met Tyr Val Phe Ser
        195                 200                 205

Thr Phe Ala Asn Ile Leu Arg Asn Lys Glu Ser
    210                 215


<210> SEQ ID NO 28
<211> LENGTH: 65
<212> TYPE: PRT
<213> ORGANISM: artificial sequence
<220> FEATURE:
<223> OTHER INFORMATION: Description of Artificial Sequence: synthetic
      module

<400> SEQUENCE: 28

Met Lys Lys Thr Ala Ile Ala Ile Ala Val Ala Leu Ala Gly Phe Ala
1               5                   10                  15

Thr Val Ala Gln Ala Asp Tyr Cys Asp Ile Glu Phe Gly Gly Gly Gly
            20                  25                  30

Ser Met Ser Val Leu Val Tyr Ser Phe Ala Ser Phe Val Leu Gly Trp
        35                  40                  45

Cys Leu Arg Ser Gly Ile Thr Tyr Phe Thr Arg Leu Met Glu Thr Ser
    50                  55                  60

Ser
65
```

-continued

```
<210> SEQ ID NO 29
<211> LENGTH: 16
<212> TYPE: PRT
<213> ORGANISM: artificial sequence
<220> FEATURE:
<223> OTHER INFORMATION: Description of Artificial Sequence: synthetic
      module

<400> SEQUENCE: 29

Ser Pro Gly Gly Ser Gly Gly Ala Pro His His His His His His Cys
1               5                   10                  15


<210> SEQ ID NO 30
<211> LENGTH: 21
<212> TYPE: PRT
<213> ORGANISM: artificial sequence
<220> FEATURE:
<223> OTHER INFORMATION: Description of Artificial Sequence: synthetic
      module

<400> SEQUENCE: 30

Glu Phe Asp Tyr Lys Asp Asp Asp Asp Lys Gly Ala Pro Trp Ser His
1               5                   10                  15

Pro Gln Phe Glu Lys
            20


<210> SEQ ID NO 31
<211> LENGTH: 24
<212> TYPE: PRT
<213> ORGANISM: artificial sequence
<220> FEATURE:
<223> OTHER INFORMATION: Description of Artificial Sequence: synthetic
      module

<400> SEQUENCE: 31

Glu Phe Glu Gln Lys Leu Ile Ser Glu Glu Asp Leu Asn Gly Ala Pro
1               5                   10                  15

Trp Ser His Pro Gln Phe Glu Lys
            20


<210> SEQ ID NO 32
<211> LENGTH: 17
<212> TYPE: PRT
<213> ORGANISM: artificial sequence
<220> FEATURE:
<223> OTHER INFORMATION: Description of Artificial Sequence: synthetic
      module

<400> SEQUENCE: 32

Glu Phe Pro Gly Gly Ser Gly Gly Ala Pro His His His His His His
1               5                   10                  15

Cys


<210> SEQ ID NO 33
<211> LENGTH: 22
<212> TYPE: PRT
<213> ORGANISM: artificial sequence
<220> FEATURE:
<223> OTHER INFORMATION: Description of Artificial Sequence: synthetic
      module

<400> SEQUENCE: 33

Cys Glu Phe Asp Tyr Lys Asp Asp Asp Asp Lys Gly Ala Pro Trp Ser
1               5                   10                  15

His Pro Gln Phe Glu Lys
```

-continued

20

<210> SEQ ID NO 34
<211> LENGTH: 25
<212> TYPE: PRT
<213> ORGANISM: artificial sequence
<220> FEATURE:
<223> OTHER INFORMATION: Description of Artificial Sequence: synthetic module

<400> SEQUENCE: 34

Cys Glu Phe Glu Gln Lys Leu Ile Ser Glu Glu Asp Leu Asn Gly Ala
1 5 10 15

Pro Trp Ser His Pro Gln Phe Glu Lys
20 25

<210> SEQ ID NO 35
<211> LENGTH: 4380
<212> TYPE: DNA
<213> ORGANISM: artificial sequence
<220> FEATURE:
<223> OTHER INFORMATION: Description of Artificial Sequence: vector

<400> SEQUENCE: 35
tctagagcat gcgtaggaga aaataaaatg aaacaaagca ctattgcact ggcactctta 60
ccgttgctct tcacccctgt taccaaagcc gactacaaag atgaagtgca attggtggaa 120
agcggcggcg gcctggtgca accgggcggc agcctgcgtc tgagctgcgc ggcctccgga 180
tttaccttta gcagctatgc gatgagctgg gtgcgccaag cccctgggaa gggtctcgag 240
tgggtgagcg cgattagcgg tagcggcggc agcacctatt atgcggatag cgtgaaaggc 300
cgttttacca tttcacgtga taattcgaaa aacaccctgt atctgcaaat gaacagcctg 360
cgtgcggaag atacggccgt gtattattgc gcgcgtcgtt ctggtgctta tgattattgg 420
ggccaaggca ccctggtgac ggttagctca gcgggtggcg gttctggcgg cggtgggagc 480
ggtggcggtg gttctggcgg tggtggttcc gatatcgtga tgacccagag cccggatagc 540
ctggcggtga gcctgggcga acgtgcgacc attaactgca gaagcagcca gagcgtgctg 600
tatagcagca acaacaaaaa ctatctggcg tggtaccagc agaaaccagg tcagccgccg 660
aaactattaa tttattgggc atccacccgt gaaagcgggg tcccggatcg ttttagcggc 720
tctggatccg gcactgattt taccctgacc atttcgtccc tgcaagctga agacgtggcg 780
gtgtattatt gccagcagta ttcttctttt cctcttacct ttggccaggg tacgaaagtt 840
gaaattaaac gtacggaatt cccagggggg agcggaggcg cgccgcacca tcatcaccat 900
cactgataag cttgacctgt gaagtgaaaa atggcgcaga ttgtgcgaca tttttttttgt 960 ctgccgttta attaaagggg ggggggggcc ggcctggggg ggggtgtaca tgaaattgta 1020
aacgttaata ttttgttaaa attcgcgtta aatttttgtt aaatcagctc attttttaac 1080
caataggccg aaatcggcaa aatcccttat aaatcaaaag aatagaccga gatagggttg 1140
agtgttgttc cagtttggaa caagagtcca ctattaaaga acgtggactc caacgtcaaa 1200
gggcgaaaaa ccgtctatca gggcgatggc ccactacgag aaccatcacc ctaatcaagt 1260
tttttggggt cgaggtgccg taaagcacta aatcggaacc ctaaagggag cccccgattt 1320
agagcttgac ggggaaagcc ggcgaacgtg gcgagaaagg aagggaagaa agcgaaagga 1380
gcgggcgcta gggcgctggc aagtgtagcg gtcacgctgc gcgtaaccac cacacccgcc 1440
gcgcttaatg cgccgctaca gggcgcgtgc tagactagtg tttaaaccgg accggggggg 1500

-continued

```
ggcttaagtg ggctgcaaaa caaaacggcc tcctgtcagg aagccgcttt tatcgggtag   1560
cctcactgcc cgctttccag tcgggaaacc tgtcgtgcca gctgcatcag tgaatcggcc   1620
aacgcgcggg gagaggcggt ttgcgtattg ggagccaggg tggtttttct tttcaccagt   1680
gagacgggca acagctgatt gcccttcacc gcctggccct gagagagttg cagcaagcgg   1740
tccacgctgg tttgccccag caggcgaaaa tcctgtttga tggtggtcag cggcgggata   1800
taacatgagc tgtcctcggt atcgtcgtat cccactaccg agatgtccgc accaacgcgc   1860
agcccggact cggtaatggc acgcattgcg cccagcgcca tctgatcgtt ggcaaccagc   1920
atcgcagtgg gaacgatgcc ctcattcagc atttgcatgg tttgttgaaa accggacatg   1980
gcactccagt cgccttcccg ttccgctatc ggctgaattt gattgcgagt gagatattta   2040
tgccagccag ccagacgcag acgcgccgag acagaactta atgggccagc taacagcgcg   2100
atttgctggt ggcccaatgc gaccagatgc tccacgccca gtcgcgtacc gtcctcatgg   2160
gagaaaataa tactgttgat gggtgtctgg tcagagacat caagaaataa cgccggaaca   2220
ttagtgcagg cagcttccac agcaatagca tcctggtcat ccagcggata gttaataatc   2280
agcccactga cacgttgcgc gagaagattg tgcaccgccg ctttacaggc ttcgacgccg   2340
cttcgttcta ccatcgacac gaccacgctg gcacccagtt gatcggcgcg agatttaatc   2400
gccgcgacaa tttgcgacgg cgcgtgcagg gccagactgg aggtggcaac gccaatcagc   2460
aacgactgtt tgcccgccag ttgttgtgcc acgcggttag gaatgtaatt cagctccgcc   2520
atcgccgctt ccactttttc ccgcgttttc gcagaaacgt ggctggcctg gttcaccacg   2580
cgggaaacgg tctgataaga gacaccggca tactctgcga catcgtataa cgttactggt   2640
ttcacattca ccaccctgaa ttgactctct tccgggcgct atcatgccat accgcgaaag   2700
gttttgcgcc attcgatgct agccatgtga gcaaaaggcc agcaaaaggc caggaaccgt   2760
aaaaaggccg cgttgctggc gtttttccat aggctccgcc cccctgacga gcatcacaaa   2820
aatcgacgct caagtcagag gtggcgaaac ccgacaggac tataaagata ccaggcgttt   2880
ccccctggaa gctccctcgt gcgctctcct gttccgaccc tgccgcttac cggatacctg   2940
tccgcctttc tcccttcggg aagcgtggcg ctttctcata gctcacgctg taggtatctc   3000
agttcggtgt aggtcgttcg ctccaagctg ggctgtgtgc acgaaccccc cgttcagccc   3060
gaccgctgcg ccttatccgg taactatcgt cttgagtcca acccggtaag acacgactta   3120
tcgccactgg cagcagccac tggtaacagg attagcagag cgaggtatgt aggcggtgct   3180
acagagttct tgaagtggtg gcctaactac ggctacacta gaagaacagt atttggtatc   3240
tgcgctctgc tgtagccagt taccttcgga aaaagagttg gtagctcttg atccggcaaa   3300
caaaccaccg ctggtagcgg tggttttttt gtttgcaagc agcagattac gcgcagaaaa   3360
aaaggatctc aagaagatcc tttgatcttt tctacggggt ctgacgctca gtggaacgaa   3420
aactcacgtt aagggatttt ggtcagatct agcaccaggc gtttaagggc accaataact   3480
gccttaaaaa aattacgccc cgccctgcca ctcatcgcag tactgttgta attcattaag   3540
cattctgccg acatggaagc catcacaaac ggcatgatga acctgaatcg ccagcggcat   3600
cagcaccttg tcgccttgcg tataatattt gcccatagtg aaaacggggg cgaagaagtt   3660
gtccatattg gctacgttta aatcaaaact ggtgaaactc acccagggat tggctgagac   3720
gaaaaacata ttctcaataa accctttagg gaaataggcc aggttttcac cgtaacacgc   3780
cacatcttgc gaatatatgt gtagaaactg ccggaaatcg tcgtggtatt cactccagag   3840
cgatgaaaac gtttcagttt gctcatggaa aacggtgtaa caagggtgaa cactatccca   3900
```

-continued

```
tatcaccagc tcaccgtctt tcattgccat acggaactcc gggtgagcat tcatcaggcg   3960

ggcaagaatg tgaataaagg ccggataaaa cttgtgctta tttttcttta cggtctttaa   4020

aaaggccgta atatccagct gaacggtctg gttataggta cattgagcaa ctgactgaaa   4080

tgcctcaaaa tgttctttac gatgccattg ggatatatca acggtggtat atccagtgat   4140

ttttttctcc attttagctt ccttagctcc tgaaaatctc gataactcaa aaaatacgcc   4200

cggtagtgat cttatttcat tatggtgaaa gttggaacct cacccgacgt ctaatgtgag   4260

ttagctcact cattaggcac cccaggcttt acactttatg cttccggctc gtatgttgtg   4320

tggaattgtg agcggataac aatttcacac aggaaacagc tatgaccatg attacgaatt   4380
```

<210> SEQ ID NO 36
<211> LENGTH: 2839
<212> TYPE: DNA
<213> ORGANISM: artificial sequence
<220> FEATURE:
<223> OTHER INFORMATION: Description of Artificial Sequence: vector

<400> SEQUENCE: 36

```
acccgacacc atcgaaatta atacgactca ctatagggag accacaacgg tttcccgaat     60

tgtgagcgga taacaataga aataattttg tttaacttta agaaggagat atatccatgg    120

ctgaaactgt tgaaagttgt ttagcaaaat cccatacaga aaattcattt actaacgtct    180

ggaaagacga caaaacttta gatcgttacg ctaactatga gggctgtctg tggaatgcta    240

caggcgttgt agtttgtact ggtgacgaaa ctcagtgtta cggtacatgg gttcctattg    300

ggcttgctat ccctgaaaat gagggtggtg gctctgaggg tggcggttct ccgtacgacg    360

ttccagacta cgcttccctg cgttcccatc accatcacca tcactaagct tcagtcccgg    420

gcagtggatc cggctgctaa caaagcccga aaggaagctg agttggctgc tgccaccgct    480

gagcaataac tagcataacc ccttggggcc tctaaacggg tcttgagggg ttttttgctg    540

aaaggaggaa ctatatccgg atcgagatcc ccacgcgccc tgtagcggcg cattaagcgc    600

ggcgggtgtg gtggttacgc gcagcgtgac cgctacactt gccagcgccc tagcgcccgc    660

tcctttcgct ttcttccctt cctttctcgc cacgttcgcc ggctttcccc gtcaagctct    720

aaatcggggc atccctttag ggttccgatt tagtgcttta cggcacctcg accccaaaaa    780

acttgattag ggtgatggtt cacgtagtgg gccatcgccc tgatagacgg tttttcgccc    840

tttgacgttg gagtccacgt tctttaatag tggactcttg ttccaaactg gaacaacact    900

caaccctatc tcggtctatt cttttgattt ataagggatt ttgccgattt cggcctattg    960

gttaaaaaat gagctgattt aacaaaaatt taacgcgaat tttaacaaaa tattaacgtt   1020

tacaatttca ggtggcactt ttcggggaaa tgtgcgcgga acccctattt gtttattttt   1080

ctaaatacat tcaaatatgt atccgctcat gagacaataa ccctgataaa tgcttcaata   1140

atattgaaaa aggaagagta tgagtattca acatttccgt gtcgccctta ttcccttttt   1200

tgcggcattt tgccttcctg tttttgctca cccagaaacg ctggtgaaag taaaagatgc   1260

tgaagatcag ttgggtgcac gagtgggtta catcgaactg gatctcaaca gcggtaagat   1320

ccttgagagt tttcgccccg aagaacgttt tccaatgatg agcactttta aagttctgct   1380

atgtggcgcg gtattatccc gtattgacgc cgggcaagag caactcggtc gccgcataca   1440

ctattctcag aatgacttgg ttgagtactc accagtcaca gaaaagcatc ttacggatgg   1500

catgacagta agagaattat gcagtgctgc cataaccatg agtgataaca ctgcggccaa   1560
```

-continued cttacttctg acaacgatcg gaggaccgaa ggagctaacc gcttttttgc acaacatggg 1620
ggatcatgta actcgccttg atcgttggga accggagctg aatgaagcca taccaaacga 1680
cgagcgtgac accacgatgc ctgtagcaat ggcaacaacg ttgcgcaaac tattaactgg 1740
cgaactactt actctagctt cccggcaaca attaatagac tggatggagg cggataaagt 1800
tgcaggacca cttctgcgct cggcccttcc ggctggctgg tttattgctg ataaatctgg 1860
agccggtgag cgtgggtctc gcggtatcat tgcagcactg gggccagatg gtaagccctc 1920
ccgtatcgta gttatctaca cgacggggag tcaggcaact atggatgaac gaaatagaca 1980
gatcgctgag ataggtgcct cactgattaa gcattggtaa ctgtcagacc aagtttactc 2040
atatatactt tagattgatt taaaacttca tttttaattt aaaaggatct aggtgaagat 2100
cctttttgat aatctcatga ccaaaatccc ttaacgtgag ttttcgttcc actgagcgtc 2160
agaccccgta gaaaagatca aaggatcttc ttgagatcct ttttttctgc gcgtaatctg 2220
ctgcttgcaa acaaaaaaac caccgctacc agcggtggtt tgtttgccgg atcaagagct 2280
accaactctt tttccgaagg taactggctt cagcagagcg cagataccaa atactgtcct 2340
tctagtgtag ccgtagttag gccaccactt caagaactct gtagcaccgc ctacatacct 2400
cgctctgcta atcctgttac cagtggctgc tgccagtggc gataagtcgt gtcttaccgg 2460
gttggactca agacgatagt taccggataa ggcgcagcgg tcgggctgaa cggggggttc 2520
gtgcacacag cccagcttgg agcgaacgac ctacaccgaa ctgagatacc tacagcgtga 2580
gctatgagaa agcgccacgc ttcccgaagg gagaaaggcg gacaggtatc cggtaagcgg 2640
cagggtcgga acaggagagc gcacgaggga gcttccaggg ggaaacgcct ggtatcttta 2700
tagtcctgtc gggtttcgcc acctctgact tgagcgtcga tttttgtgat gctcgtcagg 2760
ggggcggagc ctatggaaaa acgccagcaa cgcggccttt ttacggttcc tggccttttg 2820
ctggcctttt gctcacatg 2839

<210> SEQ ID NO 37
<211> LENGTH: 4045
<212> TYPE: DNA
<213> ORGANISM: artificial sequence
<220> FEATURE:
<223> OTHER INFORMATION: Description of Artificial Sequence: vector

<400> SEQUENCE: 37
agcttaatta gctgagcttg gactcctgtt gatagatcca gtaatgacct cagaactcca 60
tctggatttg ttcagaacgc tcggttgccg ccgggcgttt tttattggtg agaatccaag 120
ctagcttggc gagattttca ggagctaagg aagctaaaat ggagaaaaaa atcactggat 180
ataccaccgt tgatatatcc caatggcatc gtaaagaaca ttttgaggca tttcagtcag 240
ttgctcaatg tacctataac cagaccgttc agctggatat tacggccttt ttaaagaccg 300
taaagaaaaa taagcacaag ttttatccgg cctttattca cattcttgcc cgcctgatga 360
atgctcatcc ggaatttcgt atggcaatga aagacggtga gctggtgata tgggatagtg 420
ttcacccttg ttacaccgtt ttccatgagc aaactgaaac gttttcatcg ctctggagtg 480
aataccacga cgatttccgg cagtttctac acatatattc gcaagatgtg gcgtgttacg 540
gtgaaaacct ggcctatttc cctaaagggt ttattgagaa tatgtttttc gtctcagcca 600
atccctgggt gagtttcacc agttttgatt taaacgtggc caatatggac aacttcttcg 660
cccccgtttt caccatgcat gggcaaatat tatacgcaag gcgacaaggt gctgatgccg 720
ctggcgattc aggttcatca tgccgtctgt gatggcttcc atgtcggcag aatgcttaat 780

-continued

```
gaattacaac agtactgcga tgagtggcag ggcggggcgt aattttttta aggcagttat    840
tggtgccctt aaacgcctgg ggtaatgact ctctagcttg aggcatcaaa taaaacgaaa    900
ggctcagtcg aaagactggg cctttcgttt tatctgttgt ttgtcggtga acgctctcct    960
gagtaggaca aatccgccgc tctagagctg cctcgcgcgt ttcggtgatg acggtgaaaa   1020
cctctgacac atgcagctcc cggagacggt cacagcttgt ctgtaagcgg atgccgggag   1080
cagacaagcc cgtcagggcg cgtcagcggg tgttggcggg tgtcggggcg cagccatgac   1140
ccagtcacgt agcgatagcg gagtgtatac tggcttaact atgcggcatc agagcagatt   1200
gtactgagag tgcaccatat gcggtgtgaa ataccgcaca gatgcgtaag gagaaaatac   1260
cgcatcaggc gctcttccgc ttcctcgctc actgactcgc tgcgctcggt ctgtcggctg   1320
cggcgagcgg tatcagctca ctcaaaggcg gtaatacggt tatccacaga atcaggggat   1380
aacgcaggaa agaacatgtg agcaaaaggc cagcaaaagg ccaggaaccg taaaaaggcc   1440
gcgttgctgg cgtttttcca taggctccgc ccccctgacg agcatcacaa aaatcgacgc   1500
tcaagtcaga ggtggcgaaa cccgacagga ctataaagat accaggcgtt tccccctgga   1560
agctccctcg tgcgctctcc tgttccgacc ctgccgctta ccggatacct gtccgccttt   1620
ctcccttcgg gaagcgtggc gctttctcaa tgctcacgct gtaggtatct cagttcggtg   1680
taggtcgttc gctccaagct gggctgtgtg cacgaacccc ccgttcagcc cgaccgctgc   1740
gccttatccg gtaactatcg tcttgagtcc aacccggtaa gacacgactt atcgccactg   1800
gcagcagcca ctggtaacag gattagcaga gcgaggtatg taggcggtgc tacagagttc   1860
ttgaagtggt ggcctaacta cggctacact agaaggacag tatttggtat ctgcgctctg   1920
ctgaagccag ttaccttcgg aaaaagagtt ggtagctctt gatccggcaa acaaaccacc   1980
gctggtagcg gtggtttttt tgtttgcaag cagcagatta cgcgcagaaa aaaaggatct   2040
caagaagatc ctttgatctt ttctacgggg tctgacgctc agtggaacga aaactcacgt   2100
taagggattt tggtcatgag attatcaaaa aggatcttca cctagatcct tttaaattaa   2160
aaatgaagtt ttaaatcaat ctaaagtata tatgagtaaa cttggtctga cagttaccaa   2220
tgcttaatca gtgaggcacc tatctcagcg atctgtctat ttcgttcatc catagctgcc   2280
tgactccccg tcgtgtagat aactacgata cgggagggct taccatctgg ccccagtgct   2340
gcaatgatac cgcgagaccc acgctcaccg gctccagatt tatcagcaat aaaccagcca   2400
gccggaaggg ccgagcgcag aagtggtcct gcaactttat ccgcctccat ccagtctatt   2460
aattgttgcc gggaagctag agtaagtagt tcgccagtta atagtttgcg caacgttgtt   2520
gccattgcta caggcatcgt ggtgtcacgc tcgtcgtttg gtatggcttc attcagctcc   2580
ggttcccaac gatcaaggcg agttacatga tcccccatgt tgtgcaaaaa agcggttagc   2640
tccttcggtc ctccgatcgt tgtcagaagt aagttggccg cagtgttatc actcatggtt   2700
atggcagcac tgcataattc tcttactgtc atgccatccg taagatgctt ttctgtgact   2760
ggtgagtact caaccaagtc attctgagaa tagtgtatgc ggcgaccgag ttgctcttgc   2820
ccggcgtcaa tacgggataa taccgcgcca catagcagaa ctttaaaagt gctcatcatt   2880
ggaaaacgtt cttcggggcg aaaactctca aggatcttac cgctgttgag atccagttcg   2940
atgtaaccca ctcgtgcacc caactgatct tcagcatctt ttactttcac cagcgtttct   3000
gggtgagcaa aaacaggaag gcaaaatgcc gcaaaaaagg gaataagggc gacacggaaa   3060
tgttgaatac tcatactctt cctttttcaa tattattgaa gcatttatca gggttattgt   3120
```

-continued

```
ctcatgagcg gatacatatt tgaatgtatt tagaaaaata aacaaatagg ggttccgcgc   3180

acatttcccc gaaaagtgcc acctgacgtc taagaaacca ttattatcat gacattaacc   3240

tataaaaata ggcgtatcac gaggcccttt cgtcttcacc tcgagaaatc ataaaaaatt   3300

tatttgcttt gtgagcggat aacaattata atagattcaa ttgtgagcgg ataacaattt   3360

cacacagaat tcattaaaga ggagaaatta accatgagtg acattgcctt cttgattgat   3420

ggctctggta gcatcatccc acatgacttt cggcggatga aggagtttgt ctcaactgtg   3480

atggagcaat taaaaaagtc caaaaccttg ttctctttga tgcagtactc tgaagaattc   3540

cggattcact ttaccttcaa agagttccag aacaacccta acccaagatc actggtgaag   3600

ccaataacgc agctgcttgg gcggacacac acggccacgg gcatccgcaa agtggtacga   3660

gagctgttta acatcaccaa cggagcccga aagaatgcct ttaagatcct agttgtcatc   3720

acggatggag aaaagtttgg cgatcccttg ggatatgagg atgtcatccc tgaggcagac   3780

agagagggag tcattcgcta cgtcattggg gtgggagatg ccttccgcag tgagaaatcc   3840

cgccaagagc ttaataccat cgcatccaag ccgcctcgtg atcacgtgtt ccaggtgaat   3900

aactttgagg ctctgaagac cattcagaac cagcttcggg agaagatctt tgcgatcgag   3960

ggtactcaga caggaagtag cagctccttt gagcatgaga tgtctcagga aatcgaaggt   4020

agacatcacc atcaccatca ctaga                                          4045
```

<210> SEQ ID NO 38
<211> LENGTH: 1574
<212> TYPE: DNA
<213> ORGANISM: artificial sequence
<220> FEATURE:
<223> OTHER INFORMATION: Description of Artificial Sequence: expression cassette

<400> SEQUENCE: 38

```
gctagcctga ggccagtttg ctcaggctct ccccgtggag gtaataattg ctcgaccgat     60

aaaagcggct tcctgacagg aggccgtttt gttttgcagc ccacctcaac gcaattaatg    120

tgagttagct cactcattag gcaccccagg ctttacactt tatgcttccg gctcgtatgt    180

tgtgtggaat tgtgagcgga taacaatttc acacaggaaa cagctatgac catgattacg    240

aatttctaga taacgagggc aaaaaatgaa aaagacagct atcgcgattg cagtggcact    300

ggctggtttc gctaccgtag cgcaggccga ctactgcgat atcgaattcg cagaaacagt    360

tgaaagttgt ttagcaaaac cccatacaga aaattcattt actaacgtct ggaaagacga    420

caaaacttta gatcgttacg ctaactatga gggctgtctg tggaatgcta caggcgttgt    480

agtttgtact ggtgacgaaa ctcagtgtta cggtacatgg gttcctattg ggcttgctat    540

ccctgaaaat gagggtggtg gctctgaggg tggcggttct gagggtggcg gctctgaggg    600

tggcggtact aaacctcctg agtacggtga tacacctatt ccgggctata cttatatcaa    660

ccctctcgac ggcacttatc cgcctggtac tgagcaaaac cccgctaatc ctaatccttc    720

tcttgaggag tctcagcctc ttaatacttt catgtttcag aataataggt tccgaaatag    780

gcagggggca ttaactgttt atacgggcac tgttactcaa ggcactgacc ccgttaaaac    840

ttattaccag tacactcctg tatcatcaaa agccatgtat gacgcttact ggaacggtaa    900

attcagagac tgcgctttcc attctggctt taatgaggat ccattcgttt gtgaatatca    960

aggccaatcg tctgacctgc ctcaacctcc tgtcaatgct ggcggcggct ctggtggtgg   1020

ttctggtggc ggctctgagg gtggcggctc tgagggtggc ggttctgagg gtggcggctc   1080
```

-continued

```
tgagggtggc ggttccggtg gcggctccgg ttccggtgat tttgattatg aaaaaatggc   1140

aaacgctaat aagggggcta tgaccgaaaa tgccgatgaa aacgcgctac agtctgacgc   1200

taaaggcaaa cttgattctg tcgctactga ttacggtgct gctatcgatg gtttcattgg   1260

tgacgtttcc ggccttgcta atggtaatgg tgctactggt gattttgctg gctctaattc   1320

ccaaatggct caagtcggtg acggtgataa ttcaccttta atgaataatt tccgtcaata   1380

tttaccttct ttgcctcagt cggttgaatg tcgcccttat gtctttggcg ctggtaaacc   1440

atatgaattt tctattgatt gtgacaaaat aaacttattc cgtggtgtct ttgcgtttct   1500

tttatatgtt gccaccttta tgtatgtatt ttcgacgttt gctaacatac tgcgtaataa   1560

ggagtcttaa gctt                                                     1574
```

```
<210> SEQ ID NO 39
<211> LENGTH: 932
<212> TYPE: DNA
<213> ORGANISM: artificial sequence
<220> FEATURE:
<223> OTHER INFORMATION: Description of Artificial Sequence: expression
      cassette

<400> SEQUENCE: 39

gctagcctga ggccagtttg ctcaggctct ccccgtggag gtaataattg ctcgaccgat     60

aaaagcggct tcctgacagg aggccgtttt gttttgcagc ccacctcaac gcaattaatg    120

tgagttagct cactcattag gcaccccagg ctttacactt tatgcttccg gctcgtatgt    180

tgtgtggaat tgtgagcgga taacaatttc acacaggaaa cagctatgac catgattacg    240

aatttctaga taacgagggc aaaaaatgaa aaagacagct atcgcgattg cagtggcact    300

ggctggtttc gctaccgtag cgcaggccga ctactgcgat atcgaattca atgctggcgg    360

cggctctggt ggtggttctg gtggcggctc tgagggtggt ggctctgagg gtggcggttc    420

tgagggtggc ggctctgagg gaggcggttc cggtggtggc tctggttccg gtgattttga    480

ttatgaaaag atggcaaacg ctaataaggg ggctatgacc gaaaatgccg atgaaaacgc    540

gctacagtct gacgctaaag gcaaacttga ttctgtcgct actgattacg gtgctgctat    600

cgatggtttc attggtgacg tttccggcct tgctaatggt aatggtgcta ctggtgattt    660

tgctggctct aattcccaaa tggctcaagt cggtgacggt gataattcac ctttaatgaa    720

taatttccgt caatatttac cttccctccc tcaatcggtt gaatgtcgcc cttttgtctt    780

tggcgctggt aaaccatatg aattttctat tgattgtgac aaaataaact tattccgtgg    840

tgtctttgcg tttcttttat atgttgccac ctttatgtat gtattttcta cgtttgctaa    900

catactgcgt aataaggagt cttgataagc tt                                  932
```

```
<210> SEQ ID NO 40
<211> LENGTH: 4425
<212> TYPE: DNA
<213> ORGANISM: artificial sequence
<220> FEATURE:
<223> OTHER INFORMATION: Description of Artificial Sequence: vector

<400> SEQUENCE: 40

tctagataac gagggcaaaa aatgaaaaag acagctatcg cgattgcagt ggcactggct     60

ggtttcgcta ccgtagcgca ggccgactac tgcgatatcg aattcgcaga aacagttgaa    120

agttgtttag caaaacccca tacagaaaat tcatttacta acgtctggaa agacgacaaa    180

actttagatc gttacgctaa ctatgagggc tgtctgtgga atgctacagg cgttgtagtt    240
```

-continued

```
tgtactggtg acgaaactca gtgttacggt acatgggttc ctattgggct tgctatccct    300
gaaaatgagg gtggtggctc tgagggtggc ggttctgagg gtggcggctc tgagggtggc    360
ggtactaaac ctcctgagta cggtgataca cctattccgg gctatactta tatcaaccct    420
ctcgacggca cttatccgcc tggtactgag caaaaccccg ctaatcctaa tccttctctt    480
gaggagtctc agcctcttaa tactttcatg tttcagaata ataggttccg aaataggcag    540
ggggcattaa ctgtttatac gggcactgtt actcaaggca ctgaccccgt taaaacttat    600
taccagtaca ctcctgtatc atcaaaagcc atgtatgacg cttactggaa cggtaaattc    660
agagactgcg ctttccattc tggctttaat gaggatccat tcgtttgtga atatcaaggc    720
caatcgtctg acctgcctca acctcctgtc aatgctggcg gcggctctgg tggtggttct    780
ggtggcggct ctgagggtgg cggctctgag ggtggcggtt ctgagggtgg cggctctgag    840
ggtggcggtt ccggtggcgg ctccggttcc ggtgattttg attatgaaaa aatggcaaac    900
gctaataagg gggctatgac cgaaaatgcc gatgaaaacg cgctacagtc tgacgctaaa    960
ggcaaacttg attctgtcgc tactgattac ggtgctgcta tcgatggttt cattggtgac   1020
gtttccggcc ttgctaatgg taatggtgct actggtgatt ttgctggctc taattcccaa   1080
atggctcaag tcggtgacgg tgataattca cctttaatga ataatttccg tcaatattta   1140
ccttctttgc ctcagtcggt tgaatgtcgc ccttatgtct ttggcgctgg taaaccatat   1200
gaattttcta ttgattgtga caaaataaac ttattccgtg gtgtctttgc gtttctttta   1260
tatgttgcca cctttatgta tgtattttcg acgtttgcta acatactgcg taataaggag   1320
tcttaaggcc tgataagcat gcgtaggaga aaataaaatg aaacaaagca ctattgcact   1380
ggcactctta ccgttgctct tcacccctgt taccaaagcc gactacaaag atgaagtgca   1440
attggtggaa agcggcggcg gcctggtgca accgggcggc agcctgcgtc tgagctgcgc   1500
ggcctccgga tttaccttta gcagctatgc gatgagctgg gtgcgccaag cccctgggaa   1560
gggtctcgag tgggtgagcg cgattagcgg tagcggcggc agcacctatt atgcggatag   1620
cgtgaaaggc cgttttacca tttcacgtga taattcgaaa aacaccctgt atctgcaaat   1680
gaacagcctg cgtgcggaag atacggccgt gtattattgc gcgcgtcgtt ctggtgctta   1740
tgattattgg ggccaaggca ccctggtgac ggttagctca gcgggtggcg gttctggcgg   1800
cggtgggagc ggtggcggtg gttctggcgg tggtggttcc gatatcgtga tgacccagag   1860
cccggatagc ctggcggtga gcctgggcga acgtgcgacc attaactgca gaagcagcca   1920
gagcgtgctg tatagcagca acaacaaaaa ctatctggcg tggtaccagc agaaaccagg   1980
tcagccgccg aaactattaa tttattgggc atccacccgt gaaagcgggg tcccggatcg   2040
ttttagcggc tctggatccg gcactgattt taccctgacc atttcgtccc tgcaagctga   2100
agacgtggcg gtgtattatt gccagcagta ttcttctttt cctcttacct ttggccaggg   2160
tacgaaagtt gaaattaaac gtacggaatt cccagggggg agcggaggcg cgccgcacca   2220
tcatcaccat cactgctgat aagcttgacc tgtgaagtga aaaatggcgc agattgtgcg   2280
acattttttt tgtctgccgt ttaatgaaat tgtaaacgtt aatattttgt taaaattcgc   2340
gttaaatttt tgttaaatca gctcattttt taaccaatag gccgaaatcg gcaaaatccc   2400
ttataaatca aaagaataga ccgagatagg gttgagtgtt gttccagttt ggaacaagag   2460
tccactatta aagaacgtgg actccaacgt caaagggcga aaaaccgtct atcagggcga   2520
tggcccacta cgagaaccat caccctaatc aagttttttg gggtcgaggt gccgtaaagc   2580
actaaatcgg aaccctaaag ggagcccccg atttagagct tgacggggaa agccggcgaa   2640
```

-continued

```
cgtggcgaga aaggaaggga agaaagcgaa aggagcgggc gctagggcgc tggcaagtgt   2700

agcggtcacg ctgcgcgtaa ccaccacacc cgccgcgctt aatgcgccgc tacagggcgc   2760

gtgctagcca tgtgagcaaa aggccagcaa aaggccagga accgtaaaaa ggccgcgttg   2820

ctggcgtttt tccataggct ccgcccccct gacgagcatc acaaaaatcg acgctcaagt   2880

cagaggtggc gaaacccgac aggactataa agataccagg cgtttccccc tggaagctcc   2940

ctcgtgcgct ctcctgttcc gaccctgccg cttaccggat acctgtccgc ctttctccct   3000

tcgggaagcg tggcgctttc tcatagctca cgctgtaggt atctcagttc ggtgtaggtc   3060

gttcgctcca agctgggctg tgtgcacgaa ccccccgttc agtccgaccg ctgcgcctta   3120

tccggtaact atcgtcttga gtccaacccg gtaagacacg acttatcgcc actggcagca   3180

gccactggta acaggattag cagagcgagg tatgtaggcg gtgctacaga gttcttgaag   3240

tggtggccta actacggcta cactagaaga acagtatttg gtatctgcgc tctgctgtag   3300

ccagttacct tcggaaaaag agttggtagc tcttgatccg gcaaacaaac caccgctggt   3360

agcggtggtt tttttgtttg caagcagcag attacgcgca gaaaaaaagg atctcaagaa   3420

gatcctttga tcttttctac ggggtctgac gctcagtgga acgaaaactc acgttaaggg   3480

attttggtca gatctagcac caggcgttta agggcaccaa taactgcctt aaaaaaatta   3540

cgccccgccc tgccactcat cgcagtactg ttgtaattca ttaagcattc tgccgacatg   3600

gaagccatca caaacggcat gatgaacctg aatcgccagc ggcatcagca ccttgtcgcc   3660

ttgcgtataa tatttgccca tagtgaaaac gggggcgaag aagttgtcca tattggctac   3720

gtttaaatca aaactggtga aactcaccca gggattggct gagacgaaaa acatattctc   3780

aataaaccct ttagggaaat aggccaggtt ttcaccgtaa cacgccacat cttgcgaata   3840

tatgtgtaga aactgccgga aatcgtcgtg gtattcactc cagagcgatg aaaacgtttc   3900

agtttgctca tggaaaacgg tgtaacaagg gtgaacacta tcccatatca ccagctcacc   3960

gtctttcatt gccatacgga actccgggtg agcattcatc aggcgggcaa gaatgtgaat   4020

aaaggccgga taaaacttgt gcttattttt ctttacggtc tttaaaaagg ccgtaatatc   4080

cagctgaacg gtctggttat aggtacattg agcaactgac tgaaatgcct caaaatgttc   4140

tttacgatgc cattgggata tatcaacggt ggtatatcca gtgatttttt tctccatttt   4200

agcttcctta gctcctgaaa atctcgataa ctcaaaaaat acgcccggta gtgatcttat   4260

ttcattatgg tgaaagttgg aacctcaccc gacgtctaat gtgagttagc tcactcatta   4320

ggcaccccag gctttacact ttatgcttcc ggctcgtatg ttgtgtggaa ttgtgagcgg   4380

ataacaattt cacacaggaa acagctatga ccatgattac gaatt                   4425
```

<210> SEQ ID NO 41
<211> LENGTH: 5079
<212> TYPE: DNA
<213> ORGANISM: artificial sequence
<220> FEATURE:
<223> OTHER INFORMATION: Description of Artificial Sequence: vector

<400> SEQUENCE: 41

```
tctagataac gagggcaaaa aatgaaaaag acagctatcg cgattgcagt ggcactggct     60

ggtttcgcta ccgtagcgca ggccgatatc gtgctgaccc agccgccttc agtgagtggc    120

gcaccaggtc agcgtgtgac catctcgtgt agcggcagca gcagcaacat tggcagcaac    180

tatgtgagct ggtaccagca gttgcccggg acggcgccga aactgctgat ttatgataac    240
```

-continued

```
aaccagcgtc cctcaggcgt gccggatcgt tttagcggat ccaaaagcgg caccagcgcg    300
agccttgcga ttacgggcct gcaaagcgaa gacgaagcgg attattattg ccagagctat    360
gaccagaatg ctcttgttga ggtgtttggc ggcggcacga agttaaccgt tcttggccag    420
ccgaaagccg caccgagtgt gacgctgttt ccgccgagca gcgaagaatt gcaggcgaac    480
aaagcgaccc tggtgtgcct gattagcgac ttttatccgg gagccgtgac agtggcctgg    540
aaggcagata gcagccccgt caaggcggga gtggagacca ccacaccctc caaacaaagc    600
aacaacaagt acgcggccag cagctatctg agcctgacgc ctgagcagtg gaagtcccac    660
agaagctaca gctgccaggt cacgcatgag gggagcaccg tggaaaaaac cgttgcgccg    720
actgaggcct ctccaggggg gagcggaggc gcgccgcacc atcatcacca tcactgctga    780
taatatgcat gcgtaggaga aaataaaatg aaacaaagca ctattgcact ggcactctta    840
ccgttgctct tcacccctgt taccaaagcc caggtgcaat tgaaagaaag cggcccggcc    900
ctggtgaaac cgacccaaac cctgaccctg acctgtacct tttccggatt tagcctgtcc    960
acgtctggcg ttggcgtggg ctggattcgc cagccgcctg ggaaagccct cgagtggctg   1020
gctctgattg attgggatga tgataagtat tatagcacca gcctgaaaac gcgtctgacc   1080
attagcaaag atacttcgaa aaatcaggtg gtgctgacta tgaccaacat ggacccggtg   1140
gatacggcca cctattattg cgcgcgtttt gatccttttt ttgattcttt ttttgattat   1200
tggggccaag gcaccctggt gacggttagc tcagcgtcga ccaaaggtcc aagcgtgttt   1260
ccgctggctc cgagcagcaa aagcaccagc ggcggcacgg ctgccctggg ctgcctggtt   1320
aaagattatt tcccggaacc agtcaccgtg agctggaaca gcggggcgct gaccagcggc   1380
gtgcatacct ttccggcggt gctgcaaagc agcggcctgt atagcctgag cagcgttgtg   1440
accgtgccga gcagcagctt aggcactcag acctatattt gcaacgtgaa ccataaaccg   1500
agcaacacca aagtggataa aaaagtggaa ccgaaaagcg aattcgacta taaagatgac   1560
gatgacaaag gcgcgccgtg gagccacccg cagtttgaaa aatgataagc ttgacctgtg   1620
aagtgaaaaa tggcgcagat tgtgcgacat tttttttgtc tgccgtttaa ttaaaggggg   1680
ggggggccg gcctgggggg gggtgtacat gaaattgtaa acgttaatat tttgttaaaa   1740
ttcgcgttaa atttttgtta aatcagctca ttttttaacc aataggccga aatcggcaaa   1800
atcccttata aatcaaaaga atagaccgag atagggttga gtgttgttcc agtttggaac   1860
aagagtccac tattaaagaa cgtggactcc aacgtcaaag ggcgaaaaac cgtctatcag   1920
ggcgatggcc cactacgaga accatcaccc taatcaagtt ttttggggtc gaggtgccgt   1980
aaagcactaa atcggaaccc taaagggagc ccccgattta gagcttgacg gggaaagccg   2040
gcgaacgtgg cgagaaagga agggaagaaa gcgaaaggag cgggcgctag ggcgctggca   2100
agtgtagcgg tcacgctgcg cgtaaccacc acacccgccg cgcttaatgc gccgctacag   2160
ggcgcgtgct agactagtgt ttaaaccgga ccgggggggg gcttaagtgg gctgcaaaac   2220
aaaacggcct cctgtcagga agccgctttt atcgggtagc ctcactgccc gctttccagt   2280
cgggaaacct gtcgtgccag ctgcatcagt gaatcggcca acgcgcgggg agaggcggtt   2340
tgcgtattgg gagccagggt ggtttttctt ttcaccagtg agacgggcaa cagctgattg   2400
cccttcaccg cctggccctg agagagttgc agcaagcggt ccacgctggt ttgccccagc   2460
aggcgaaaat cctgtttgat ggtggtcagc ggcgggatat aacatgagct gtcctcggta   2520
tcgtcgtatc ccactaccga gatgtccgca ccaacgcgca gcccggactc ggtaatggca   2580
cgcattgcgc ccagcgccat ctgatcgttg gcaaccagca tcgcagtggg aacgatgccc   2640
```

-continued

```
tcattcagca tttgcatggt ttgttgaaaa ccggacatgg cactccagtc gccttcccgt   2700
tccgctatcg gctgaatttg attgcgagtg agatatttat gccagccagc cagacgcaga   2760
cgcgccgaga cagaacttaa tgggccagct aacagcgcga tttgctggtg gcccaatgcg   2820
accagatgct ccacgcccag tcgcgtaccg tcctcatggg agaaaataat actgttgatg   2880
ggtgtctggt cagagacatc aagaaataac gccggaacat tagtgcaggc agcttccaca   2940
gcaatagcat cctggtcatc cagcggatag ttaataatca gcccactgac acgttgcgcg   3000
agaagattgt gcaccgccgc tttacaggct tcgacgccgc ttcgttctac catcgacacg   3060
accacgctgg cacccagttg atcggcgcga gatttaatcg ccgcgacaat ttgcgacggc   3120
gcgtgcaggg ccagactgga ggtggcaacg ccaatcagca acgactgttt gcccgccagt   3180
tgttgtgcca cgcggttagg aatgtaattc agctccgcca tcgccgcttc cactttttcc   3240
cgcgttttcg cagaaacgtg gctggcctgg ttcaccacgc gggaaacggt ctgataagag   3300
acaccggcat actctgcgac atcgtataac gttactggtt tcacattcac caccctgaat   3360
tgactctctt ccgggcgcta tcatgccata ccgcgaaagg ttttgcgcca ttcgatgcta   3420
gccatgtgag caaaaggcca gcaaaaggcc aggaaccgta aaaaggccgc gttgctggcg   3480
tttttccata ggctccgccc ccctgacgag catcacaaaa atcgacgctc aagtcagagg   3540
tggcgaaacc cgacaggact ataaagatac caggcgtttc cccctggaag ctccctcgtg   3600
cgctctcctg ttccgaccct gccgcttacc ggatacctgt ccgcctttct cccttcggga   3660
agcgtggcgc tttctcatag ctcacgctgt aggtatctca gttcggtgta ggtcgttcgc   3720
tccaagctgg gctgtgtgca cgaacccccc gttcagcccg accgctgcgc cttatccggt   3780
aactatcgtc ttgagtccaa cccggtaaga cacgacttat cgccactggc agcagccact   3840
ggtaacagga ttagcagagc gaggtatgta ggcggtgcta cagagttctt gaagtggtgg   3900
cctaactacg gctacactag aagaacagta tttggtatct gcgctctgct gtagccagtt   3960
accttcggaa aaagagttgg tagctcttga tccggcaaac aaaccaccgc tggtagcggt   4020
ggtttttttg tttgcaagca gcagattacg cgcagaaaaa aaggatctca agaagatcct   4080
ttgatctttt ctacggggtc tgacgctcag tggaacgaaa actcacgtta agggattttg   4140
gtcagatcta gcaccaggcg tttaagggca ccaataactg ccttaaaaaa attacgcccc   4200
gccctgccac tcatcgcagt actgttgtaa ttcattaagc attctgccga catggaagcc   4260
atcacaaacg gcatgatgaa cctgaatcgc cagcggcatc agcaccttgt cgccttgcgt   4320
ataatatttg cccatagtga aaacgggggc gaagaagttg tccatattgg ctacgtttaa   4380
atcaaaactg gtgaaactca cccagggatt ggctgagacg aaaaacatat tctcaataaa   4440
ccctttaggg aaataggcca ggttttcacc gtaacacgcc acatcttgcg aatatatgtg   4500
tagaaactgc cggaaatcgt cgtggtattc actccagagc gatgaaaacg tttcagtttg   4560
ctcatggaaa acggtgtaac aagggtgaac actatcccat atcaccagct caccgtcttt   4620
cattgccata cggaactccg ggtgagcatt catcaggcgg gcaagaatgt gaataaaggc   4680
cggataaaac ttgtgcttat ttttctttac ggtctttaaa aaggccgtaa tatccagctg   4740
aacggtctgg ttataggtac attgagcaac tgactgaaat gcctcaaaat gttctttacg   4800
atgccattgg gatatatcaa cggtggtata tccagtgatt tttttctcca ttttagcttc   4860
cttagctcct gaaaatctcg ataactcaaa aaatacgccc ggtagtgatc ttatttcatt   4920
atggtgaaag ttggaacctc acccgacgtc taatgtgagt tagctcactc attaggcacc   4980
```

-continued

```
ccaggcttta cactttatgc ttccggctcg tatgttgtgt ggaattgtga gcggataaca   5040

atttcacaca ggaaacagct atgaccatga ttacgaatt                           5079
```